(12) United States Patent
Ahmad et al.

(10) Patent No.: US 7,371,759 B2
(45) Date of Patent: May 13, 2008

(54) HMG-COA REDUCTASE INHIBITORS AND METHOD

(75) Inventors: Saleem Ahmad, Wall, NJ (US); Jeffrey A. Robl, Newtown, PA (US); Khehyong Ngu, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 416 days.

(21) Appl. No.: 10/946,055

(22) Filed: Sep. 21, 2004

(65) Prior Publication Data

US 2005/0085497 A1 Apr. 21, 2005

Related U.S. Application Data

(60) Provisional application No. 60/505,893, filed on Sep. 25, 2003.

(51) Int. Cl.
*C07D 239/42* (2006.01)
*C07D 403/12* (2006.01)
*C07D 403/14* (2006.01)
*C07D 413/12* (2006.01)
*C07D 413/14* (2006.01)
*C07D 417/12* (2006.01)
*C07D 417/14* (2006.01)
*A61K 31/506* (2006.01)
*A61P 3/06* (2006.01)
*A61P 3/10* (2006.01)

(52) U.S. Cl. ............ 514/275; 544/330; 544/331; 544/332

(58) Field of Classification Search ............ 544/330, 544/331, 332; 514/275
See application file for complete search history.

(56) References Cited

U.S. PATENT DOCUMENTS

| | | |
|---|---|---|
| 3,674,836 A | 7/1972 | Creger |
| 4,027,009 A | 5/1977 | Grier et al. |
| 4,046,889 A | 9/1977 | Ondetti et al. |
| 4,168,267 A | 9/1979 | Petrillo, Jr. |
| 4,316,906 A | 2/1982 | Ondetti et al. |
| 4,337,201 A | 6/1982 | Petrillo, Jr. |
| 4,374,829 A | 2/1983 | Harris et al. |
| 4,379,785 A | 4/1983 | Weyer et al. |
| 4,405,552 A | 9/1983 | Miesel |
| 4,432,971 A | 2/1984 | Karanewsky et al. |
| 4,452,790 A | 6/1984 | Karanewsky et al. |
| 4,572,912 A | 2/1986 | Yoshioka et al. |
| 4,639,436 A | 1/1987 | Junge et al. |
| 4,722,810 A | 2/1988 | Delaney et al. |
| 4,749,688 A | 6/1988 | Haslanger et al. |
| 4,759,923 A | 7/1988 | Buntin et al. |
| 4,871,721 A | 10/1989 | Biller |
| 4,904,769 A | 2/1990 | Rauenbusch |
| 4,924,024 A | 5/1990 | Biller |
| 4,929,437 A | 5/1990 | Tobert |
| 4,933,165 A | 6/1990 | Brown |
| 5,100,889 A | 3/1992 | Misra et al. |
| 5,223,516 A | 6/1993 | Delaney et al. |
| 5,225,401 A | 7/1993 | Seymour |
| 5,260,440 A | 11/1993 | Hirai et al. |

(Continued)

FOREIGN PATENT DOCUMENTS

DE 40 23 308 1/1992

(Continued)

OTHER PUBLICATIONS

Wolft Manfred E. "Burger's Medicinal Chemistry, 5ed, Part 1", John Wiley & Sons, 1995, pp. 975-977.*

(Continued)

*Primary Examiner*—Venkataraman Balasubram
(74) *Attorney, Agent, or Firm*—Burton Rodney

(57) ABSTRACT

Compounds are provided having the following structure which are HMG CoA reductase inhibitors and thus are active in inhibiting cholesterol biosynthesis, modulating blood serum lipids, for example, lowering LDL cholesterol and/or increasing HDL cholesterol, and treating hyperlipidemia, dyslipidemia, hormone replacement therapy, hypercholsterolemia, hypertriglyceridemia and atherosclerosis as well as Alzheimer's disease and osteoporosis

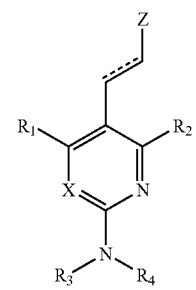

wherein X is N or $CR_5$;
and pharmaceutically acceptable salts thereof,

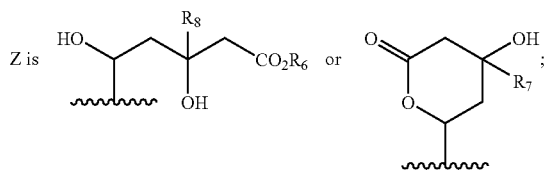

wherein $R_1$ to $R_7$ are as defined herein.

A method for treating the above diseases employing the above compounds is also provided.

20 Claims, No Drawings

U.S. PATENT DOCUMENTS

| | | | |
|---|---|---|---|
| 5,316,765 A | 5/1994 | Folkers et al. |
| 5,346,701 A | 9/1994 | Heiber et al. |
| 5,362,727 A | 11/1994 | Robl |
| 5,366,973 A | 11/1994 | Flynn et al. |
| 5,447,954 A | 9/1995 | Gribble et al. |
| 5,488,064 A | 1/1996 | Sher |
| 5,491,134 A | 2/1996 | Sher et al. |
| 5,504,080 A | 4/1996 | Karanewsky |
| 5,525,723 A | 6/1996 | Robl |
| 5,541,204 A | 7/1996 | Sher et al. |
| 5,552,397 A | 9/1996 | Karanewsky et al. |
| 5,594,016 A | 1/1997 | Ueno et al. |
| 5,595,872 A | 1/1997 | Wetterau, II et al. |
| 5,612,359 A | 3/1997 | Murugesan |
| 5,614,492 A | 3/1997 | Habener |
| 5,631,224 A | 5/1997 | Efendic et al. |
| 5,646,176 A | 7/1997 | Golik et al. |
| 5,698,527 A | 12/1997 | Kim |
| 5,712,279 A | 1/1998 | Biller et al. |
| 5,712,396 A | 1/1998 | Magnin et al. |
| 5,739,135 A | 4/1998 | Biller et al. |
| 5,760,246 A | 6/1998 | Biller et al. |
| 5,770,615 A | 6/1998 | Cheng et al. |
| 5,776,983 A | 7/1998 | Washburn et al. |
| 5,827,875 A | 10/1998 | Dickson, Jr. et al. |
| 5,885,983 A | 3/1999 | Biller et al. |
| 5,962,440 A | 10/1999 | Sulsky |
| 6,218,408 B1 | 4/2001 | Marzabadi et al. |
| RE37,314 E | 8/2001 | Hirai et al. |
| 6,395,767 B2 | 5/2002 | Robl et al. |
| 6,414,126 B1 | 7/2002 | Ellsworth et al. |
| 6,469,024 B2 | 10/2002 | Li et al. |
| 6,515,117 B2 | 2/2003 | Ellsworth et al. |
| 6,525,203 B1 | 2/2003 | Tino |
| 6,548,529 B1 | 4/2003 | Robl et al. |
| 6,573,287 B2 | 6/2003 | Sulsky et al. |
| 6,750,246 B1 | 6/2004 | Kadow et al. |
| 6,800,605 B1 | 10/2004 | Friends et al. |

FOREIGN PATENT DOCUMENTS

| | | |
|---|---|---|
| DE | 196 22 222 | 12/1997 |
| EP | 0 367 895 | 5/1990 |
| EP | 0416383 A2 | 3/1991 |
| EP | 0 465 970 | 1/1992 |
| EP | 0 534 396 | 10/1996 |
| EP | 0 595 610 | 5/1997 |
| EP | 0 534 363 | 7/1997 |
| EP | 0 481 522 | 12/1997 |
| EP | 0 599 444 | 1/1998 |
| EP | 0 675 714 | 1/1999 |
| EP | 0 970 694 | 1/2000 |
| EP | 0 992 496 | 4/2000 |
| EP | 0 521 471 | 10/2000 |
| EP | 0 818 448 | 11/2003 |
| EP | 0 629 627 | 5/2004 |
| EP | 1 022 272 | 5/2004 |
| GB | 2 304 106 | 3/1997 |
| JP | 6-256318 | 9/1994 |
| WO | WO 94/14787 | 7/1994 |
| WO | WO 94/15592 | 7/1994 |
| WO | WO 96/38144 | 12/1996 |
| WO | WO 97/12613 | 4/1997 |
| WO | WO 97/12615 | 4/1997 |
| WO | WO 97/21993 | 6/1997 |
| WO | WO 97/35576 | 10/1997 |
| WO | WO 97/48701 | 12/1997 |
| WO | WO 99/00353 | 1/1999 |
| WO | WO 99/38501 | 8/1999 |
| WO | WO 99/44609 | 9/1999 |
| WO | WO 99/45913 | 9/1999 |
| WO | WO 99/46272 | 9/1999 |
| WO | WO 99/58518 | 11/1999 |
| WO | WO 99/58521 | 11/1999 |
| WO | WO 99/58522 | 11/1999 |
| WO | WO 99/61431 | 12/1999 |
| WO | WO 99/61435 | 12/1999 |
| WO | WO 99/64002 | 12/1999 |
| WO | WO 99/67278 | 12/1999 |
| WO | WO 99/67279 | 12/1999 |
| WO | WO 00/03746 | 1/2000 |
| WO | WO 00/15201 | 3/2000 |
| WO | WO 00/30665 | 6/2000 |
| WO | WO 00/38722 | 7/2000 |
| WO | WO 00/50574 | 8/2000 |
| WO | WO 00/53605 | 9/2000 |
| WO | WO 00/77010 | 12/2000 |
| WO | WO 01/13917 | 3/2001 |
| WO | WO 01/14376 | 3/2001 |
| WO | WO 02/098854 | 12/2002 |
| WO | WO 03/011824 | 2/2003 |
| WO | WO 03/072197 | 9/2003 |

OTHER PUBLICATIONS

Banker, G.S. et al, "Modern Pharmaceutics, 3ed.", Marcel Dekker, New York. 1996, pp. 451 and 596.*
Cecil Textbook of Medicine, edited by Bennet, J.C., and Plum F., 20th edition, vol. 1, 1004-1010, 1996.*
Khan et al., Diabetes Care 25(4), 708-711, 2002.*
Iida et al., FEBS Letters 520, 177-181, 2002.*
Rutishauser Swiss Medical Weekly, 126, 41-49, 2006.*
U.S. Appl. No. 10/989,138, filed Nov. 15, 2004, O'Connor et al.
Ashworth, D.M. et al., "2-Cyanopyrrolidides as Potent, Stable Inhibitors of Dipeptidyl Peptidase IV", Bioorganic & Medicinial Chemistry Letters, vol. 6, No. 10, pp. 1163-1166 (1996).
Ashworth, D.M. et al., "4-Cyanothiazolidides as Very Potent, Stable Inhibitors of Dipeptidyl Peptidase IV", Bioorganic & Medicinial Chemistry Letters, vol. 6, No. 22, pp. 2745-2748 (1996).
Beck, G. et al., "Synthesis and Biological Activity of New HMG-CoA Reductase Inhibitors. 1. Lactones of Pyridine- and Pyrimidine-Substituted 3,5-Dihydroxy-6-heptenoic (-heptanoic) Acids", J. Med. Chem. vol. 33, No. 1, pp. 52-60 (1990).
Biller, S.A. et al., "Isoprenoid (Phosphinylmethyl)phosphonates as Inhibitors of Squalene Synthetase", Journal of Medicinal Chemistry, vol. 31, No. 10, pp. 1869-1871 (1988).
Biller, S.A. et al., "Squalene Synthase Inhibitors", Current Pharmaceutical Design, vol. 2, No. 1, pp. 1-40 (1996).
Capson, T.L., "Synthesis and Evaluation of Ammonium Analogs of Carbocationic Intermediates in Squalene Biosynthesis", dissertation, Department of Medicinal Chemistry, University of Utah, pp. iv-v, Table of Contents, 16-17, 40-43, 48-51, Summary (Jun. 1987).
Corey, E.J. et al., "Application of Unreactive Analogs of Terpenoid Pyrophosphates to Studies of Multistep Biosynthesis. Demonstration That 'Presqualene Pyrophosphate' Is an Essential Intermediate on the Path to Squalene", J. Am. Chem. Soc., vol. 98, No. 5, pp. 1291-1293 (1976).
Cornicelli, J.A. et al., "15-Lipoxygenase and Its Inhibition: A Novel Therapeutic Target for Vascular Disease", Current Pharmaceutical Design, vol. 5, No. 1, pp. 11-20 (1999).
Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol.16, No. 1, pp. 16-30 (1998).
Hara, S., "Ileal Na+/bile acid cotransporter inhibitors", Drugs of the Future, vol. 24, No. 4, pp. 425-430 (1999).
Hughes, T.E. et al., "NVP-DPP728: (1-[[[2-[(5-Cyanopyridin-2-yl)amino]ethyl]acetyl]-2-cyano-(S)-pyrrolidine), a Slow-Binding Inhibitor of Dipeptidyl Peptidase IV", Biochemistry, vol. 38, No. 36, pp. 11597-11603 (1999).
Johannsson, G. et al., "Growth Hormone Treatment of Abdominally Obese Men Reduces Abdominal Fat Mass, Improves Glucose and Lipoprotein Metabolism, and Reduces Diastolic Blood Pressure", Journal of Clinical Endocrinology and Metabolism, vol. 82, No. 3, pp. 727-734 (1997).

Krause, B.R. et al., Chapter 6: "ACAT Inhibitors: Physiologic Mechanisms for Hypolipidemic and Anti-Atherosclerotic Activities in Experimental Animals", Inflammation: Mediators and Pathways, CRC Press, Inc., publ., Ruffolo, Jr., R.R. et al., eds., pp. 173-198 (1995).

McClard, R.W. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Murakami, K. et al., "A Novel Insulin Sensitizer Acts as a Coligand for Peroxisome Proliferator-Activated Receptor-α (PPAR-α) and PPAR-γ: Effect of PPAR-α Activation on Abnormal Lipid Metabolism in Liver of Zucker Fatty Rats", Diabetes, vol. 47, pp. 1841-1847 (1998).

Nicolosi, R.J. et al., "The ACAT Inhibitor, Cl-1011 is effective in the prevention and regression of aortic fatty streak area in hamsters", Atherosclerosis, vol. 137, pp. 77-85 (1998).

Ortiz de Montellano, P.R. et al., "Inhibition of Squalene Synthetase by Farnesyl Pyrophosphate Analogues", Journal of Medicinal Chemistry, vol. 20, No. 2, pp. 243-249 (1977).

Rosenblum, S.B. et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem., vol. 41, No. 6, pp. 973-980 (1998).

Salisbury, B.G. et al., "Hypocholesterolemic activity of a novel inhibitor of cholesterol absorption, SCH 48461", Atherosclerosis, vol. 115, pp. 45-63 (1995).

Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).

Sliskovic, D.R. et al., "ACAT Inhibitors: Potential Anti-atherosclerotic Agents", Current Medicinal Chemistry, vol. 1, No. 3, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6, No. 1, pp. 47-50 (1996).

Sorbera, L.A. et al., "Avasimibe: Treatment of Lipoprotein Disorders—ACAT Inhibitor", Drugs of Future, vol. 24, No. 1, pp. 9-15 (1999).

Stout, D.M., "Inhibitors of Acyl-CoA:Cholesterol O-Acyl Transferase (ACAT) as Hypocholesterolemic Agents. 6. The First Water-Soluble ACAT Inhibitor with Lipid-Regulating Activity, etc. ", Chemtracts-Organic Chemistry, vol. 8, pp. 359-362 (1995).

Takata, Y. et al., "A Comparison of the Activity of the Angiotensin Converting Enzyme Inhibitors SQ 14 225, SA 446, and MK 421", Clinical and Experimental Pharmacology & Physiology, vol. 10, pp. 131-145 (1983).

Watanabe, M. et al., "Synthesis and Biological Activity of Methanesulfonamide Pyrimidine- and N-Methanesulfonyl Pyrrole-Substituted 3,5-Dihydroxy-6-heptenoates, a Novel Series of HMG-CoA Reductase Inhibitors", Bioorganic & Medicinal Chemistry, vol. 5, No. 2, pp. 437-444 (1997).

Yamada, M. et al., "A Potent Dipeptide Inhibitor of Dipeptidyl Peptidase IV", Bioorganic & Medicinal Chemistry Letters, vol. 8, pp. 1537-1540 (1998).

* cited by examiner

HMG-COA REDUCTASE INHIBITORS AND METHOD

FIELD OF THE INVENTION

This application claims a benefit of priority from U.S. Provisional Application No. 60/505,893 filed as Sep. 25, 2003, the entire disclsoure of which is herein incorporated by reference.

The present invention relates to compounds and pharmaceutical compositions useful as hypocholesterolemic and hypolipidemic agents. More particularly, this invention concerns (1) certain inhibitors of the enzyme 3-hydroxy-3-methylglutaryl-coenzyme A reductase (HMG-CoA reductase) that include a pyridine- or a pyrimidine-containing nucleus attached by means of a linker to an HMG-binding domain sidechain, (2) pharmaceutical compositions containing such compounds and (3) a method of lowering blood serum cholesterol levels and modulating blood serum lipid levels employing such pharmaceutical compositions.

BACKGROUND OF THE INVENTION

U.S. Pat. No. 5,260,440 and Reissue 37314 disclose rosuvastatin which has the structure

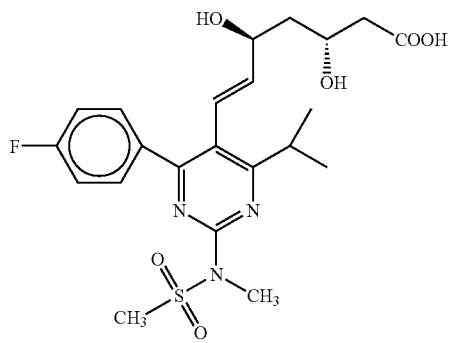

Rosuvastatin is also disclosed in Masamichi Watanabe et al. (Bioorganic & Medicinal Chemistry (1997), 5(2), 437-444).

Japanese Patent Application 06256318-A (corresponding to Japanese Patent 3197971 granted Aug. 1, 2001) discloses 5-carboalkoxy pyrimidine derivatives of the structure

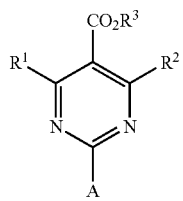

where $R^1$, $R^2$ and $R^3$ can be independently H, alkyl, aryl or heteroaryl, and A can be $NR^7R^8$ where $R^7$ and $R^8$ can be independently H, alkyl, aryl and heteroaryl among others. It is disclosed that these compounds are intermediates for preparing HMG CoA reductase inhibitors.

Beck et al., Synthesis and Biological Activity of New HMG-CoA Reductase Inhibitors. 1. Lactones of Pyridine— and Pyrimidine-Substituted 3,5-Dihydroxy-6-heptenoic (-heptanoic) Acids, J. Med. Chem. 1990, 33, 52-60 (mentioned in Japanese Patent Application 06256318-A) discloses compounds of the structure

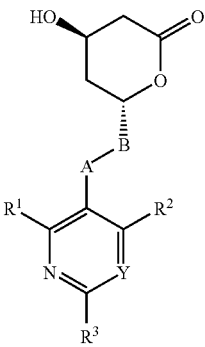

where Y can be CH or N;
A-B may be —CH=CH—;
$R^1$ may be an alkyl including i-$CH_3H_7$;
$R^2$ may be an aryl inclulng 4-$FC_6H_4$; and
$R^3$ may be an alkyl or an aryl;

which compounds may be prepared from intermediates of the structure

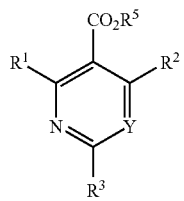

EP367895 (mentioned in Japanese Patent Application 06256318-A) discloses pyrimidinyl-substituted hydroxyacids, lactones and esters which are inhibitors of cholesterol biosynthesis and have the structure

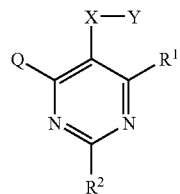

where $R^1$ can be alkyl;
Q can be aryl;
X can be —$CH_2CH_2$— or —CH=CH—;
Y can be

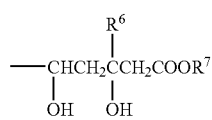

or a lactone thereof;

and $R^2$ can be $-N(R^8)_2$ where each $R^8$ is independently $C_1-C_4$ alkyl or both $R^8$ together with the nitrogen atom form part of a 5-,6- or 7-membered optionally substituted ring, which may contain a further oxygen heteroatom, preferably 4-morpholinyl. These compounds may be prepared using intermediates of the structure

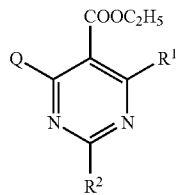

BRIEF DESCRIPTION OF THE INVENTION

In accordance with the present invention, there are provided certain pyridine-and pyrimidine-containing compounds that are potent inhibitors of cholesterol biosynthesis by virtue of their ability to inhibit the enzyme 3-methylglutaryl-coenzyme A reductase (HMG-CoA reductase).

In particular, in its broadest chemical compound aspect, the present invention provides compounds of the formula I

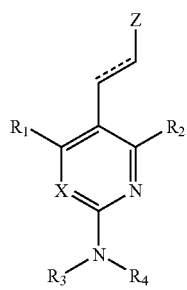

wherein X is N or $CR_5$;

$R_1$ and $R_2$ are the same or different and are independently selected from H, alkyl, alkoxyalkyl, arylalkyl, cycloalkyl, alkenyl, cycloalkenyl, aryl, heteroaryl or cycloheteroalkyl;

$R_3$ is aryl, heteroaryl, cycloalkyl, or cycloheteroalkyl;

$R_4$ is H, alkyl, cycloalkyl, haloalkyl, alkoxyalkyl, alkylthioalkyl, alkylsulfonyl, arylsulfonyl, alkoxycarbonyl, aryloxycarbonyl, heteroaryloxycarbonyl, alkylaminocarbonyl, arylaminocarbonyl, alkylthiocarbonyl, heteroarylaminocarbonyl, alkylaminosulfonyl, alkylcarbonyl, arylcarbonyl, heteroarylcarbonyl, or heteroarylsulfonyl;

$R_5$ is H or lower alkyl;

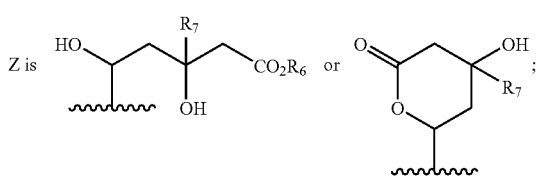

$R_6$ is H, or lower alkyl or a metal ion (such as an alkali metal or an alkaline earth metal);

$R_7$ is H or lower alkyl;

and ⟿ represents a single bond or a double bond (which may be cis or trans);

and including pharmaceutically acceptable salts thereof where $R_6$ is H, esters thereof, prodrug esters thereof, and all stereoisomers thereof.

Preferably, the Z group will be in form of a free acid, a physiologically acceptable and hydrolyzable ester or δ lactone thereof, or an alkali metal salt, alkaline earth metal salt, an amine salt or an amino acid salt.

Preferred are compounds of formula I of the invention wherein $R_1$ and $R_2$ are independently selected from alkyl, cycloalkyl and aryl;

$R_3$ is aryl, heteroaryl or cycloheteroalkyl;

$R_4$ is H, alkyl, lower alkylcarbonyl, lower alkylsulfonyl or lower alkoxycarbonyl.

More preferred are compounds of formula I of the invention wherein $R_1$ is aryl (especially substituted aryl as defined hereinafter);

$R_2$ is alkyl or cycloalkyl;

$R_3$ is aryl, heteroaryl or cycloheteroalkyl;

$R_4$ is H, alkyl, lower alkylcarbonyl, lower alkylsulfonyl, lower alkoxycarbonyl;

and ⟿ is a double bond, preferably "trans" and

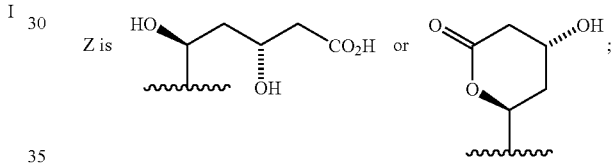

or an alkali or alkaline earth metal salt thereof, or an amino acid salt thereof, or an amine salt thereof.

Still more preferred are compounds of formula I of the invention wherein $R_1$ is substituted aryl, preferably 4-fluorophenyl, 4-fluoro-3-methylphenyl or 3,5-dimethylphenyl;

$R_2$ is alkyl or cycloalkyl, preferably isopropyl, t-butyl or cyclopropyl;

$R_3$ is aryl (preferably phenyl), cycloheteroalkyl (preferably tetrahydrothiophene dioxide), or heteroaryl (preferably a pyrazole, thiadiazole, pyrimidine, pyrazine, benzimidazole, triazole, tetrazole, pyridyl, thiazole, oxazole or isoxazole) wherein the above groups may be optionally substituted with 1, 2 or 3 substituents which may be alkylaminocarbonyl, cycloheteroalkyl, heteroaryl, alkyl, halogen, carboxyl, alkoxycarbonyl or alkoxy;

$R_4$ is H, $C_1-C_4$ alkyl, preferably methyl, $C_1-C_4$ alkylcarbonyl, preferably methylcarbonyl or $C_1-C_4$ alkylsulfonyl, preferably methanesulfonyl; ⟿ is a double bond, preferably "trans" and

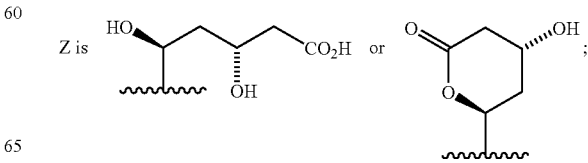

or an alkali or alkaline earth metal salt thereof or an amino acid salt thereof or an amine salt thereof.

Most preferred compounds of formula I of the invention will have the structure

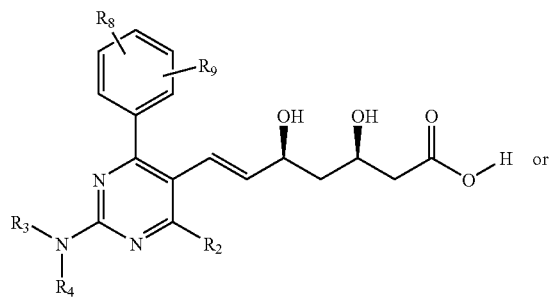

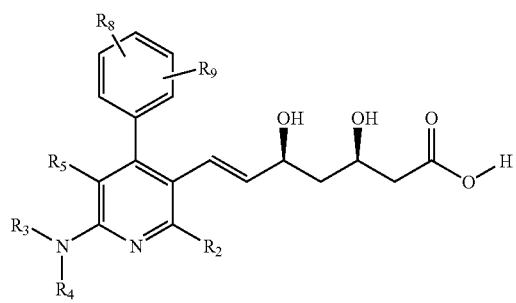

or an alkali or alkaline earth metal (such as Na, K or Ca) salt thereof, or an amino acid salt (such as arginine), or an amine salt thereof, wherein $R_8$ and $R_9$ are the same or different and independently selected from H, halogen and/or alkyl (preferably 4-fluoro, 4-fluoro-3-methyl or 3,5-dimethyl); and $R_2$ is alkyl or cycloalkyl, preferably isopropyl, t-butyl or cyclopropyl;

$R_3$ is one of the following groups:

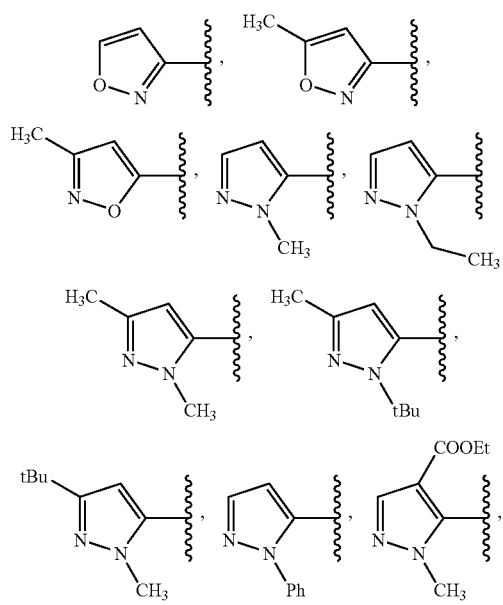

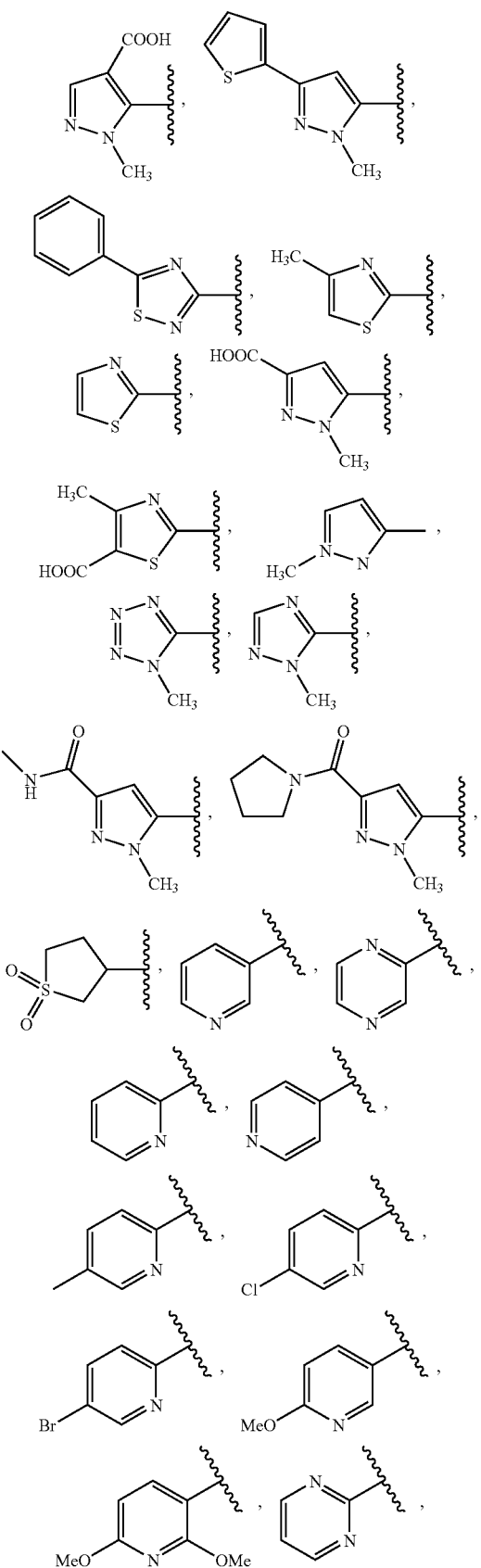

-continued

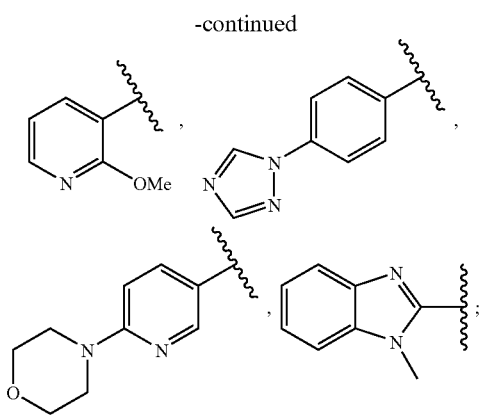

R<sub>4</sub> is H, alkyl, preferably methyl, or 4-methoxybenzyl, $C_1$-$C_4$ alkylcarbonyl, preferably methylcarbonyl, $C_1$-$C_4$ alkoxycarbonyl, preferably methoxycarbonyl or $C_1$-$C_4$ alkylsulfonyl, preferably methanesulfonyl;

R$_5$ is methyl.

In another aspect, the present invention provides pharmaceutical compositions, useful as hypolipidemic or hypocholesterolemic agents, or hypotriglyceridemic agents, or anti-Alzheimer's agents, or anti-osteoporosis agents as well as other uses as described herein, which contain a hypolipidemic or hypocholesterolemic or hypotriglyceridemic or anti-Alzheimer's disease or anti-osteoporosis amount, or other therapeutically effective amount (depending upon use) of a compound of formula I in accordance with this invention, in combination with a pharmaceutically acceptable carrier.

In another aspect, the present invention provides a method of inhibiting cholesterol biosynthesis or lowering blood serum cholesterol levels and/or modulating blood serum cholesterol levels such as lowering LDL cholesterol and/or increasing HDL cholesterol, and/or lowering triglycerides, or treating dyslipidemia, mixed dyslipidemia, hyperlipidemia, hypercholesterolemia, hypo α-lipoproteinemia, LDL Pattern B, LDL Pattern A, hyperlipoproteinemia or hypertriglyceridemia, and other aberrations of apolipoprotein B metabolism, or reducing levels of Lp(a), or treating or preventing other cholesterol-related diseases, or treating or preventing or reversing progression of atherosclerosis, or preventing or treating Alzheimer's disease, or preventing or treating osteoporosis and/or osteopenia, or reducing inflammatory markers such as C-reactive protein, or preventing or treating low grade vascular inflammation, or preventing or treating stroke, or preventing or treating dementia, or preventing and treating coronary heart disease (including primary and secondary prevention of myocardial infarction), or preventing or treating stable and unstable angina, or primary prevention of coronary events, or secondary prevention of cardiovascular events, or preventing or treating peripheral vascular disease, preventing or treating peripheral arterial disease, or preventing or treating acute vascular syndromes, or preventing or reducing the risk of undergoing myocardial revascularization procedures, or preventing or treating microvascular diseases such as nephropathy, neuropathy, retinopathy and nephrotic syndrome or preventing or treating hypertension in a patient in need of such treatment by administering a therapeutically effective amount of a compound of structure I or pharmaceutical composition containing same in accordance with the present invention as defined above.

In addition, in accordance with the present invention, a method is provided for preventing or treating diabetes, especially Type 2 diabetes, and related diseases such as insulin resistance, hyperglycemia, hyperinsulinemia, elevated blood levels of fatty acids or glycerol, obesity, Syndrome X, diabetic complications, dysmetabolic syndrome, and related diseases, and sexual dysfunction, wherein a therapeutically effective amount of a compound of structure I or composition containing same is administered to a patient in need of treatment.

In addition, in accordance with the present invention, a method is provided for preventing and treating malignant lesions (such as ductal carcinoma in situ of the breast and lobular carcinoma in situ of the breast), premalignant lesions (such as fibroadenoma of the breast and prostatic intraepithelial neoplasia (PIN), gastrointestinal malignencies, liposarcomas and various other epithelial tumors (including breast, prostate, colon, ovarian, gastric and lung), cancer-induced asthenia (fatigue), irritable bowel syndrome, Crohn's disease, gastric ulceritis, and gallstones, and HIV infection, other infectious diseases, drug-induced lipodystrophy, and proliferative diseases such as psoriasis, wherein a therapeutically effective amount of a compound of structure I or a composition containing same is administered to a human patient in need of treatment.

In addition, in accordance with the present invention, a method is provided for improving coagulation homeostasis including reducing plasminogen activating inhibitor (PAI)-1 activity, reducing fibrinogen, and/or reducing platelet aggregation, and/or improving endothelial function, wherein a therapeutically effective amount of a compound of structure I or a composition containing same is administered to a patient in need of treatment.

In addition, in accordance with the present invention, a method is provided for treating cholesterol related diseases, diabetes and related diseases, cardiovascular diseases, cerebrovascular diseases as defined above and hereinafter and other diseases as set out above, wherein a therapeutically effective amount of a combination of a compound of structure I and a hypolipidemic agent, and/or lipid modulating agent and/or antidiabetic agent and/or cardiovascular agent, cerebrovascular agent, and/or other type of therapeutic agent, is administered to a patient in need of treatment.

In the above methods of the invention wherein a combination is administered, the compound of structure I will be employed in a weight ratio to the other therapeutic agent (depending upon its mode of operation) within the range from about 0.01:1 to about 500:1, preferably from about 0.5:1 to about 100:1.

DETAILED DESCRIPTION OF THE INVENTION

In accordance with the present invention, there is provided compounds useful in inhibiting the enzyme HMG-CoA reductase, which inhibitors are useful as hypocholesterolemic agents, dyslipidemic agents, hypolipidemic agents, hypotriglyceridemic agents, anti-Alzheimer's disease agents, and antiosteoporosis agents as well as other uses as described herein.

The term "coronary events" as employed herein refers to myocardial infarction, myocardial revascularization procedures, angina, cardiovascular death and acute coronary syndrome.

The term "cardiovascular diseases or events" as employed herein refers to atherosclerosis of the coronary arteries, myocardial infarction, including primary MI and secondary MI, recurrent myocardial infarction, angina pectoris (including stable and unstable angina), congestive heart failure, and sudden cardiac death.

The term "cerebrovascular diseases or events" as employed herein refers to cerebral infarction or stroke (caused by vessel blockage or hemmorage), or transient ischemia attack (TIA), syncope, atherosclerosis of the intracranial and/or extracranial arteries, and the like.

The term "cholesterol-related diseases" as employed herein refers to diseases involving elevated levels of LDL cholesterol, diseases involving regulation of LDL receptors, diseases involving reduced levels of HDL cholesterol, dyslipidemia, hyperlipidemia, elevated LDL Pattern B, elevated LDL Pattern A, hypercholesterolemia, hypo α-lipoproteinemia (low HDL cholesterol syndrome), hyperlipoproteinemia, elevated Lp(a) levels, hypertriglyceridemia, other aberrations of apolipoprotein B metabolism, heterozygous familial, presumed familial combined and non-familial (non-FH) forms of primary hypercholesterolemia (including Frederickson Types IIa and IIb), cholesterol ester storage disease, and cholesterol ester transfer protein disease, and related diseases.

The conditions, diseases, and maladies collectively referenced to as "Syndrome X" or Dysmetabolic Syndrome (as detailed in Johanson, *J. Clin. Endocrinol. Metab.*, 1997, 82, 727-734, and other publications) include hyperglycemia and/or prediabetic insulin resistance syndrome, and is characterized by an initial insulin resistant state generating hyperinsulinemia, dyslipidemia, and impaired glucose tolerance, which can progress to Type II diabetes, characterized by hyperglycemia, which can progress to diabetic complications.

The term "diabetes and related diseases" refers to Type II diabetes, Type I diabetes, impaired glucose tolerance, obesity, hyperglycemia, Syndrome X, dysmetabolic syndrome, diabetic complications and hyperinsulinemia.

The conditions, diseases and maladies collectively referred to as "diabetic complications" include retinopathy, neuropathy and nephropathy, and other known complications of diabetes.

The term "other type(s) of therapeutic agents" as employed herein refers to one or more antidiabetic agents (other than compounds of formula I), one or more anti-obesity agents, and/or one or more lipid-lowering agents, one or more lipid modulating agents (including anti-atherosclerosis agents), other types of anti-atherosclerosis agents, and/or one or more antiplatelet agents, one or more agents for treating hypertension, one or more anti-cancer drugs, one or more agents for treating arthritis, one or more anti-osteoporosis agents, one or more agents for treating immunomodulatory diseases, and/or one or more agents for treating anorexia nervosa.

The term "lipid-modulating" agent as employed herein refers to agents which lower LDL and/or raise HDL and/or lower triglycerides and/or lower total cholesterol and/or other known mechanisms for therapeutically treating lipid disorders.

The term "other types of anti-atherosclerosis agents" as employed herein refers to conventional anti-atherosclerosis agents including lipoxygenase inhibitors, ACAT inhibitors, PPARα agonists, dual PPARα/γ agonists, CETP inhibitors, antioxidants, PPAR δ agonists, phospholipase inhibitors including PLA-2 inhibitors and/or other known anti-atherosclerotic agents.

The terms pharmaceutically acceptable "salt" and "salts" refer to basic salts formed with inorganic and organic bases. Such salts include ammonium salts; alkali metal salts, such as lithium, sodium and potassium salts; alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Nontoxic, pharmaceutically acceptable salts are preferred, although other salts are also useful, e.g., in isolating or purifying the product. Preferred are sodium and calcium salts.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methanesulfonic acid or p-toluenesulfonic acid.

Where the compounds of structure I are in acid form they may form a pharmaceutically acceptable salt such as alkali metal salts such as lithium, sodium or potassium, alkaline earth metal salts such as calcium or magnesium as well as zinc or aluminum and other cations such as ammonium or choline, amino acid salts such as lysine (D or L), amine salts such as diethanolamine, ethylenediamine, t-butylamine, t-octylamine, tris-(hydroxymethyl)aminomethane (TRIS), N-methyl glucosamine (NMG), triethanolamine, dicyclohexylamine, methylamine and dehydroabietylamine.

Following are definitions of various groups which may be substituted with 1 to 4 or more substituents. It will be understood that the various substituents may be the same or different at each occurrence. These substituents may occur at any place and in any combination that provides a stable compound.

Unless otherwise indicated, the term "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Lower alkyl refers to such groups containing 1-6 carbon atoms. Unless specified otherwise, alkyl groups may be optionally substituted with 1 to 4 substituents. The substituents include halo, for example F, Br, Cl or I or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, cycloheteroalkyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl and/or alkylthio, $OR_{14}$, alkyl which may be substituted with one or more occurrences of $R_{15}$, alkenyl which may be substituted with one or more occurrences of $R_{15}$,
alkynyl which may be substituted with one or more occurrences of $R_{15}$,
cycloalkyl which may be substituted with one or more occurrences of $R_{15}$,
aryl which may be substituted with one or more occurrences of $R_{15}$,
heterocyclo which may be substituted with one or more occurrences of $R_{15}$,
$SR_{14}$,
$SO_2R_{14}$,
$COOR_{14}$,
$C(O)R_{14}$,
$CONR_{16}R_{17}$,
$SO_2NR_{16}R_{17}$,
$SO_2N(H)C(O)R_{14}$,
$SO_2N(H)CO_2R_{14}$, whererin $R_{14}$ is not H,
$NR_{16}R_{17}$,
$N(R_{16})SO_2R_{17}$,
$N(R_{16})C(O)_mR_{17}$ (m=1,2),
$N(R_{16})C(O)NR_{17}R_{18}$,
$N(R_{16})SO_2NR_{17}R_{18}$,
$OC(O)R_{14}$,
$OC(O)OR_{14}$,
$OC(O)NR_{17}R_{18}$,
$C(O)N(H)SO_2NR_{17}R_{18}$,
$C(O)N(H)SO_2R_{17}$,
oxo (or keto, i.e. =O),
thioxo (i.e., =S),
imino (i.e., =$NR_{19}$),
$NR_{19}$—$C(=NR_{20})R_{21}$,
$NR_{19}$—$C(=NR_{20})NR_{21}R_{22}$,
$C(=NR_{19})NR_{20}R_{21}$,
$OC(=NR_{19})NR_{20}R_{21}$,
$OC(=NR_{19})R_{20}$,
$C(=NR_{19})R_{20}$,
$C(=NR_{19})OR_{14}$, $R_{14}$ is selected from H, $C_1$-$C_8$ alkyl, $C_2$-$C_8$ alkenyl, $C_2$-$C_8$ alkynyl, $C_3$-$C_8$ cycloalkyl, $C_6$-$C_{10}$ aryl, or $C_1$-$C_9$ heterocyclo each of which may be substituted with 1 to 3 independent occurrences of $R_{15}$, $R_{16}$, $R_{17}$, and $R_{18}$ are independently selected from $C_1$-$C_8$ alkyl, $C_2$-$C_8$ alkenyl, $C_2$-$C_8$ alkynyl, $C_3$-$C_8$ cycloalkyl, $C_6$-$C_{10}$ aryl, or $C_1$-$C_9$ heterocyclo each of which may be substituted with 1 to 3 independent occurrences of $R_{15}$, or $R_{16}$ and $R_{17}$, or $R_{16}$ and $R_{18}$ or $R_{17}$ and $R_{18}$ may be joined by an alkylene or an alkenylene chain to form a 5- to 8-membered heterocyclo ring which is defined as for heterocyclo wherein the substituents may be one or more occurrences of $R_{15}$, $R_{19}$, $R_{20}$, $R_{21}$, or $R_{22}$ are indpendently selected from H, nitro, cyano, OH, O($C_1$-$C_6$ alkyl), $C(O)R_{14}$, $C(O)NR_{16}R_{17}$, $CO_2R_{14}$ (with the proviso that $R_{14}$ is not H), $SO_2R_{14}$, $SO_2NR_{16}R_{17}$, $C_1$-$C_8$ alkyl, $C_2$-$C_8$ alkenyl, $C_2$-$C_8$ alkynyl, $C_3$-$C_8$ cycloalkyl, $C_6$-$C_{10}$ aryl, or $C_1$-$C_9$ heterocyclo or $R_{19}$ and $R_{20}$ or $R_{19}$ and $R_{21}$ or $R_{19}$ and $R_{22}$ or $R_{20}$ and $R_{21}$ or $R_{20}$ and $R_{22}$ or $R_{21}$, and $R_{22}$ may be joined by an alkylene or alkenylene chain to form a 5-8 membered ring that may be optionally substituted with one or more occurrences of $R_{15}$.

$R_{15}$ is selected from
halogen,
nitro,
cyano,
$OR_{24}$,
alkyl optionally substituted with halogen,
cycloalkyl optionally substituted with halogen,
aryl optionally substituted with halogen, hydroxy, nitro, methoxy, trifluoromethyl, cyano, carbomethoxy, $CONH_2$, or CHO,
heterocyclo optionally substituted with halogen, hydroxy, nitro, methoxy, trifluoromethyl, cyano, carbomethoxy, $CONH_2$, or CHO,
$SR_{24}$,
$CO_2R_{24}$,
$C(O)R_{24}$,
$CONR_{25}R_{26}$,
$SO_2NR_{25}R_{26}$,
$NR_{25}R_{26}$,
$N(R_{25})SO_2R_{26}$,
$N(R_{25})C(O)_mR_{26}$ (m=1,2),
$N(R_{25})C(O)NR_{26}R_{27}$,
$N(R_{25})SO_2NR_{26}R_{27}$,
$OC(O)R_{24}$,
$OC(O)OR_{24}$,
$SO_2R_{24}$,
$SO_2N(H)C(O)R_{24}$,
$SO_2N(H)CO_2R_{24}$ wherein $R_{24}$ is not H,
$C(O)N(H)SO_2NR_{25}SR_{26}$,
$C(O)N(H)SO_2R_{24}$,
$OC(O)NR_{25}R_{26}$,
$NR_{28}$—$C(=NR_{29})R_{30}$,
$NR_{28}$—$C(=NR_{29})OR_{24}$,
$NR_{28}$—$C(=NR_{29})NR_{30}R_{31}$,
$C(=NR_{28})NR_{29}R_{30}$,
$OC(=NR_{28})R_{29}$,
$OC(=NR_{28})NR_{29}R_{30}$,
$C(=NR_{28})OR_{24}$, $R_{24}$ is selected from unsubstituted alkenyl, unsubstituted alkynyl, unsubstituted cycloalkyl, unsubstituted aryl, unsubstituted heterocyclo, $R_{25}$, $R_{26}$ and $R_{27}$ are selected from unsubstituted alkyl, unsubstituted alkenyl, unsubstituted alkynyl, unsubstituted cycloalkyl, unsubstituted aryl, unsubstituted heterocyclo, or $R_{25}$ and $R_{26}$ or $R_{25}$ and $R_{27}$ or $R_{26}$ and $R_{27}$ may be joined by an alkylene or alkenylene chain to form a 5-8 membered unsubstituted heterocyclo ring, and $R_{28}$, $R_{29}$, $R_{30}$, $R_{31}$ are selected from nitro, cyano, unsubstituted alkyl, unsubstituted alkenyl, unsubstituted alkynyl, unsubstituted cycloalkyl, unsubstituted aryl, unsubstituted heterocyclo, or $R_{28}$ and $R_{29}$, or $R_{28}$ and $R_{30}$ or $R_{28}$ and $R_{31}$ or $R_{29}$ and $R_{30}$ or $R_{29}$ and $R_{31}$ or $R_{30}$ and $R_{31}$ may be joined by an alkylene chain to form a 5-to 8-membered unsubstituted heterocyclo ring.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

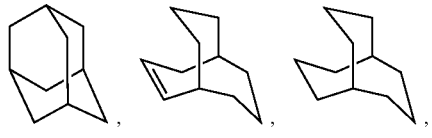

-continued

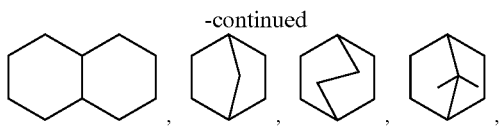

any of which groups may be optionally substituted with 1 to 4 substituents, which may be the same or different at each occurrence, such as halogen, alkyl, alkoxy, hydroxy, aryl, aryloxy, arylalkyl, cycloalkyl, alkylamido, alkanoylamino, oxo, acyl, arylcarbonylamino, heteroaryl, cycloheteroalkyl, amino, alkylamino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "alkanoyl" or "alkylcarbonyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio and/or any of the alkyl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted with 1 or 2 substituents as defined above for "alkyl", such as, for example, alkyl, halo, hydroxy, alkoxy and/or cycloalkyl.

Where alkenyl groups as defined above and alkynyl groups as defined above, respectively, have single bonds for attachment at two different carbon atoms, they are termed "alkenylene groups" and "alkynylene groups", respectively, and may optionally be substituted with 1 or 2 substituents as defined above for "alkenyl" and "alkynyl".

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

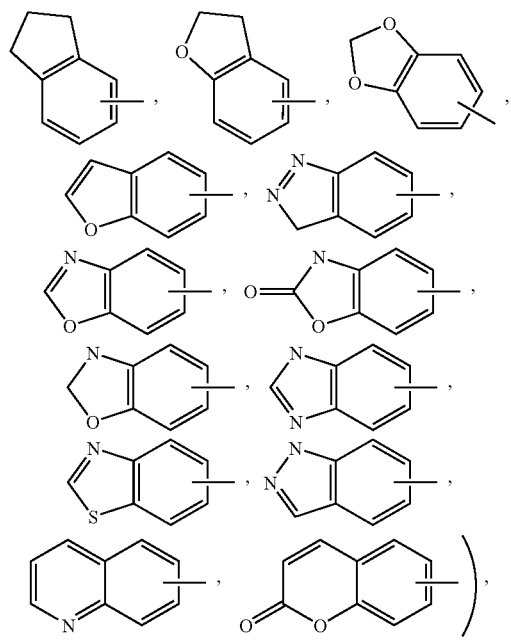

and may be optionally substituted through available carbon atoms with 1, 2, or 3 groups selected from hydrogen, halo, alkyl, haloalkyl, alkoxy, halophenyl, benzoyloxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, alkanoyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid and/or any of the substituents for alkyl as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", "alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a $$\text{carbonyl} \begin{pmatrix} O \\ \parallel \\ C \end{pmatrix} \text{group};$$

examples of acyl groups include any of the $R_1$ or $R_4$ groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_r$ (where r is 1, 2 or 3), such as

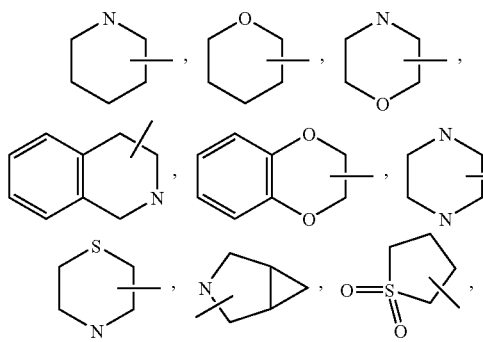

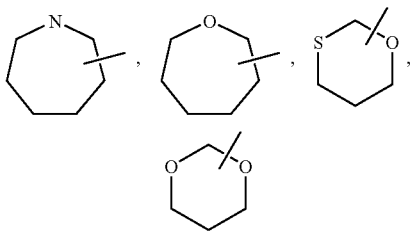

and the like. The above groups may include 1 to 4 substituents such as alkyl, halo, oxo and/or any of of the alkyl substituents set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the substituents set out above for alkyl. Examples of heteroaryl groups include the following:

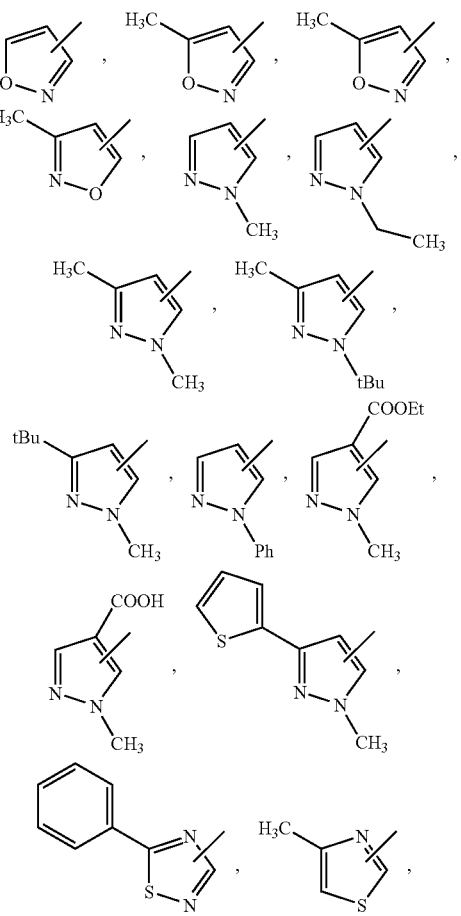

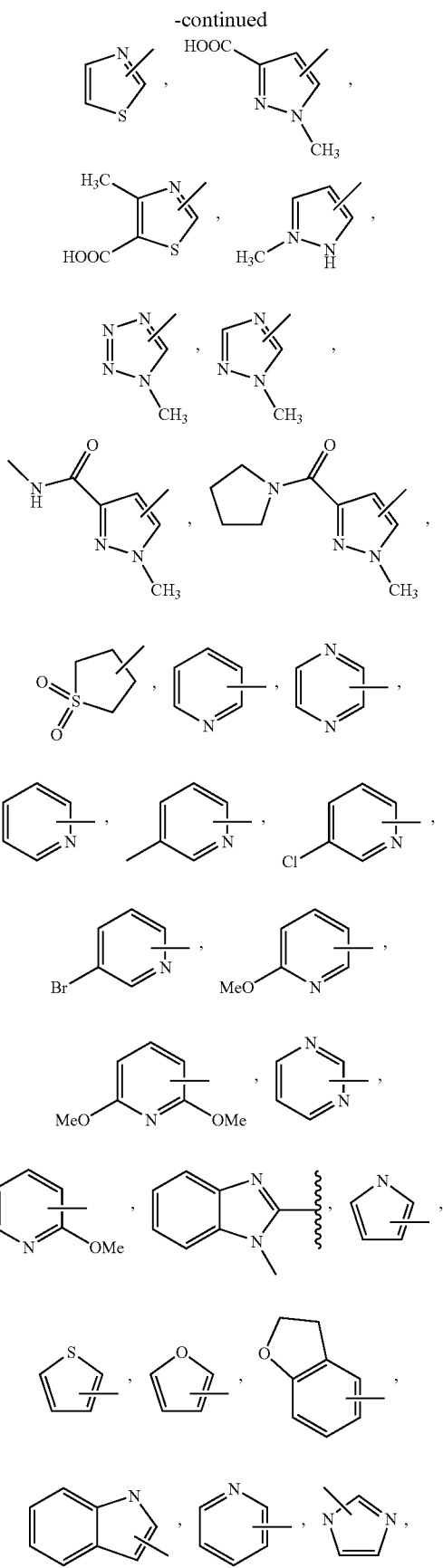
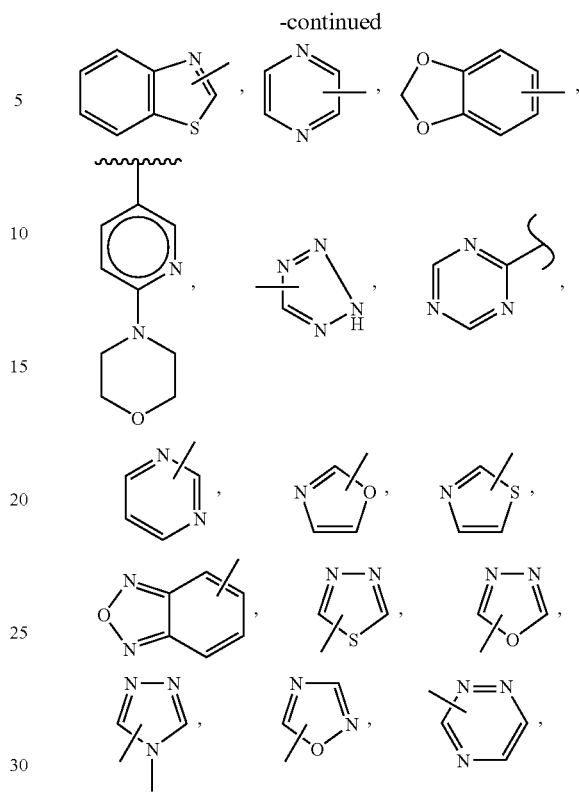

and the like.

The term "cycloheteroalkylalkyl" as used herein alone or as part of another gorup refers to cycloheteroalkyl groups as defined above linked through a C atom or heteroatom to a $(CH_2)_r$ chain.

The term "heteroarylalkyl" or "heteroarylalkenyl" as used herein alone or as part of another group refers to a heteroaryl group as defined above linked through a C atom or heteroatom to a $-(CH_2)_r-$ chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "heterocyclo" or "heterocyclyl" as used herein refers to heteroaryl and cycloheteroalkyl.

The term "polyhaloalkoxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

As defined above, alkyl, alkenyl, alkynyl, cycloalkyl, and heterocyclo groups may be attached through one or more single bonds to one or more attachement atoms. In addition, these groups may be attached by double bonds to attachement atoms, and these groups may be referred to as 'alkylidene', 'alkenylidene', 'alkynylidene', 'cycloalkylidene' or 'heterocyclidene' groups. Examples include methylidene (=CH2), ethylidene (=CHCH3), ethenylidene (=C=CH2), cyclohexylidene ( 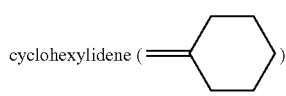 )

and 2-pyranylidene ( 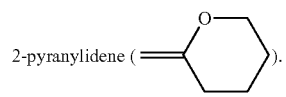 ).

These groups may be substitued as described above for alkyl, alkenyl, alkynyl, cycloalkyl, and heterocyclo.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The compounds of the present invention can have asymmetric centers at certain of the nitrogen atoms. Consequently, these isomers or mixtures thereof are part of the present invention.

The compounds of the present invention may also display other instances of chirality, such as atropoisomerism. Thus, these isomers or mixtures thereof are part of the invention.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like. In addition, prodrug esters which are known in the art for carboxylic and phosphorus acid esters such as methyl, ethyl, benzyl and the like are included herein.

Examples of such prodrug esters include

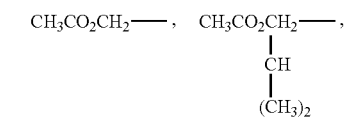

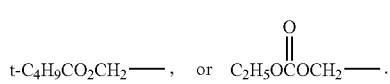

Other examples of suitable prodrug esters include

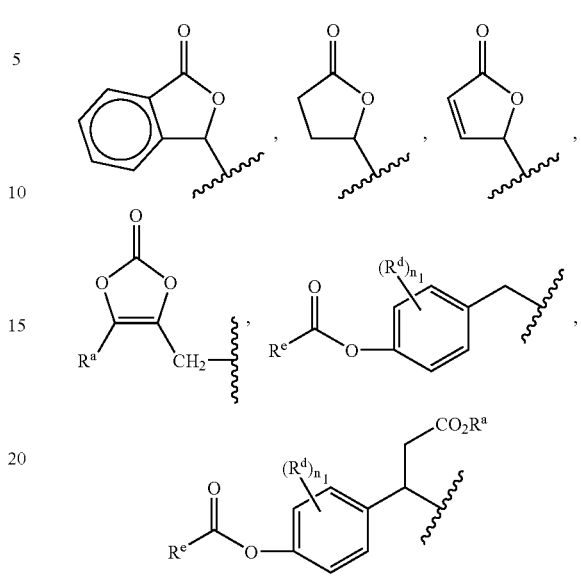

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

Compounds of the invention may be prepared by the following methods (Schemes 1-4).

SCHEME 1

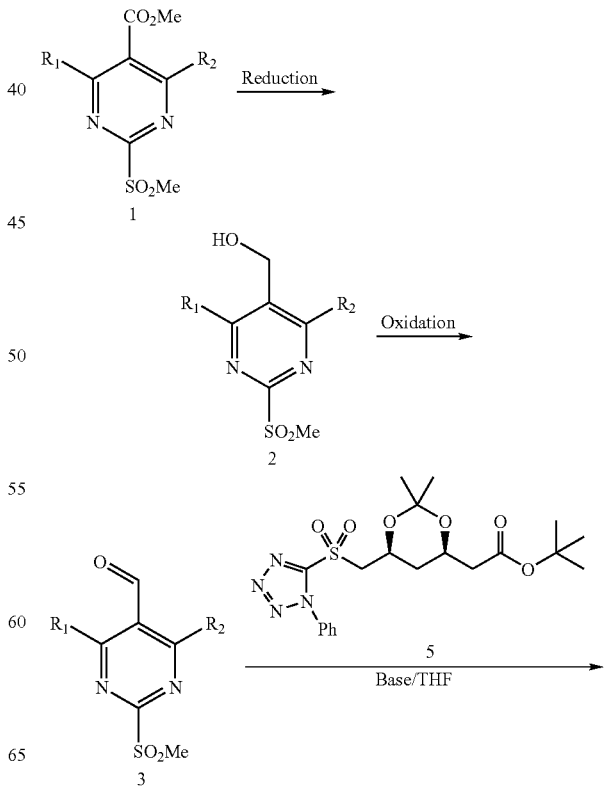

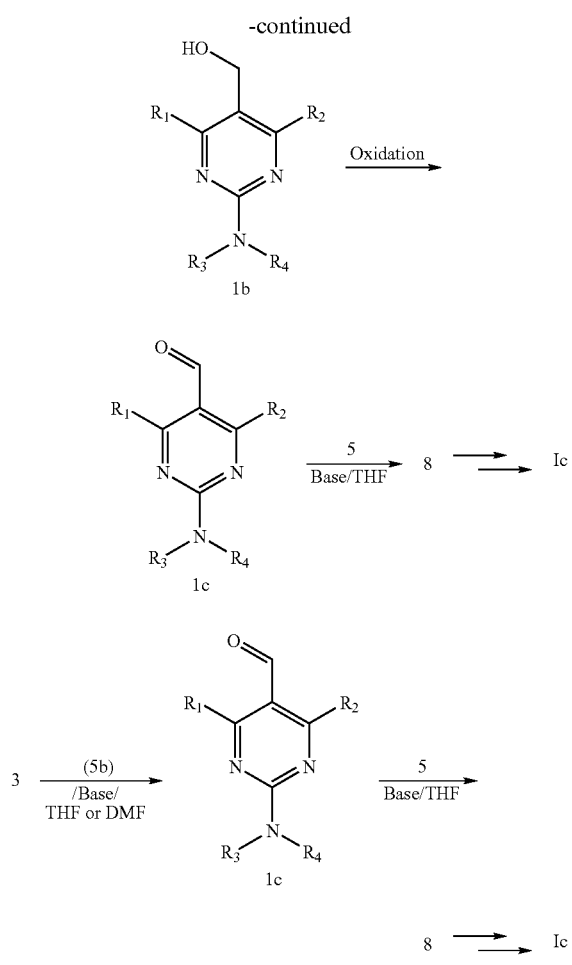

Scheme 1 outlines synthesis of the compounds of formula I where X=N. The previously known ester 1 (Masamichi Watanabe et al. Bioorganic & Medicinal Chemistry (1997), 5(2), 437-444; Eur. Pat. App. 1993, 18 pp. EP 521471) can be reduced by using DIBAL in toluene or methylene chloride to afford the alcohol 2. Compound 2 can be oxidized by using Dess-Martin's periodinane in methylene chloride or by using buffered bleach (NaOCl) in the presence of catalytic amounts of TEMPO free radical and potassium bromide in methylene chloride or ethyl acetate to afford aldehyde 3. Compound 3 can be converted to the key intermediate olefin 4 by reaction with the previously known sulfone 5 (Brodfuehrer, Paul R. et al. PCT Int. Appl. (2002), WO 0298854) and an organic base such as lithium, sodium or potassium bistrimethylsilyl amide. Treatment of compound 4 with an aryl amine, a cycloheteroalkylamine or a heteroarylamine 5a in the presence of a base such as lithium, sodium or potassium bistrimethylsilyl amide in THF or DMF affords 6. Compounds of formula 6 can be converted to certain compounds of the formula I ($R_4$=H, compound Ib) by treatment with an aqueous protic acid such as hydrochloric acid, sulfuric acid or p-toluenesulfonic acid to give Ia followed by saponification with an aqueous base such as sodium hydroxide to give Ib.

Alternatively, 6 can be converted to compounds of the formula I ($R_4$ is other than H, such as alkyl, alkylsulfonyl, alkanoyl, alkoxycarbonyl etc., compound Ic) by an initial treatment with a base such as lithium bis-trimethylsilylamide followed by treatment with $R_4$Hal (7) such as the corresponding alkyl halides, sulfonyl halides/anhydrides, acyl halides/anhydrides and alkyl chloroformates and the like to afford 8. Removal of the acetonide group and saponification as described above affords compounds of the formula Ic. Ic can be converted to the free acid Ic' by treating the salt Ic with an acid, preferably a mineral acid, such as HCl or $H_2SO_4$.

Alternatively, compound 4 can be converted directly to compound 8 by treatment with a preassembled amine $R_3R_4$NH (compound 5b) and a base such as lithium bistrimethylsilylamide and the like in THF or DMF. Removal of the acetonide group and saponification as described above affords compounds of the formula Ic.

Alternatively, compounds of formula Ic can be prepared from intermediates 1 or 3 as outlined in Scheme 1.

Alternatively, compounds 6 or 8 can be converted to the lactones Id or Ie, respectively, by reaction with an acid such as trifluroracetic acid in methylene chloride or chloroform which can be converted to the compounds of formula I (compounds Ic or Ic) by treatment with aqueous sodium hydroxide (Scheme 2).

SCHEME 2

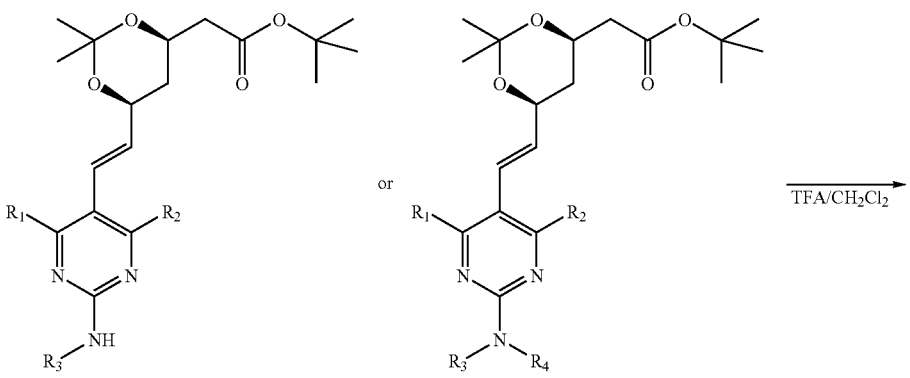

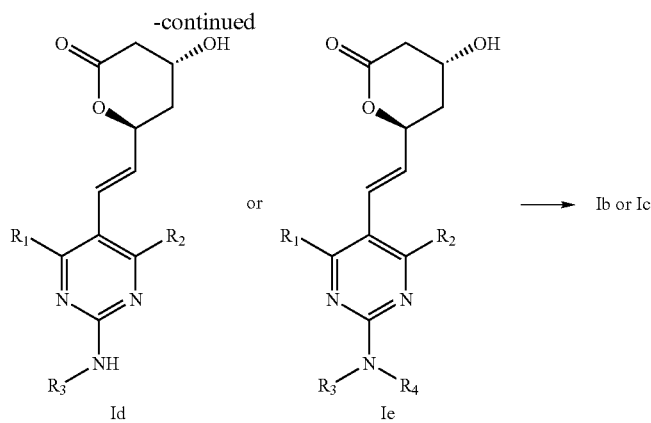

Certain compounds of the formula I where X=CR₅ can be prepared from the previously known intermediate 9 (Huebsch, Walter et al. Ger. Offen. (1992), DE 4023308; Huebsch, Walter et al. Eur. Pat. Appl. (1992), EP 465970) as described in Scheme 3. Lithium aluminum hydride reduction of 9 affords the benzylic alcohol 10 which can be further reduced to give 11 (R₅=methyl) using palldium on carbon under hydrogen in the presence of trifluoroacetic acid in ethanol. Other intermediates containing R₅ groups as described for formula I may be prepared from intermediate 10 or its protected analogs using common transformations known in the art, for example, oxidation, alkylation, displacement, addition and the like.

The aminopyridine 11 may be converted to the fluoropyridine 12 by treatment with sodium nitrite and tetrafluoroboric acid in water. Treatment of 12 with a heterocyclic amine R₃NH₂ (compound 5a) in the presence of a base such as lithium, sodium or potassium bistrimethylsilylamide in THF or DMF affords 13. Compound 13 can be converted to the alcohol 14 via reduction with a hydride reducing agent such as DIBAL. Oxidation of the alcohol 14 to the aldehyde 15 may be accomplished by using NaOCl in the presence of catalytic amounts of KBr and TEMPO in EtOAc or methylene chloride or by using Dess-Martin's periodinane in methylene chloride. Treatment of 15 with BOC anhydride in the presence of DMAP affords compound 16 which may be converted to the olefin 17 via treatment with the sulfone 5 (see Scheme 1) in the presence of a strong base such as lithium, sodium or potassium bistrimethylsilylamide. Treatment of 17 with an acid such as trifluoroacetic acid (TFA) in solvents such as methylene chloride or chloroform affords the lactone If which can be converted to the corresponding salt Ig. Ig may be converted to the corresponding free acid by treating Ig with an acid such as HCl or H₂SO₄.

Alternatively, compound 12 can be converted to 13a which can be converted to compounds of formula Ih where R₄ is other than H via reduction, oxidation, olefination and deprotection.

Certain compounds of formulae If, Ig and Ih (where R₅=H) can also be prepared from compound 9 via selective hydrolysis of the sterically less hindered ethyl ester followed by decarboxylation of the resulting acid 9a using methods and reagents known in the art (e.g. heating with Cu powder/quinoline, U.S. Pat. No. 4,405,552, 20 Sep. 1983). The resulting intermediate 9b can be used to synthesize compounds of formulae If, Ig or Ih (where R₅=H) in a manner described for intermediate 11.

Certain compounds of formula I where X=CR₅ and R₅ is alkoxyalkyl (i.e. compounds of formula Ii) can also be prepared from compound 9 as outlined in Scheme 3. Thus, conversion of the amino group of 9 to a fluoro group can be achieved by using sodium nitrite and tetrafluoroboric acid to afford 9c. Coupling of 9c with 5b can afford 9d which can be reduced using diborane to give the alcohol 9e. Treatment of 9e with alkyl halides, alkyl triflates and the like under basic conditions (NaH, LiH and the like) in THF or DMF can afford 9f. Conversion of 9f to the compounds of formula Ii can be carried out via reduction, oxidation, olefination and deprotection as described before.

SCHEME 3

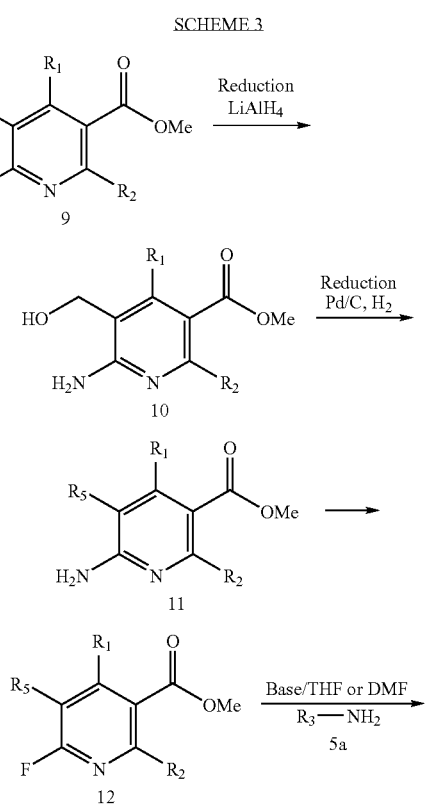

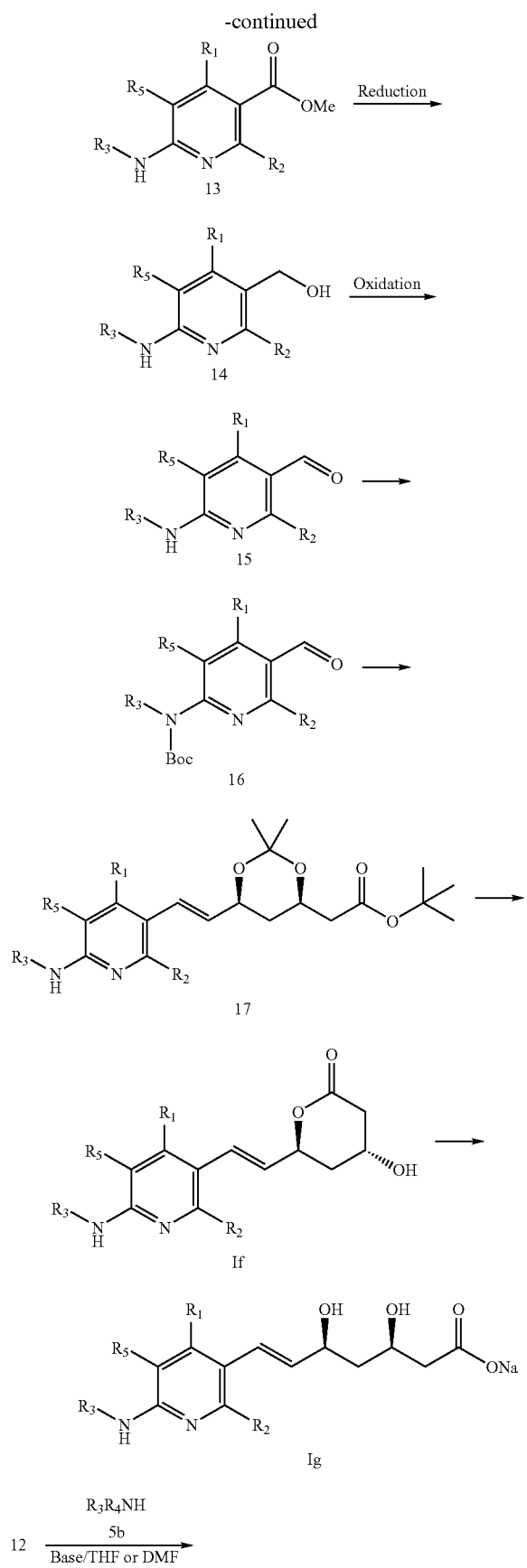
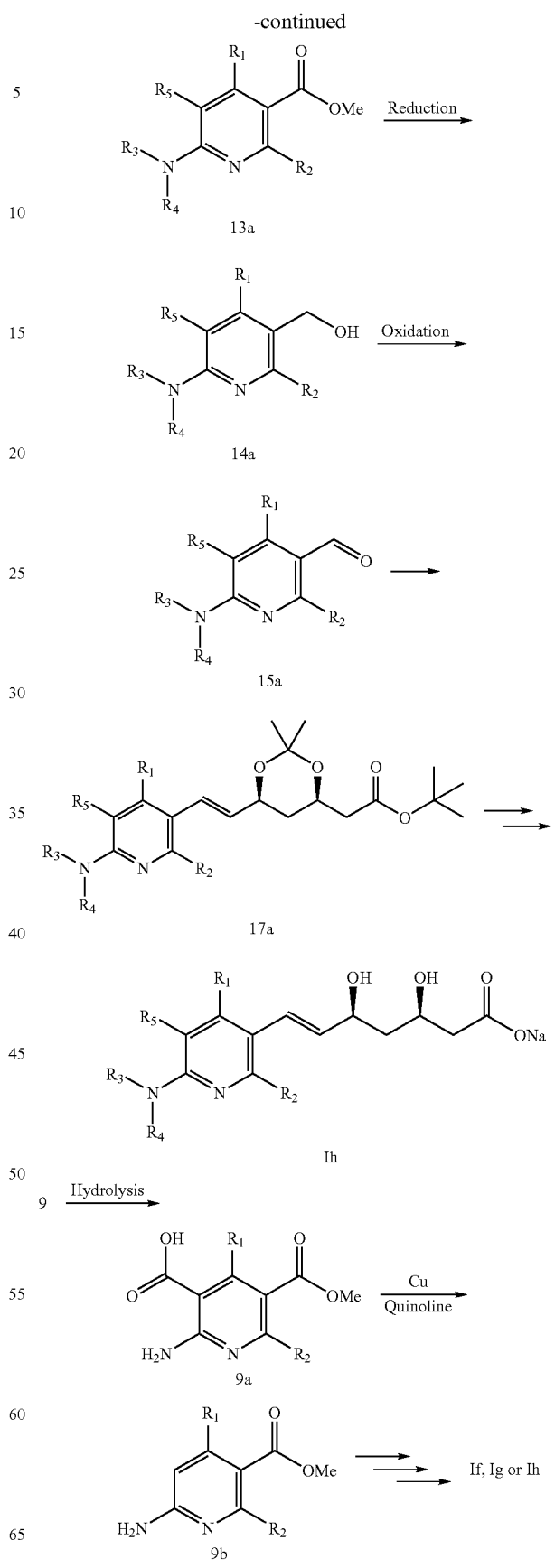

-continued
9 →
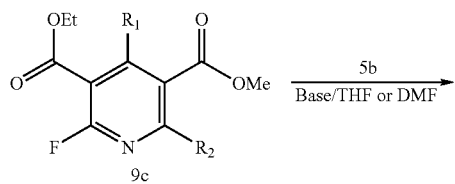
9c
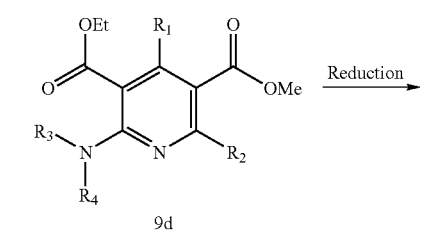
9d
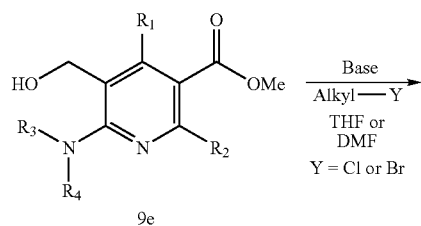
9e
-continued
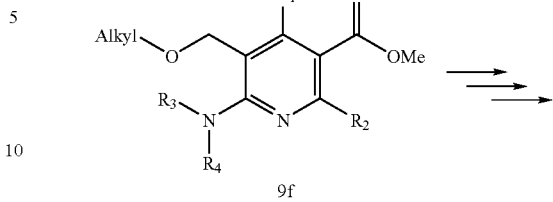
9f
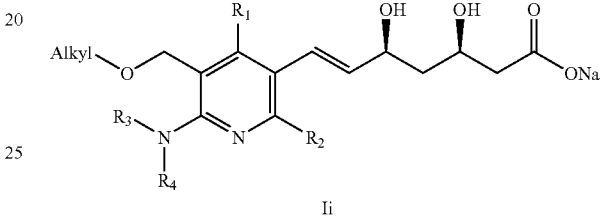
Ii
Certain compounds of formula I where ⫽ is —CH₂CH₂— can be prepared from the corresponding unsaturated intermediates or other unsaturated compounds of formula I (where ⫽ is ⫽) via catalytic hydrogenation followed by treatment with acids and/or aqueous base as shown in Scheme 4.
SCHEME 4
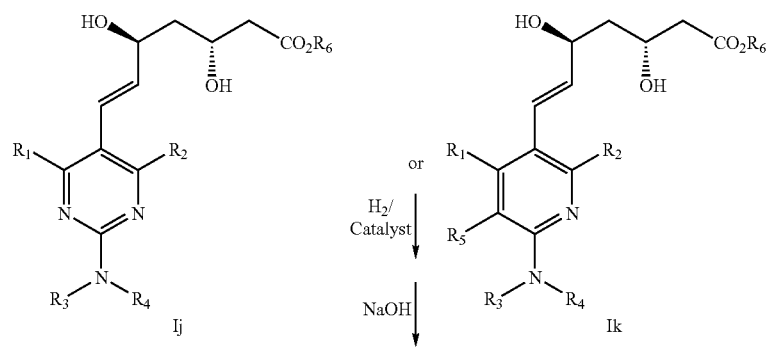

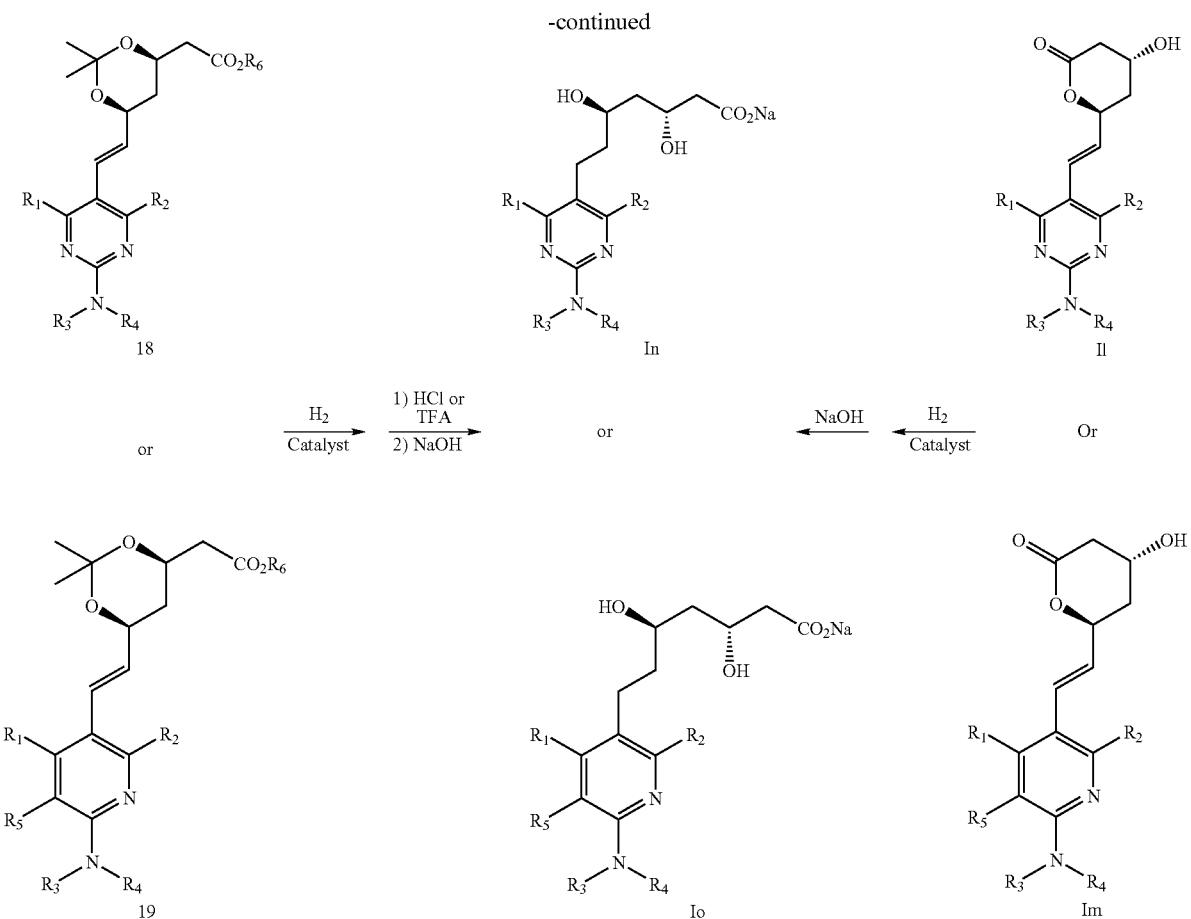

Compounds containing dihydroxy acid HMG-CoA binding domain side chains may be prepared in homochiral form, which is preferred, or may be prepared as racemic mixtures (3S*, 5R*) and may later be resolved to obtain the 3S, 5R isomer.

The following intermediates are novel compounds and form part of the present invention:

intermediates 1b, 1c, 2 to 4, 6, 8, 9a to 9f, 13a, 14a, 15a, 17a and 11 to 19 which may be represented by the following formulae:

A.

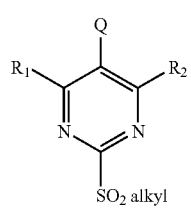

Q is HOCH$_2$— or

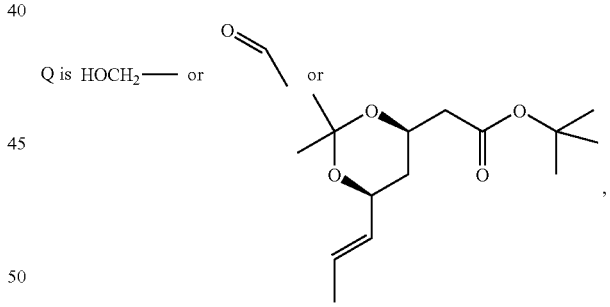

B.

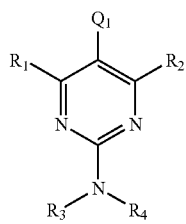

where R$_1$ and R$_2$ are the same or different and are independently selected from alkyl, alkoxyalkyl, arylalkyl, cycloalkyl, alkenyl, cycloalkenyl, aryl, heteroaryl or cycloheteroalkyl; and where R$_1$ and R$_2$ are as defined above, R$_3$ is aryl, heteroaryl, cycloalkyl or heterocycloalkyl;

R$_4$ is H, alkyl, cycloalkyl, haloalkyl, alkoxyalkyl, alkylthioalkyl, alkylsulfonyl, arylsulfonyl, alkoxycarbonyl, aryloxycarbonyl, heteroaryloxycarbonyl, alkylaminocarbonyl, arylaminocarbonyl, heteroarylaminocarbonyl, alkylaminosulfonyl, acyl, arylcarbonyl, heteroarylcarbonyl or heteroarylsulfonyl; and $Q_1$ is $HOCH_2$— or 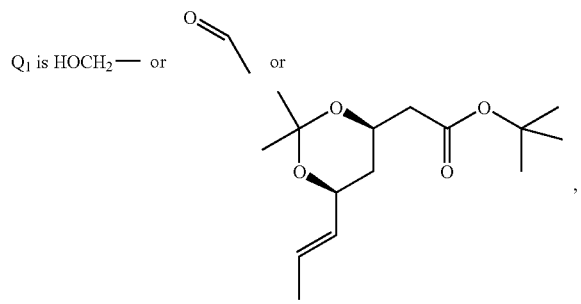,

C.

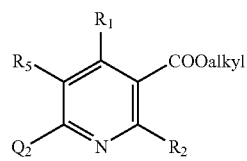

where $R_1$ and $R_2$ are as defined above, and $Q_2$ is $H_2N$, F, $R_3HN$—, or $R_3R_4N$—, $R_5$ is —COOH, lower alkyl, H, COOalkyl, —CH$_2$OH or alkylO—.

D.

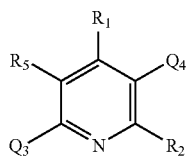

where $R_1$, $R_2$ and $R_5$ are as defined above and $Q_3$ is $R_3HN$—, $R_3R_4N$—,

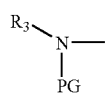

(where PG is a protecting group such as

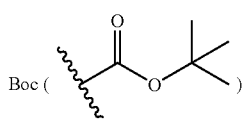

or

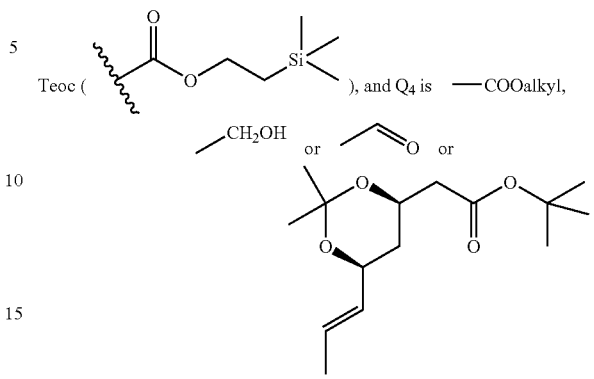), and $Q_4$ is —COOalkyl,

The compounds of the invention are inhibitors of 3-hydroxy-3-methyl-glutaryl coenzyme A (HMG-CoA) reductase and thus are useful in inhibiting cholesterol biosynthesis and/or in lowering triglycerides, in a manner similar to atorvastatin, pravastatin, simvastatin, lovastatin, cerivastatin, rosuvastatin, fluvastatin, pitavastatin, and the like.

A further aspect of the present invention is a pharmaceutical composition containing at least one of the compounds of formula I of the present invention in association with a pharmaceutical vehicle or diluent. The pharmaceutical composition can be formulated employing conventional solid or liquid vehicles or diluents and pharmaceutical additives of a type appropriate to the mode of desired administration. The compounds can be administered by an oral route, for example, in the form of tablets, capsules, granules or powders, or they can be administered by a parenteral route in the form of injectable preparations. Such dosage forms contain from 0.1 to 1500 mg of active compound per dosage, for use in the treatment. The dose to be administered depends on the unitary dose, the symptoms, and the age and the body weight of the patient.

The compounds of the present invention can be administered in a similar manner as known compounds suggested for use in inhibiting cholesterol biosynthesis, such as pravastatin, lovastatin, simvastatin, rosuvastatin, atorvastatin, cerivastatin, fluvastatin, pitavastatin, and the like, in mammalian species such as humans, dogs, cats and the like. Thus, the compounds of the invention may be administered in an amount from about 0.1 to 500 mg in a single dose or in the form of individual doses from 1 to 4 times per day, preferably 0.5 to 200 mg daily or in sustained release form.

The HMG CoA reductase inhibitors of formula I may be employed in combination with all therapeutic agents which are useful in combination with HMG CoA reductase inhibitors.

Thus, where desired, the compounds of structure I may be used in combination with one or more hypolipidemic agents or lipid-lowering agents, or lipid agents, or lipid modulating agents, and/or one or more other types of therapeutic agents including antidiabetic agents, anti-obesity agents, antihypertensive agents, platelet aggregation inhibitors, anti-Alzheimer's agents, anti-dementia agents, anti-osteoporosis agents, and/or hormone replacement therapeutic agents, and/or other therapeutic agents, and/or other cardiovascular agents (including anti-anginal agents, anti-arrhythmic agents, anti-atherosclerosis agents, anti-inflammatory agents, anti-platelet agents, anti-heart failure agents), anti-cancer agents, anti-infective agents, hormone replacement agents, growth hormone secretagogues, selective androgen receptor modulators (SARMs), and/or other therapeutic agents which may be administered orally in the same dosage form or in a separate oral dosage form, or by injection.

The hypolipidemic agent or lipid-lowering agent or other lipid agent or lipid modulating agent which may be optionally employed in combination with the compounds of formula I of the invention may include 1,2,3 or more MTP inhibitors, HMG CoA reductase inhibitors, squalene synthetase inhibitors, PPAR α agonists, PPAR dual α/γ agonists, PPAR δ agonists, fibric acid derivatives, ACAT inhibitors, lipoxygenase inhibitors, cholesterol absorption inhibitors, ileal Na+/bile acid cotransporter inhibitors, upregulators of LDL receptor activity, cholesteryl ester transfer protein inhibitors, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875, 5,885,983 and U.S. Pat. No. 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-Trifluoroethoxy)benzoyl]amino]-1-piperidinyl]butyl]-N-(2,2,2-trifluoroethyl)-9H-fluorene-9-carboxamide

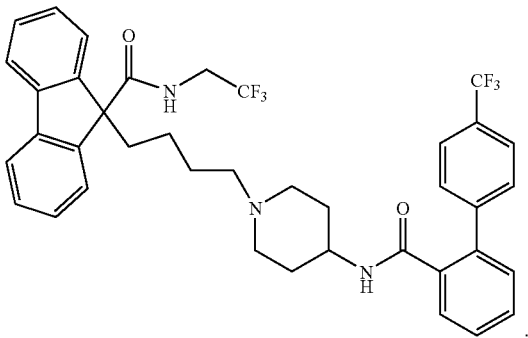

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinyl-methyl)phosphonates as well as other known squalene synthetase inhibitors, for example, as disclosed in U.S. Pat. No. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, fenofibrate, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277, 082 and CL-283,546 (disubstituted urea derivatives), nicotinic acid (ER niacin, Niaspan), acipimox, acifran, neomycin, p-aminosalicylic acid, aspirin, poly (diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, Drugs of the Future 24, 9-15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137 (1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 (ezetimibe) as well as those disclosed in Atherosclerosis 115, 45-63 (1995) and J. Med. Chem. 41, 973 (1998).

The other lipid agent or lipid-modulating agent may be a cholesteryl transfer protein inhibitor (CETP) such as Pfizer's CP-529,414 (torcetrapib) as well as those disclosed in WO/0038722 and in EP 818448 (Bayer) and EP 992496, and Pharmacia's SC-744 and SC-795 as well as CETi-1 and JTT-705.

The hypolipidemic agent may be an ileal Na+/bile acid cotransporter inhibitor such as disclosed in Drugs of the Future, 24, 425-430 (1999).

The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201;

a beta-lactam cholesterol absorption inhibitor such as disclosed in EP 675714;

an HDL upregulator such as an LXR agonist, a PPAR α-agonist and/or an FXR agonist;

an α-glucosidase inhibitor, an aldose reductase inhibitor and/or an LDL catabolism promoter such as disclosed in EP 1022272;

a sodium-proton exchange inhibitor such as disclosed in DE 19622222;

an LDL-receptor inducer or a steroidal glycoside such as disclosed in U.S. Pat. No. 5,698,527 and GB 2304106;

an anti-oxidant such as beta-carotene, ascorbic acid, x-tocopherol or retinol as disclosed in WO 94/15592 as well as Vitamin C and an antihomocysteine agent such as folic acid, a folate, Vitamin B6, Vitamin B12 and Vitamin E;

isoniazid as disclosed in WO 97/35576;

a cholesterol absorption inhibitor, an HMG-CoA synthase inhibitor, or a lanosterol demethylase inhibitor as disclosed in WO 97/48701;

a PPAR δ agonist for treating dyslipidemia;

a PPAR α agonist for treating dyslipidemia;

a dual PPAR α/γ agonist such as muraglitazar (Bristol Myers-Squibb), tesaglitazar (AstraZeneca) or MK-767 (Merck/Kyorin/Banyu);

or a sterol regulating element binding protein-I (SREBP-1) as disclosed in WO 2000/050574, for example, a sphingolipid, such as ceramide, or neutral sphingomyelenase (N-SMase) or fragment thereof.

Preferred hypolipidemic agents are cholesterol absorption inhibitors such as ezetimibe, cholesterol ester transfer protein (CETP) inhibitors such as torcetrapib and JTT-705, dual PPAR α/δ agonists such as muraglitazar and tesaglitazar, as well as niacin and/or cholestagel.

The above-mentioned U.S. patents are incorporated herein by reference. The amounts and dosages employed will be as indicated in the Physician's Desk Reference and/or in the patents set out above or as otherwise known in the art.

The compounds of formula I of the invention will be employed in a weight ratio to the hypolipidemic agent (where present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent or other lipid agent or lipid modulating agent will be as disclosed in the various patents and applications discussed above.

The dosages and formulations for the other hypolipidemic agent or other lipid agent or lipid modulating agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 200 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The anti-atherosclerotic agent includes a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties," Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The antidiabetic agent which may be optionally employed in combination with the HMG-CoA reductase inhibitor of formula I may be 1,2,3 or more antidiabetic agents or antihyperglycemic agents including insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, aP2 inhibitors, PPAR α/γ dual agonists, dipeptidyl peptidase IV (DP4) inhibitors, SGLT2 inhibitors, glycogen phosphorylase inhibitors, and/or meglitinides, and/or glucagon-like peptide-1 (GLP-1), and/or a PTP-1B inhibitor (protein tyrosine phosphatase-1B inhibitor), as well as insulin and slow release insulin (Basulin™ (Flamel)).

The antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.05:1 to about 10:1.

The sulfonyl urea and PPAR γ agonists in amounts of less than about 150 mg oral antidiabetic agent may be incorporated in a single tablet with the compounds of structure I.

The compounds of structure I may also be employed in combination with a antihyperglycemic agent such as insulin or slow release insulin (Basulin™), or with glucagon-like peptide-1 (GLP-1) or mimetic such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (Amylin) and LY-315902 (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the PPAR anti-diabetic agent may be employed in amounts within the range from about 0.01 to about 2000 mg/day which may be administered in single or divided doses one to four times per day.

Where present insulin and other anti-diabetic agents as set out above may be employed in formulations, amounts and dosing as indicated by the Physician's Desk Reference.

Where present GLP-1 peptides or mimetics may be administered in oral buccal formulations, by nasal administration or parenterally as described in U.S. Pat. Nos. 5,346,701 (TheraTech), 5,614,492 and 5,631,224 which are incorporated herein by reference.

The antidiabetic agent or other lipid agent may also be a PPAR modulator such as a PPAR α/γ dual agonist such as tesaglitazar (Astra/Zeneca), muraglitazar (Bristol Myers-Squibb), MK-767 (Merck/Kyorin/Banyu), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998), and in U.S. application Ser. No. 09/664,598, filed Sep. 18, 2000, the disclosure of which is incorporated herein by reference, employing dosages as set out therein, which compounds designated as preferred are preferred for use herein.

The antidiabetic agent may be an SGLT2 inhibitor such as disclosed in U.S. Pat. Nos. 6,414,126 and 6,515,117, employing dosages as set out therein. Preferred are the compounds designated as preferred in the above patents.

The antidiabetic agent may be an aP2 inhibitor such as disclosed in U.S. Pat. No. 6,548,529, employing dosages as set out herein. Preferred are the compounds designated as preferred in the above patent.

The antidiabetic agent may be a DPP4 inhibitor such as disclosed in U.S. Pat. No. 6,395,767, U.S. Pat. No. 6,573,287, U.S. Pat. No. 6,395,767 (BMS-477118 (preferred), BMS-471211 and BMS 538,305), WO99/38501, WO99/46272, WO99/67279 (PROBIODRUG), WO99/67278 (PROBIODRUG), WO99/61431 (PROBIODRUG), NVP-LAF-237, NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38(36), 11597-11603, 1999, TSL-225 (tryptophyl-1,2,3,4-tetrahydro-isoquinoline-3-carboxylic acid (disclosed by Yamada et al, Bioorg. & Med. Chem. Lett. 8 (1998) 1537-1540, 2-cyanopyrrolidides and 4-cyanopyrrolidides as disclosed by Ashworth et al, Bioorg. & Med. Chem. Lett., Vol. 6, No. 22, pp 1163-1166 and 2745-2748 (1996) employing dosages as set out in the above references.

The meglitinide which may optionally be employed in combination with the compound of formula I of the invention may be repaglinide or Starlix® (Novartis), nateglinide (Novartis) or KAD1229 (PF/Kissei), with repaglinide being preferred.

The antidiabetic compound may be a melanocortin receptor agonist such as a spiropiperidine as disclosed in WO 99/64002.

The HMG CoA reductase inhibitor of formula I will be employed in a weight ratio to the meglitinide, PPAR modulator such as a PPAR γ agonist, PPAR α agonist, PPAR δ agonits or antagonist, PPAR α/γ dual agonist, aP2 inhibitor, DP4 inhibitor or SGLT2 inhibitor or other antidiabetic agent within the range from about 0.01:1 to about 100:1, preferably from about 0.05:1 to about 10:1.

The other type of therapeutic agent which may be optionally employed with the HMG CoA reductase inhibitor of formula I may be 1, 2, 3 or more of an anti-obesity agent including a beta 3 adrenergic agonist, a lipase inhibitor, a serotonin and/or dopamine modulator/mimic, norepinephrine (NE) modulator/mimic, an aP2 inhibitor, a thyroid receptor beta drug, a PTP-1B inhibitor, an anorectic agent, a PPAR modulator including PPAR γ antagonists, PPAR α agonists, PPAR δ antagonists, a CCKA agonist, a leptin inhibitor such as a leptin receptor activator, a neuropeptide Y antagonist, a melanocortin-4-receptor (MC4R) agonist, a CB-1 inverse agonist, a fatty acid oxidation upregulator or inducer (such as Famoxin® Genset), a 5-HT2c agonist, and an acetyl CoA carboxylase (ACC) inhibitor.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The neuropeptide Y antagonists which may be optionally employed in combination with a compound of formula I include those described in WO 0113917 (BMS) or in U.S. Pat. No. 6,218,408 (Synaptic) and in WO 0114376 (Banyu).

The lipase inhibitor which may be optionally employed in combination with a compound of formula I may be orlistat or ATL-962 (Alizyme), with orlistat being preferred.

The serotonin and dopoamine modulator/mimic and/or norepinephrine modulator/mimic which may be optionally employed in combination with a compound of formula I may be sibutramine.

The anorectic agent which may be optionally employed in combination with a compound of formula I may be topiramate, Axokine® (Regeneron) (anlogue of Ciliary Neurotrophic Factor) dexamphetamine, phentermine, phenylpropanolamine or mazindol, with dexamphetamine or topiramate being preferred.

The thyroid receptor beta compound which may be optionally employed in combination with a compound of formula I may be a thyroid receptor ligand as disclosed in WO97/21993 (U. Cal SF), WO99/00353 (KaroBlo), GB98/284425 (KaroBio), and U.S. Provisional Application No. 60/183,223 filed Feb. 17, 2000, with compounds of the KaroBio applications and the above U.S. provisional application being preferred.

Examples of the ACC inhibitors which may be employed include those described in WO 03/072197.

Examples of the CB-1 inverse agonists which may be employed include SR-141716 (Sanofi) and FLV-319 (Folvay).

Examples of the 5-HT2c agonists which may be employed include compounds as disclosed in WO 00/77010.

The CCKA agonists which may be employed herein include Glaxo-SmithKline's GI-181,771 and Sanofi's SR146,131.

The PTP-1B inhibitor which may be an anti-obesity and/or an antidiabetic agent include those disclosed in WO 99/585,521, WO 99/58518, WO 99/58522 and WO 99/61435.

The anti-obesity agent employed may also be Pfizer's P57 or CP-644,673 (licensed from Phytopharm).

The various anti-obesity agents described above may be employed in the same dosage form with the compound of formula I or in different dosage forms, in dosages and regimens as generally known in the art or in the PDR.

The antihypertensive agents which may be employed in combination with the HMG CoA reductase inhibitors of the invention include ACE inhibitors, angiotensin II receptor antagonists, MR agonist, NEP inhibitors such as candoxatril, NEP/ACE inhibitors, as well as calcium channel blockers (such as verapamil and amlodipine besylate), T-channel calcium antagonists (such as mibefradil), β-adrenergic blockers, diuretics, α-adrenergic blockers (such as doxazosin mesylate and terazosin HCl), dual action receptor antagonists (DARA), heart failure drugs such as digoxin, and other types of antihypertensive agents.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Preferred ACE inhibitors are captopril, fosinopril, enalapril, lisinopril, cetapril, cilazapril, indalapril, spirapril, perindopril, ceranapril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, 5,552,397, 5,504,080, 5,612,359, 5,525,723, European Patent Application 0599,444, 0481,522, 0599,444, 0595,610, European Patent Application 0534363A2, 534,396 and 534,492, and European Patent Application 0629627A2.

Preferred are those NEP/ACE inhibitors and dosages thereof which are designated as preferred in the above patents/applications which U.S. patents are incorporated herein by reference; most preferred are omapatrilat, gemopatrilat ([S [(R*,R*)]-hexahydro-6-[(2-mercapto-1-oxo-3-phenylpropyl)amino]-2,2-dimethyl-7-oxo-1H-azepine-1-acetic acid) and CGS 30440.

The angiotensin II receptor antagonist (also referred to herein as angiotensin II antagonist or AII antagonist) suitable for use herein includes, but is not limited to, irbesartan, losartan, valsartan, candesartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

It will be appreciated that preferred dosages of ACE inhibitor and AII antagonist will be as set out in the latest edition of the Physician's Desk Reference (PDR).

Dual action receptor antagonists (DARA) suitable for use herein include those disclosed in U.S. applications Ser. No. 09/513,779, filed Feb. 25, 2000, and Ser. No. 09/604,322, filed Jun. 26, 2000.

Other examples of preferred antihypertensive agents suitable for use herein include omapatrilat (Vanlev®), gemopatrilat, amlodipine besylate (Norvasc®), prazosin HCl (Minipress®), verapamil, nifedipine, diltiazem, felodipine, nisoldipine, isradipine, nicardipine, beta blockers such as nadolol, atenolol (Tenormin®), sotalol, terazosin, doxazosin, carvedilol, and propranolol, and clonidine HCl (Catapres®).

Diuretics which may be employed in combination with compounds of formula I include hydrochlorothiazide, torasemide, furosemide, spironolactone, and indapamide.

Antiplatelet agents which may be employed in combination with compounds of formula I of the invention include aspirin, clopidogrel, ticlopidine, dipyridamole, CS-747, (Lilly), abciximab, tirofiban, eptifibatide, anagrelide, and ifetroban, with clopidogrel and aspirin being preferred.

Anti-thrombotic agents which may be employed in combination with compounds of formula I of the invention include melagatran and ximelagatran (Exanta™ Astra Zeneca), warfarin and Factor Xa inhibitors such as razaxaban.

The antihypertensive agents, diuretics and antiplatelet drugs may be employed in amounts as indicated in the PDR. Ifetroban may be employed in amounts as set out in U.S. Pat. No. 5,100,889.

Anti-Alzheimer's agents or anti-dementia agents suitable for use herein with the HMG CoA reductase inhibitors of the invention include tacrine HCl (Cognex®) and donepezil (Aricept®), as well as γ-secretase inhibitors, β-secretase inhibitors and/or antihypertensive agents. Dosages employed will be as set out in the PDR.

Antiosteoporosis agents suitable for use herein in combination with the HMG CoA reductase inhibitors of the invention include parathyroid hormone or bisphosphonates, such as MK-217 (alendronate) (Fosamax®) as well as Ca receptor agonists and progestin receptor agonists. Dosages employed will be as set out in the PDR.

The hormone replacement therapeutic agents, where present, will be employed in dosages as set out in the latest edition of the PDR. Examples of such agents include selective estrogen receptor modulators (SERMs) such as raloxifen, tamoxifen or lasoxifen.

The HMG CoA reductase compound of the invention may also be employed in combination with a tyrosine kinase inhibitor such as disclosed in WO 2000/053605;

the selective androgen receptor modulator (SARM) suitable for use herein may be LGD-2226 (Ligand) or those compounds disclosed in WO 03/011824.

the antiarrhythmic agents suitable for use herein include β-blockers as set out herein including sotalol and amioderome, calcium channel blockers as set out herein including verapamil, nifedipine, amlodipine-besylate, and diltiazem, which may also be used in combination with a debrillator device such as a pace maker;

coenzyme Q sub. 10 such as disclosed in U.S. Pat. Nos. 5,316,765, 4,933,165, 4,929,437;

an agent that upregulates type III endothelial cell nitric acid syntase such as disclosed in WO 2000/003746;

a chondroprotective compound such as a polysulfated glycosaminoglycan (PSGAG), glucosamine, chondroitin sulfate (CS), hyaluronic acid (HA), pentosan polysulfate (PPS), doxycycline or minocycline, such as disclosed in EP 970694;

a cyclooxygenase (COX)-2 inhibitor, such as celecoxib (Celebrex® (Searle)) or rofecoxib (Vioxx® (Merck)) or a glycoprotein IIa/IIIb receptor antagonist such as disclosed in WO 99/45913 and tirofiban or abciximab;

a 5-HT reuptake inhibitor such as disclosed in WO 99/44609;

anti-anginal agents such as vasodilators, for example, isosorbide dinitrate, or nitroglycerin;

a growth hormone secretagogue such as disclosed in U.S. applications Ser. No. 09/662,448, filed Sep. 14, 2000, and U.S. Provisional application No. 60/203,335, filed May 11, 2000, and MK-677 (Merck), Pfizer's CP-424391 and Lilly's LY 444,711;

anti-atherosclerosis agents such as ACAT inhibitors and lipoxygenase inhibitors as described herein and phospholipase inhibitors;

anti-infective agents such as quinolones, for example, ciprofloxacin, ofloxacin, and Tequin® (Bristol-Myers Squibb), macrolides such as erythromycin and clarithromycin (Biaxin® (Abbott)), and azithromycin (Zithromax (Pfizer)); or an immunosuppressant (for use in transplantations) such as cyclosporine, mycophenolate mofetil, azathioprine and the like.

As used herein, the phrase "antineoplastic agent" refers to compounds which prevent cancer cells from multiplying. In general, the antineoplastic agents used herein prevent cancer cells from multiplying by: (1) interfering with the cell's ability to replicate DNA, or (2) inducing apoptosis in the cancerous cells.

Examples of antineoplastic agents which are suitable for use in combinations of this invention include, but are not limited to, microtuble-stabilizing agents such as the taxanes, for example, paclitaxel (also known as Taxol®), docetaxel (also known as Taxotere®), 7-O-methylthio-methylpaclitaxel (disclosed in U.S. Pat. No. 5,646,176), 3'-tert-butyl-3'-N-tert-butyloxycarbonyl-4-deacetyl-3'-dephenyl-3'-N-debenzoyl-4-O-methoxycarbonyl-paclitaxel (disclosed in U.S. Ser. No. 60/179,965 filed on Feb. 3, 2000, and example 17 herein), C-4 methyl carbonate paclitaxel (disclosed in WO 94/14787), the epothilone, such as epothilone A, epothilone B, epothilone C, epothilone D, desoxyepothilone A, desoxyepothilone B, [1S-[1R*,3R*(E),7R*,10S*, 11R*,12R*, 16S*]]-7,11-dihydroxy-8,8,10,12,16-pentamethyl-3-[1-methyl-2-(2-methyl-4-thiazolyl)ethenyl]-4-aza-17-oxabicyclo [14.1.0]hepta-decane-5,9-dione (disclosed in WO 99/02514), [1S-[1R*,3R*(E),7R*,10S*,11R*12R *,16S *]]-3-[2-[2-(aminomethyl)-4-thiazolyl]-1-methylethenyl]-7,11-di-hydroxy-8,8,10,12,16-pentamethyl-4,17-dioxabicyclo [14.1.0]-heptadecane-5,9-dione (disclosed in U.S. Ser. No. 09/506,481 filed on Feb. 17, 2000, and examples 7 and 8 herein), and derivatives thereof; microtuble-disruptor agents; alkylating agents; anti-metabolites; epidophyllotoxin; an antineoplastic enzyme; a topoisomerase inhibitor; procarbazine; mitoxantrone; platinum coordination complexes; biological response modifiers; growth inhibitors; hormonal/antihormonal therapeutic agents; and haematopoietic growth factors.

Other classes of antineoplastic agents suitable for use in the method of the present invention include, but are not limited to, the anthracycline family of drugs, the vinca drugs, the mitomycins, the bleomycins, the cytotoxic nucleosides, discodermolide, the pteridine family of drugs, diynenes, aromatase inhibitors, and the podophyllotoxins. Particularly useful members of those classes not previously mentioned include, for example, doxorubicin, carminomycin, daunorubicin, aminopterin, methotrexate, methopterin, dichloro-methotrexate, mitomycin C, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, leurosine, and the like. Other useful antineoplastic agents include estramustine, cisplatin, carboplatin, cyclophosphamide, bleomycin, tamoxifen, ifosfamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons, and interleukins.

It will be appreciated that unless otherwise specified the dosage regiment for therapeutic agents used in combination with the compounds of the invention will be as specified in the PDR.

In carrying out the method of the invention for treating hypercholesterolemia, hyperlipidemia, hyperlipoproteinemia, hypertriglyceridemia, or atherosclerosis, and related diseases, or Alzheimer's disease or osteoporosis, or other disclosures as set out hereinbefore, a pharmaceutical composition will be employed containing the compounds of structure I, with or without other cholesterol lowering agents, osteoporosis agents, Alzheimer's agents, antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compounds can be administered to mammalian species including humans, monkeys, dogs, etc. by an oral route, for example, in the form of tablets, capsules, beads, granules or powders, or they can be administered by a parenteral route in the form of injectable preparations, or they can be administered intranasally or in transdermal patches. Typical solid formulations will contain from about 0.1 to about 500 mg of a compound of formula I. The dose for adults is preferably between 0.5 and 1,000 mg per day, which can be administered in a single dose or in the form of individual doses from 1-4 times per day and also single dose once weekly (5 to 1000 mg).

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The following abbreviations are employed in the Examples and elsewhere herein:
AL=microliter
AcCN=acetonitrile
aq.=aqueous
Bn=benzyl
Boc=tert-butoxycarbonyl
bp=boiling point
Cbz=carbobenzyloxy or carbobenzoxy or benzyloxycarbonyl
DEAD=diethyl azodicarboxylate
Dess-Martins's periodinane=1,1,1-tris(acetyloxyl)-1,1-dihydro-1,2-benziodoxol-3-(1H)-one
DI water=dionized water
DIBAL=diisobutylaluminum hydride
DIPEA=diisopropyl ethylamine
DMPU=1,3-dimethyl-3,4,5,6-tetrahydro-2(1H)-pyrimidinone
EDAC=3-ethyl-3'-(dimethylamino)propyl-carbodiimide hydrochloride (or 1-[(3-(dimethyl)amino)propyl])-3-ethyl-carbodiimide hydrochloride)
Et=ethyl
Et$_2$NH=diethylamine
FMOC=fluorenylmethyloxycarbonyl
g=gram(s)
h or hr=hour(s)
HOAc or AcOH=acetic acid
HOAT=1-hydroxy-7-azabenzotriazole
HOBT or HOBT.H$_2$O=1 hydroxybenzotriazole hydrate
HPLC=high performance liquid chromatography
i-BU=iso-butyl
L=liter
LC/MS=high performance liquid chromatography/mass spectrometry
LDA=lithium diisopropylamide
LiHDMS=lithium bis(trimethylsilyl)amide
LiN(TMS)=Libis(trimethylsilyl)amide
MCPMA—m-chloro-p-benzoic acid
Me=methyl
meq=milliequivalent
mg=milligram(s)
min=minute(s)
mL=milliliter
mmol=millimole(s)
mol=moles
mp=melting point
MS or Mass Spec=mass spectrometry
MTBE=methyl t-butyl ether
NaHMDS=sodium bis(trimethylsilyl)amide
n-BuLi=n-butyllithium
NMM=N-methyl morpholine
NMO=methylmorpholine N-oxide
NMR=nuclear magnetic resonance
Pd/C=palladium on carbon
Ph=phenyl
PPh$_3$=triphenylphosphine
PtO$_2$=platinum oxide
PTSH=N-phenylthiotetrazole
PyBOP reagent=benzotriazol-1-yloxy-tripyrrolidino phosphonium hexafluorophosphate
Red-AL=sodium bis(2-methoxyethoxy)aluminum hydride
RT, rt=room temperature
sat or sat'd=saturated
TEA=triethylamine
TEMPO=2,2,6,6-tetramethyl-1-piperidinyloxy free radical
TFA=trifluoroacetic acid
TLC=thin layer chromatography
TMS=trimethylsilyl
TPAP=tetrapropylammonium perruthenate

EXAMPLES

The following Examples represent preferred embodiments of the invention. Compound names cited in the examples, unless otherwise indicated, can be converted to structure drawings using the AutoNom (v 2.1) feature in Chem-Draw Ultra v 6.0.4.

Example 1

A.

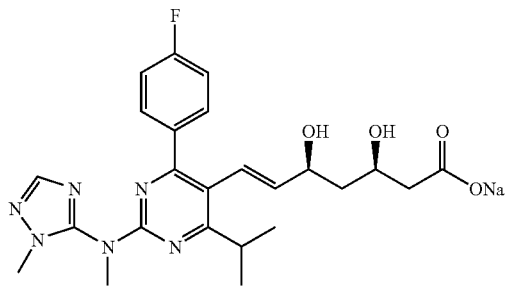

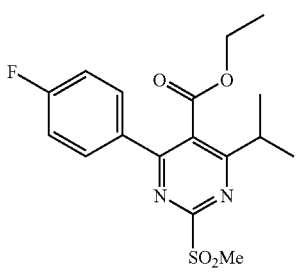

This compound was prepared according to the procedure reported by Masamichi Watanabe et al. (Bioorganic & Medicinal Chemistry (1997), 5(2), 437-444; Eur. Pat. Appl. 1993, 18 pp. EP521471).

B.

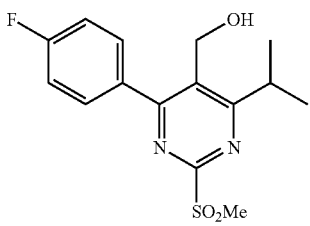

To a solution of the compound from part A (3.7 g, 10.1 mmol) in 100 mL toluene at −70° C. was added DIBAL (1 M in methylene chloride, 25 mL, 25 mmol) dropwise. After stirring at −70° C. for 0.5 h, the reaction mixture was quenched by carefully adding saturated ammonium chloride solution and stirred at RT for 0.5 h. The organic layer was separated, dried over MgSO$_4$, concentrated, and the crude product thus obtained was subjected to flash chromatography (silica gel/hexane-EtOAc 80:20 to 20:80 gradient to afford the title compound as a white solid (2 g, 61% yield).

C.

To a solution of the title compound of part B (2 g, 6.2 mmol), TEMPO free radical (Aldrich Chemical Co., 10 mg) and KBr (73 mg) in 20 mL EtOAc at 0° C. was added a solution of buffered bleach (ca. 0.9 M, adjusted to pH 9.4 by the addition of solid sodium bicarbonate) dropwise with stirring over 0.5 h. The mixture was sequentially washed with ½ saturated sodium thiosulfate, 1N NaOH and brine. The organic layer was dried (MgSO$_4$) and concentrated to afford the title compound 1.98 g (crude yield 99%).

D.

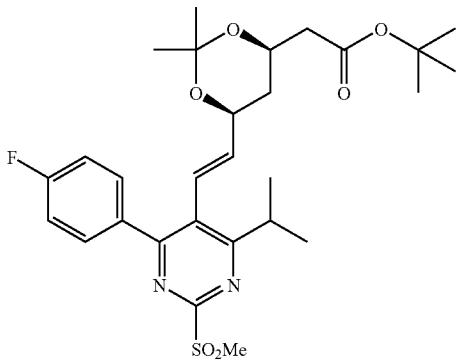

To a solution of the title compound of part C (1.98 g, 6.1 mmol) and

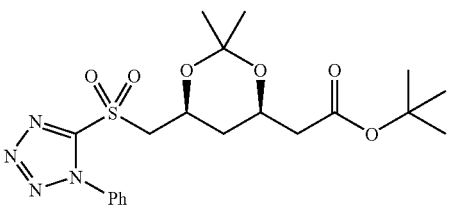

(Brodfuehrer, Paul R. et al. PCT Int. Appl. (2002), WO 0298854, 2.79 g, 6.1 mmol) in 25 mL THF at −78° C. was added with stirring a solution of lithium bistrimethylsilylamide (1M in THF, 7.75 mL, 7.75 mmol) dropwise. After 15 min. at −78° C. the mixture was quenched by adding sat. NaHCO$_3$, extracted with EtOAc, dried (MgSO$_4$), concentrated and the crude product was purified by flash chromatography (silica gel/hexane EtOAc 100:0 to 50:50 gradient) to afford 1.1 g of the title compound as a pale foamy solid.

E.

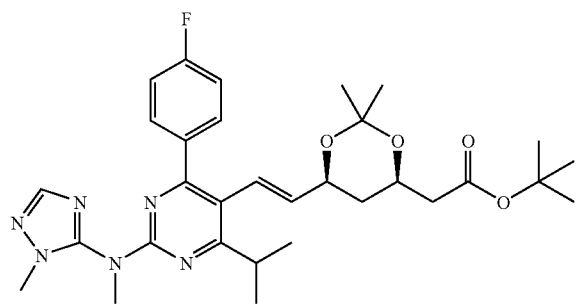

F.

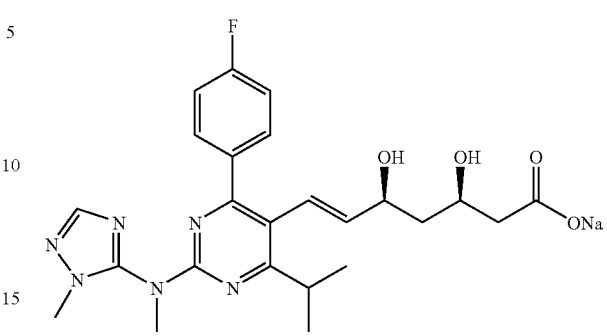

Lithium bis(trimethylsilyl)amide (1.0 M in THF, 407 mL, 0.47 mol) was added over 65 min to a stirred solution of 2-methyl-2H-[1,2,4]triazol-3-ylamine (37.5 g, 0.37 mol, prepared as described by Barascut, Jean L. et al., Bull. Soc. Chim. Fr. (1973), (5) part 2, 1849-53) and iodomethane (66.6 mL, 1.11 mol) in THF (1.2 L) under nitrogen at 0° C. After stirring at 0° C. for 1.5 h, additional lithium bis (trimethylsilyl)amide (1.0 M in THF, 90 mL, 0.09 mol) was added over 10 min. After stirring for an additional 2.5 h, $^1$H NMR of an aliquot indicated 9% starting material, 74% of the desired product (methyl-(2-methyl-2H-[1,2,4]triazol-3-yl)-amine), and 17% of trimethylated product (dimethyl-(2-methyl-2H-[1,2,4]triazol-3-yl)-amine) and the reaction was quenched with water (~7 mL) and evaporated in vacuo. The white solid which had formed when the reaction volume had been reduced to 500 mL was filtered. The filtrate was then evaporated to afford 228 g of crude product. The crude product was chromatographed (alumina activity I/EtOAc-CH$_2$Cl$_2$) to afford 20.1 g (48%) methyl-(2-methyl-2H-[1,2,4]triazol-3-yl)-amine. $^1$H NMR (CDCl$_3$) δ7.40 (1 H, s), 4.71 (1 H, broad s), 3.48 (3 H, s), and 2.92 (3 H, d, J=5.0 Hz). $^{13}$C NMR (CDCl$_3$) ppm 156.0, 147.8, 32.9, and 29.9.

To a stirred solution of methyl-(2-methyl-2H-[1,2,4]triazol-3-yl)-amine (prepared as described above, 51.5 g, 0.46 mol) in 1 L THF at −60° C. under nitrogen was added a solution of of 1 N lithium bis(trimethylsilyl)amide (480 mL, 0.48 mol) over 15 minutes. The mixture was allowed to come to 10° C. and stirred for 15 minutes. The reaction mixture was cooled to −60° C., and the resulting slurry was transferred over 30 minutes to a stirred solution of the title compound of step D (200 g, 0.365 mol) in 1 L THF at −60° C. The reaction mixture was allowed to come to −17° C. over 1 h, diluted with EtOAc and washed sequentially with sat. NaHCO$_3$ solution an brine. The organic layer was dried and concentrated and the crude product thus obtained was subjected to flash chromatography (silica gel/hexane-EtOAc 100:0 to 50:50 gradient) to afford 176 g of white solid. This material was recrystallized from MeOH-water to afford the title compound as a white solid (170 g).

To a solution of the title compound prepared in a manner similar to that described in step E (234 g, 402.7 mmol) in 1L THF was added 1N HCL (403 mL). The reaction mixture was stirred at RT for 6 h, then added a solution of NaOH (32.5 g) in 150 mL water followed by the addition of 100 mL methanol. The reaction mixture was stirred for 1.5 h at RT, diluted with water (200 mL) and extracted with EtOAc (3×500 mL). The aqueous layer was concentrated and the residue was subjected to reversed phase chromatography (C18 silica/water-acetonitrile 100:0 to 70:30) to afford the title compound as a white solid (166.8 g); analytical LC retention time=3.30 minutes (YMC ODS S5 4.6 mm×X 50 mm column/methanol-water-phophoric acid 10:90:0.2 to 90:10:0.2 gradient over 4 minutes, 4 mL/min. flow rate); (M+H)+485 (carboxylic acid).

Example 1A

The Example 1 Part C compound may also be prepared as described below.

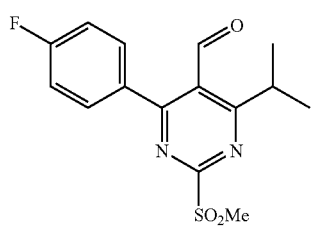

A.

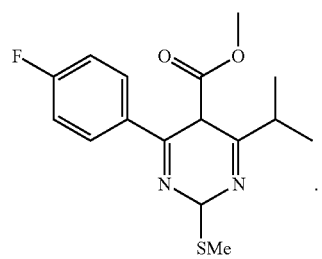

A mixture of

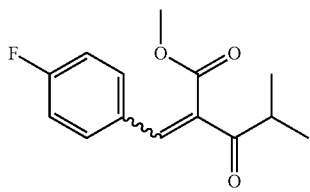

(250.27 g, 1.0 mole, Robl, Jeffrey A.; Chen, Bang-Chi; Sun, Chong-Qing. U.S. Pat. No. 6,620,821) and S-methyl-isothiouronium sulfate (162.84 g, 0.585 mole) in 750 mL HMPA was heated with stirring at 100° C. for 24 h, allowed to come to RT and diluted with EtOAc. The mixture was washed sequentially with sat. NaHCO$_3$ and brine, dried over sodium sulfate and concentrated to afford 286 g of the title compound.

B.

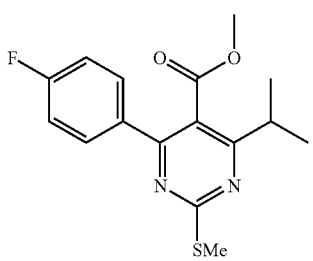

To a solution of the title compound from step A (286 g, 0.887 mole) in 1.5 L MeOH was added DDQ (154 g) in small portions with stirring at −40° C. to −20° C. The mixture was allowed to come to RT and stirred for 30 min. This was diluted with water and the resulting solid was isolated and washed with 1:1 water-ethanol to give the title compound as a white solid (221 g).

C.

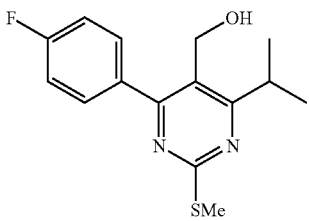

This compound was prepared from the step B compound in a manner similar to that described for the title compound of step B, Example 1.

D.

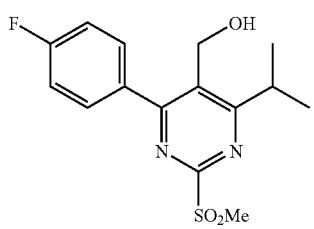

Hydrogen peroxide (30%, 500 mL) was added at RT to a stirred solution of the compound from step C (424 g, 1.45 mole), ammonium heptamolybdate tetrahydrate (26.8 g, 0.022 mole) and tricaprylylmethylammonium chloride Aliquat® 336, Aldrich) (58.7 g, 0.145 mole) in CH$_2$Cl$_2$ (3 L) over 1 h (exotherm observed causing the solvent to reflux). The reaction mixture was stirred at RT for 3 h, washed sequentially with water, sat. sodium thiosulafte and water. The organic layer was dried and concentrated to afford 470 g of the title compound.

E.

This compound was prepared from the step D compound in a manner similar to that described for the step C compound of Example 1.

Example 2

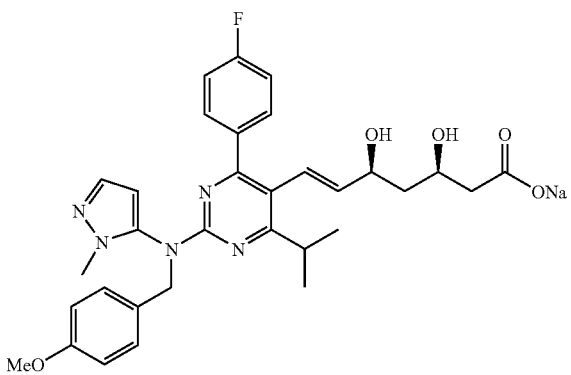

A.

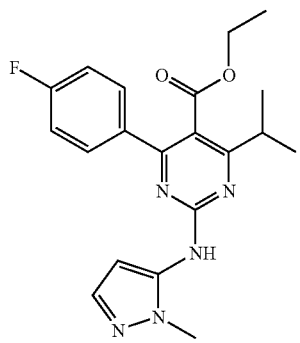

A mixture of 2H-Pyrazol-3-ylamine (3 g) and methyl iodide (5.13 g) in 150 mL THF was stirred for 1 h at RT followed by the addition of potassium carbonate (4.5 g). The mixture was stirred at RT for an additional 1.5 h, diluted with methylene chloride, filtered and the filtrate was concentrated to afford a crude mixture of products. This was subjected to flash chromatography (silica gel/methylene chloride-methanol-$NH_4OH$ 90:10:1) to afford a 1:1 mixture of 2-Methyl-2H-pyrazol-3-ylamine and Methyl-(2H-pyrazol-3-yl)-amine (0.8 g). A solution of this mixture in 5 mL N-methylpyrrolidone (NMP) was added was added to a stirred mixture of the title compound of example 1, step A (3 g, 8.0 mmol) and potassium carbonate (1.5 g) in 15 mL NMP. The mixture was stirred at RT for 14 h, diluted with methylene chloride, washed with water and the organic phase was dried ($MgSO_4$) and concentrated to give crude product. This was subjected to flash chromatography (silica gel/hexane-EtOAc 9:1 to 2:1 gradient) to afford 0.75 g of the title compound (as well 1.35 g of the starting unreacted slfone).

B.

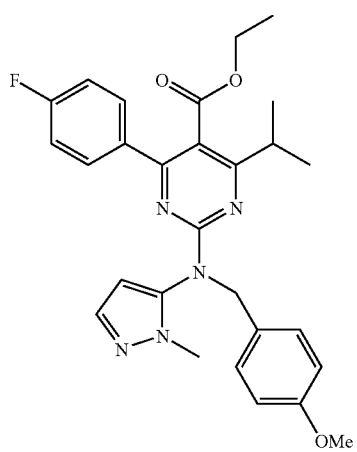

Potassium hydride (washed, 24 mg, 0.59 mmol) was added to a stirred solution of the title compound from step A (94 mg, 0.245 mmol) and 4-methoxybenzyl chloride (42.2 mg, 0.27 mmol) in 0.5 mL DMF at RT. After stirring for 1 h at RT the mixture was quenched with sat. $NaHCO_3$, extracted with methylene chloride, dried and concentrated. The crude product was purified by flash chromatography (silica gel/hexane-EtOAc 80:20) to give 40 mg of the title compound as a gummy solid.

C.

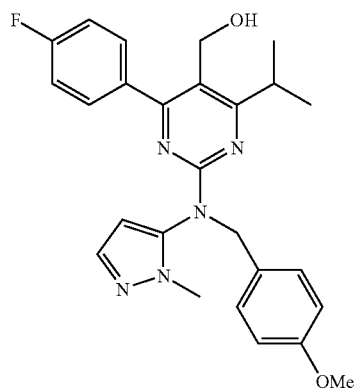

The compound from step B (0.3 g) was reduced using DIBAL as described for the synthesis of the title compound of Example 1, step B to give 0.15 g of the title compound.

D.

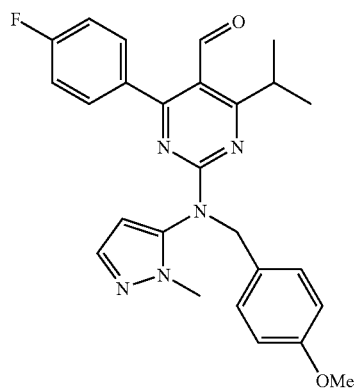

The compound from step C (100 mg) was oxidized as described for the synthesis of the title compound of Example 3, step F to give 75 mg of the title compound.

E.

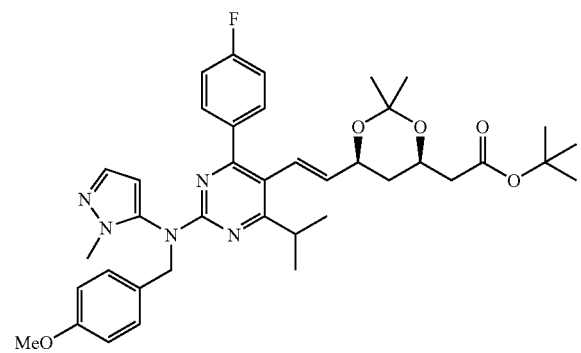

This compound was prepared as described for the title compound of Example 1, step D.

F.

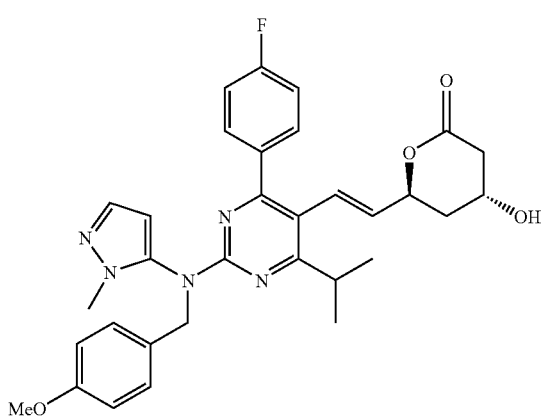

A solution of the compound from step E (90 mg) in methylene chloride (5 mL) was treated with TFA (0.5 mL) at RT for 6 h. The mixture was washed with sat. NaHCO$_3$, dried and concentrated to give the title compound as a gummy solid (75 mg).

G.

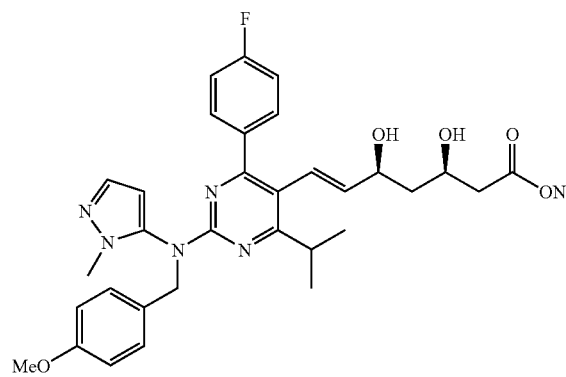

To a solution of the compound from step F (10 mg) in THF (0.1 ML) was added 1N NaOH (0.022 mL) and water (0.028 mL). The reaction mixture was stirred at RT for 0.5 h, concentrated and the residue was subjected to reversed phase chromatography (C18 silica/MeOH-water 0:100 to 100:0 gradient) to afford the title compound as a white solid (5 mg), analytical LC retention time=2.9 minutes (YMC ODS S5 4.6 mm×50 mm column/methanol-water-TFA 10:90:0.1 to 90:10:0.1 gradient over 4 minutes, 4 mL/min. flow rate); (M+H)$^+$ 590 (carboxylic acid).

Example 3

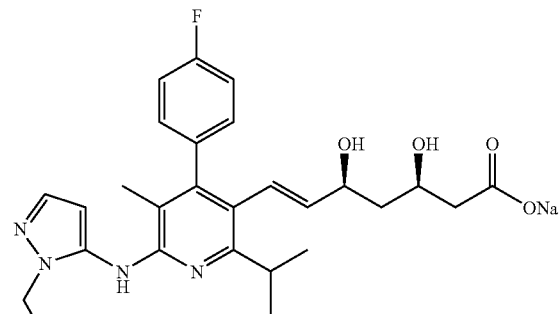

A.

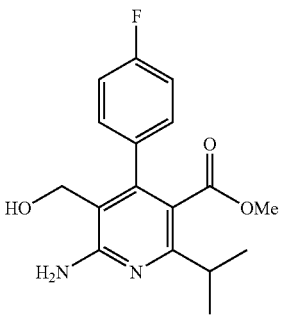

To a stirred solution of

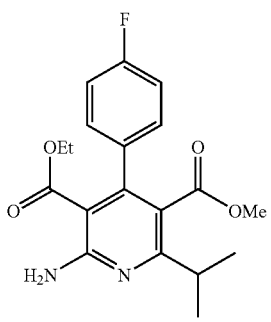

(3 g; Huebsch, Walter et al. Ger. Offen. (1992), DE 4023308; Huebsch, Walter et al. Eur. Pat. Appl. (1992), EP 465970) in 50 mL THF at −78° C. was added 1M LAH in THF (25 mL). The mixture was stirred at 0° C. for 1 h, quenched by adding sat. NaHCO$_3$ and extracted with EtOAC. The organic layer was dried over sodium sulfate, concentrated to afford 2.65 g of the title compound.

B.

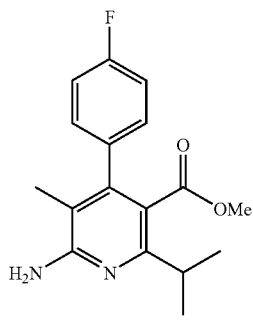

A mixture of the title compound of step A (2.65 g), trifluoroacetic acid (2 mL), 10% Pd/C (3 g) in 50 mL EtOH was shaken for 8 h under hydrogen (50 psi, Parr shaker). The mixture was filtered and the filtrate was concentrated to afford 1.9 g of the title compound.

C.

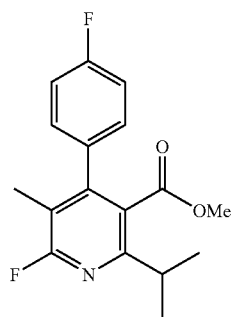

To a solution of the title compound from step B (1.9 g) in 50 mL tetrafluoroboric acid at −10° C. was added 3.0 g sodium nitrite in small portions. The mixture was stirred at −10° C. for 30 minutes, added slowly to a saturated sodium bicarbonate solution. The mixture was extracted with EtOAc, the organic phase was dried over sodium sulfate, concentrated and the residue was purified by flash chromatography (silica gel/methylene chloride) to give the title compound (1.55 g) as a white solid.

D.

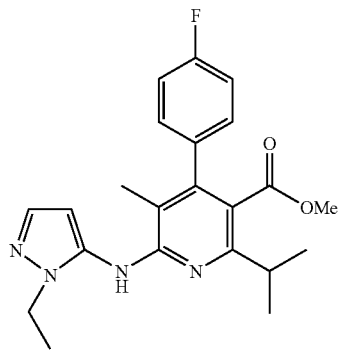

To a stirred solution of the title compound from step C (15 g) 2-Ethyl-2H-pyrazol-3-ylamine (19.1 g) in THF (250 mL) at −78° C. was added 1M lithium bistrimethylsilylamide (213 mL). The mixture was allowed to come to RT, then refluxed for 4 h followed by the addition of saturated sodium bicarbonate solution. The mixture was extracted with EtOAc, the EtOAc layer was dried over sodium sulfate, concentrated and the residue was flash chromatographed (silica gel/hexane-EtOAc 90:10 to 80:20) affording the title compound as a brown solid (12.8 g).

E.

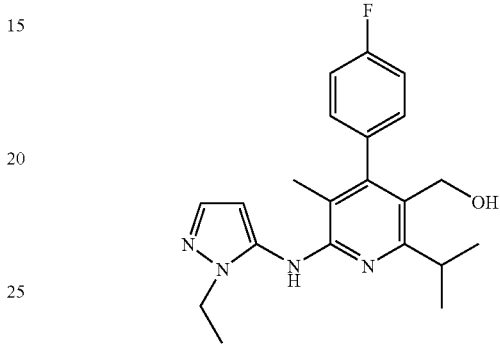

To a stirred solution of the title compound from step D (12.8 g) in dichloromethene (200 mL) at −78° C. was added 1M DIBAL in dichloromethane (96.9 mL). The mixture was stirred at −78° C. for 1 h, quenched by adding water and saturated sodium potassium tartarate solution and stirred at RT for 2 h. The mixture was extracted with dichloromethane, the organic layer was dried over sodium sulfate and concentrated to afford the title compound (11 g) as a white solid.

F.

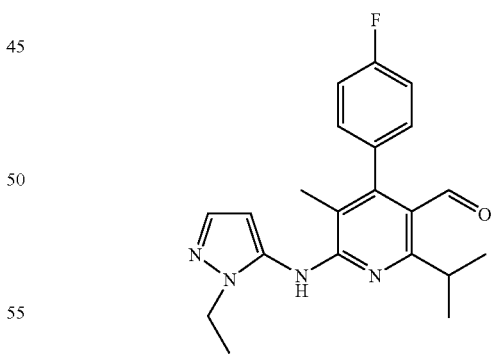

To a stirred solution of the title compound of step E (11 g) in DMF (50 mL) and dichloromethane (300 mL)was added Dess-Martin's periodinane (12.6 g). The mixture was stirred at RT for 1 h, washed with saturated sodium bicarbonate solution, dried over sodium sulfate and concentrated. The crude product was flash chromatographed (siliac gel/hexane-EtOAc 80:20) to afford the title compound (7.0 g) as a brown solid.

G.

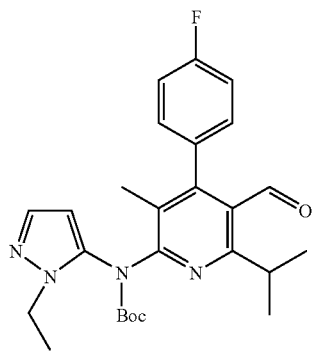

To a stirred solution of the title compound from step F (7.0 g) in methylene chloride (100 mL) was sequentially added di-tert-butyldicarbonate (12.5 g) and 4-dimethylaminopyridine (DMAP, 7.01 g). The mixture was stirred at RT for 5 h, concentrated and the residue was subjected to flash chromatography (silica gel/hexane-EtOAc 85:15) to give the title compound (7.0 g) as a brown solid.

H.

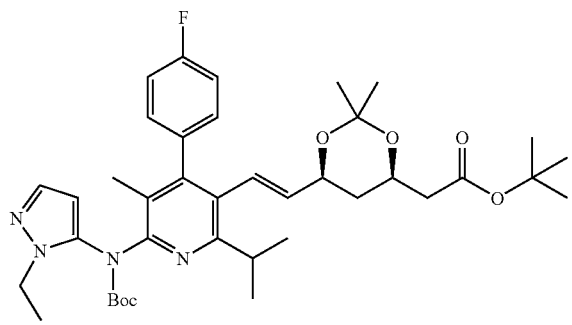

This compound was prepared from the title compound of step G as described for the synthesis of the title compound of Example 1, step D.

I.

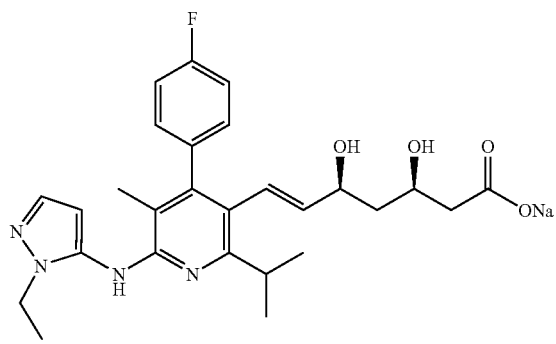

To a stirred solution of the title compound of step H (11.0 g) in 90 mL methylene chloride at −15° C. was added trifluoroacetic acid (90 mL). The mixture was stirred at −15° C. for 3 h, poured into a cold solution of 3N NaOH (467 mL), concentrated and the residue subjected to reversed phase chromatography (C18 silica/methanol-water 0:100 to 100:0 gradient) to afford the title compound as a white solid (4.0 g); analytical LC retention time=1.83 minutes (YMC ODS S5 4.6 mm×50 mm column/methanol-water-phophoric acid 10:90:0.2 to 90:10:0.2 gradient over 4 minutes); $(M+H)^+$ 497 (carboxylic acid).

Example 4

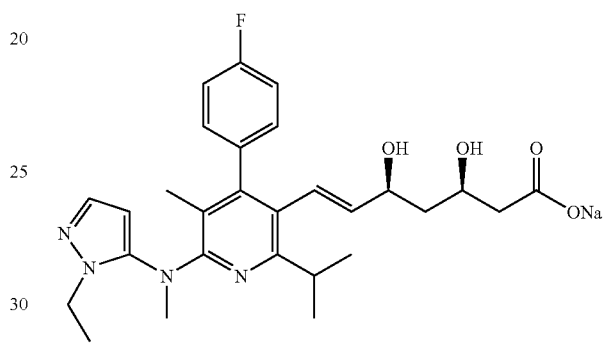

A.

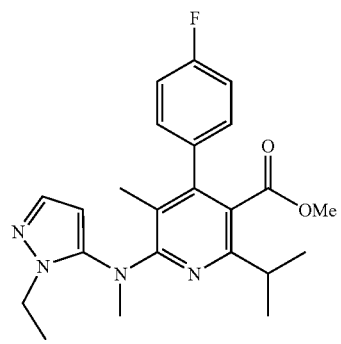

To a stirred solution of the title compound of Example 2 step D (200 mg) in THF (5 ml) at −78° C. was added 1.0M lithium bistrimethylsilylamide (505 µl, the reaction mixture was stirred at −78° C. for 15 minutes. Iodomethane (200 µl)was added to the reaction mixture, the mixture was allowed to come to RT and was stirred for an addditional 1 hour. The mixture was diluted with saturated sodium bicarbonate solution (30 ml) and was extracted with ethyl acetate (30 ml). The ethyl acetate layer was dried over sodium sulfate and concentrated. The crude product was purified by flash chromatography (silica gel/haxane-EtOAc 90:10 to 70:30 gradient) to give the title compound as a clear gum (164 mg).

B.

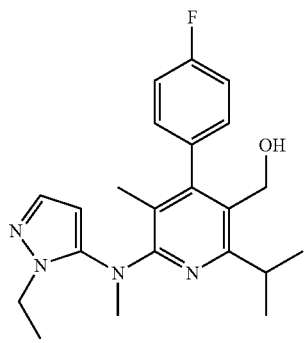

The title compound was prepared from the title compound of step A as described for the synthesis of the title compound of Example 3 step E.

C.

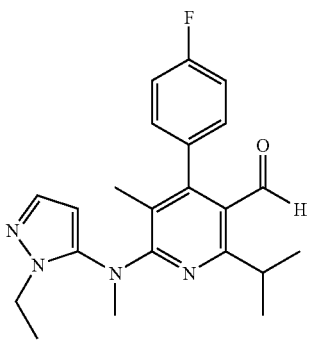

The title compound was prepared from the title compound of step B as described for the synthesis of the title compound of Example 3 step F.

D.

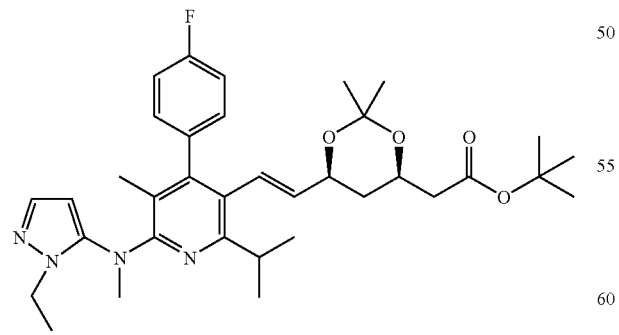

The title compound was prepared from the title compound of step C as described for the synthesis of the title compound of Example 3 step H.

E.

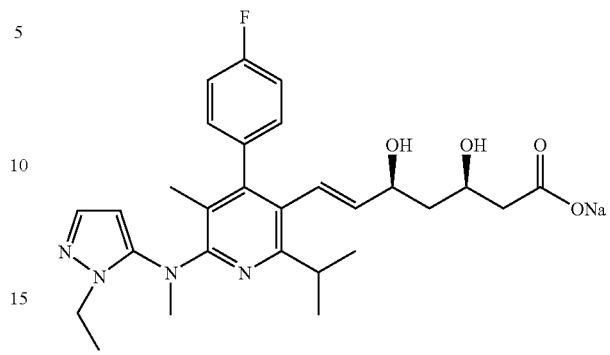

The title compound was prepared from the title compound of step D as described for the synthesis of the title compound of Example 3 step I; analytical LC retention time=26.7 minutes (YMC ODS S5 6 mm×150 mm column/methanol-water-phophoric acid 10:90:0.2 to 90:10:0.2 gradient over 30 minutes, 1.5 mL/min. flow rate); (M+H)$^+$ 511 (carboxylic acid).

Example 5

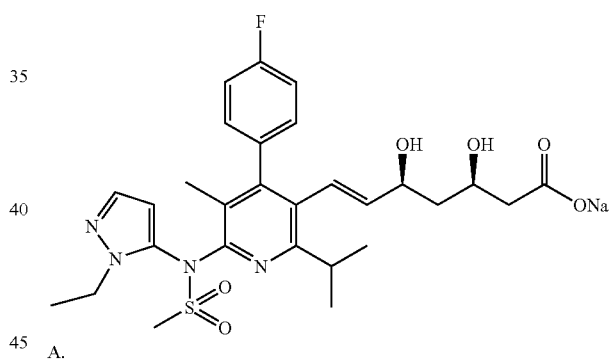

A.

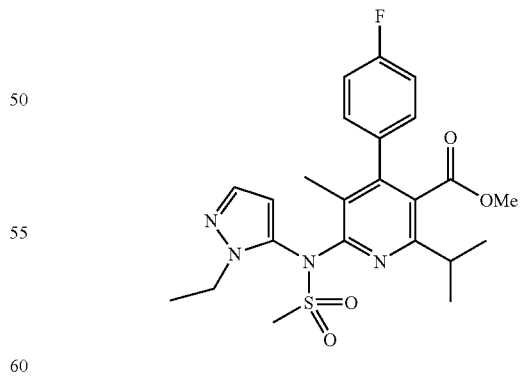

To a stirred solution of the title compound of Example 3 step D (200 mg) in THF (5 ml) at −78° C. was added 1.0M lithium bistrimethylsilylamide (505 μl), the reaction mixture was stirred at −78° C. for 15 minutes. Methane sulfonyl chloride (78 μl)was added to the reaction mixture at −78° C., the mixture was stirred at −78° C. for 1 hour. The mixture was diluted with saturated sodium bicarbonate solution (30 ml) and was extracted with ethyl acetate (30 ml). The ethyl acetate layer was dried over sodium sulfate and concentrated. The crude product was purified by flash chromatography (silica gel/haxane-EtOAc 90:10 to 70:30 gradient) to give the title compound as a brown gum (200 mg).

B.

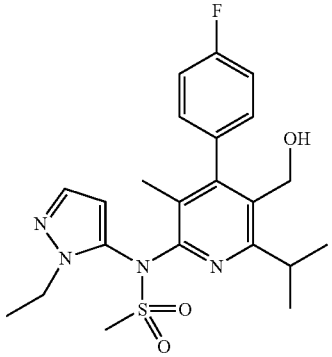

The title compound was prepared from the title compound of step A as described for the synthesis of the title compound of Example 3 step E.

C.

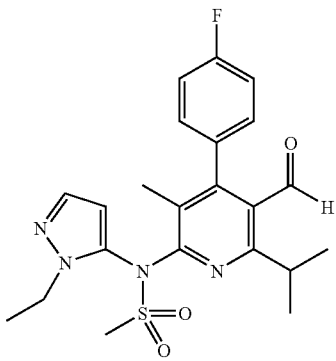

The title compound was prepared from the title compound of step B as described for the synthesis of the title compound of Example 3 step F.

D.

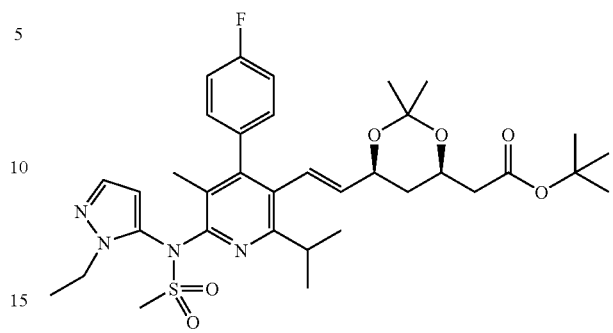

The title compound was prepared from the title compound of step C as described for the synthesis of the title compound of Example 3 step H.

E.

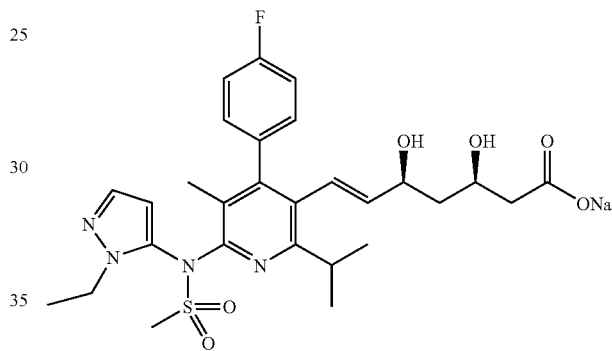

The title compound was prepared from the title compound of step D as described for the synthesis of the title compound of Example 3 step I. Analytical LC retention time=23.5 minutes (YMC ODS S5 6 mm×150 mm column/methanol-water-phophoric acid 10:90:0.2 to 90:10:0.2 gradient over 30 minutes, 1.5 mL/min. flow rate); $(M+H)^+$ 575 (carboxylic acid).

The following compounds were prepared employing the procedure set out in Examples 1 and 2:

| Example No. | Structure | MS $[M + H]^+$ |
|---|---|---|
| 6 | 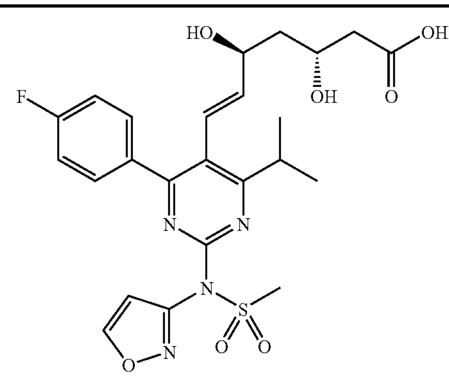 | 535 |

-continued

| Example No. | Structure | MS [M + H]+ |
| --- | --- | --- |
| 7 | 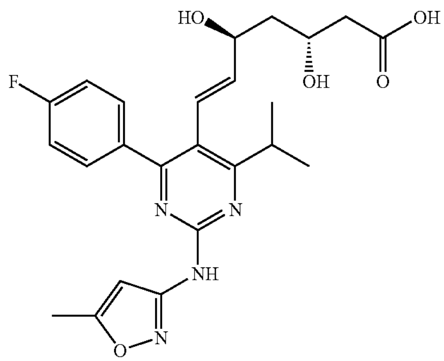 | 471 |
| 8 | 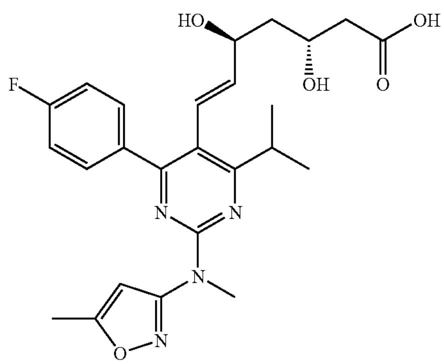 | 485 |
| 9 | 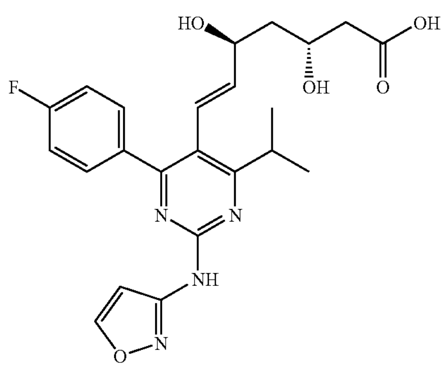 | 457 |
| 10 | 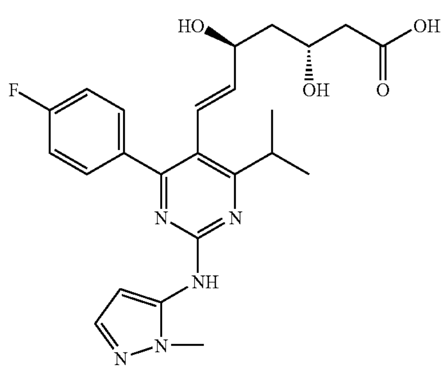 | 470 |

-continued

| Example No. | Structure | MS [M + H]+ |
|---|---|---|
| 11 | 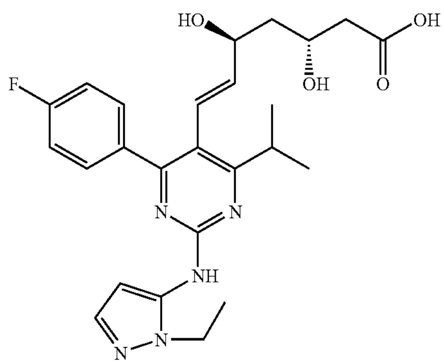 | 484 |
| 12 | 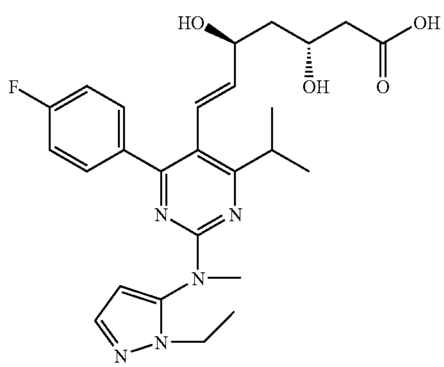 | 498 |
| 13 | 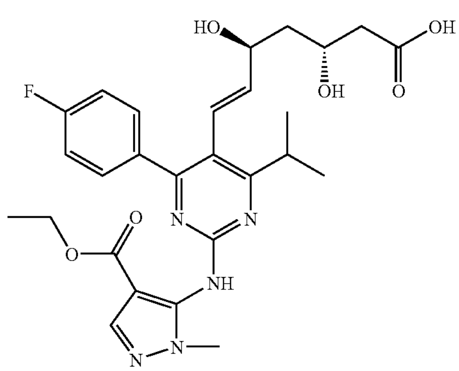 | 542 |
| 14 | 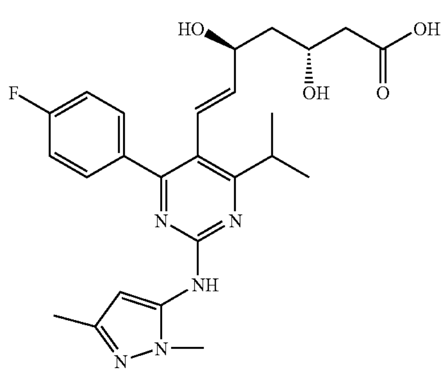 | 484 |

| Example No. | Structure | MS [M + H]⁺ |
|---|---|---|
| 15 | 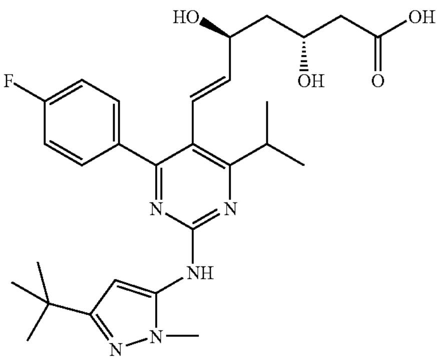 | 526 |
| 16 | 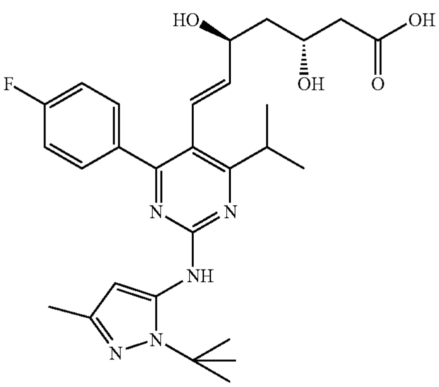 | 526 |
| 17 | 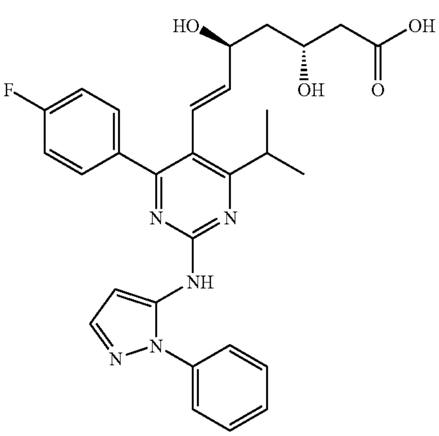 | 532 |
| 18 | 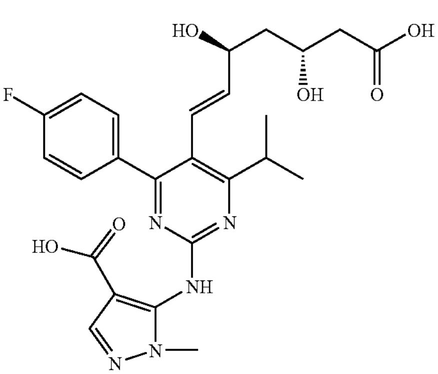 | 514 |

-continued

| Example No. | Structure | MS [M + H]+ |
| --- | --- | --- |
| 19 | 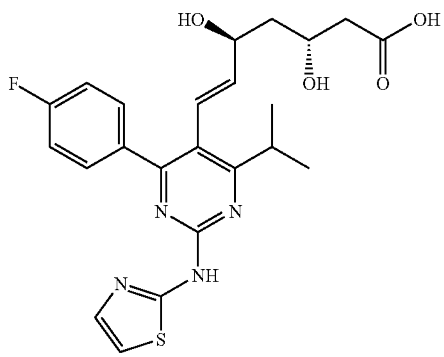 | 473 |
| 20 | 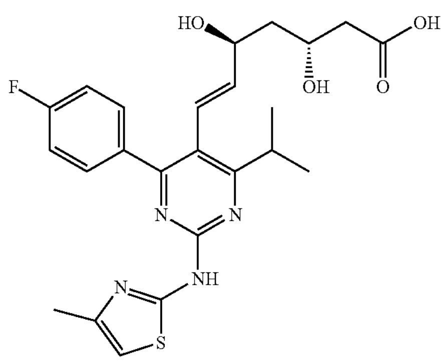 | 487 |
| 21 | 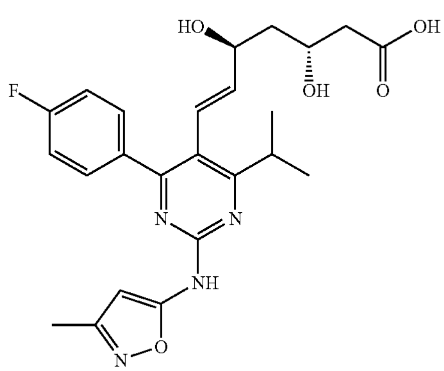 | 471 |
| 22 | 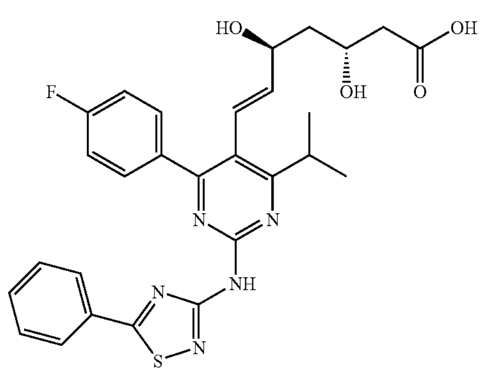 | 550 |

-continued
| Example No. | Structure | MS [M + H]+ |
| --- | --- | --- |
| 23 | 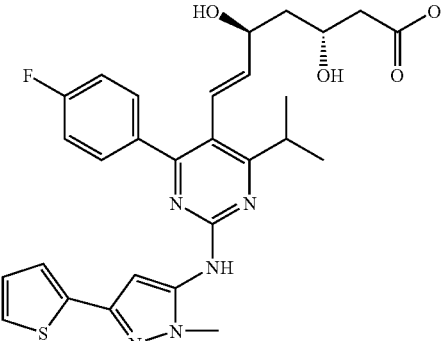 | 552 |
| 24 | 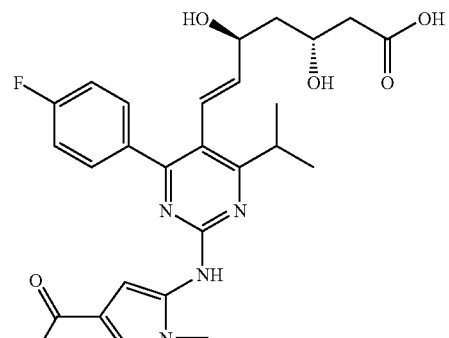 | 514 |
| 25 | 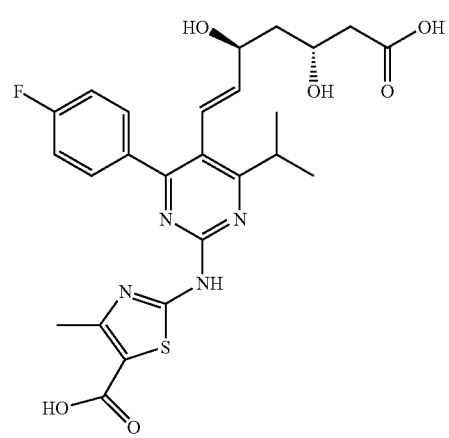 | 531 |
| 26 | 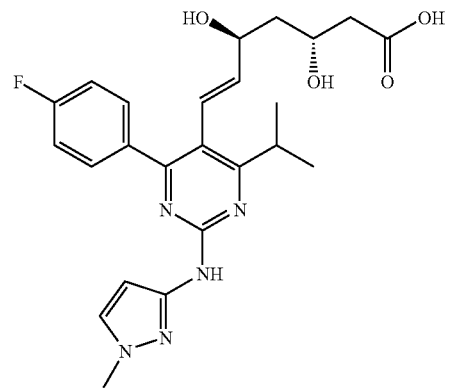 | 470 |

| Example No. | Structure | MS [M + H]+ |
|---|---|---|
| 27 | 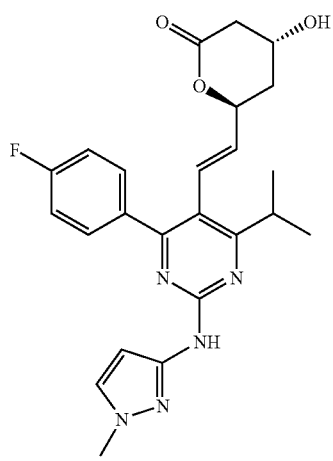 | 452 |
| 28 | 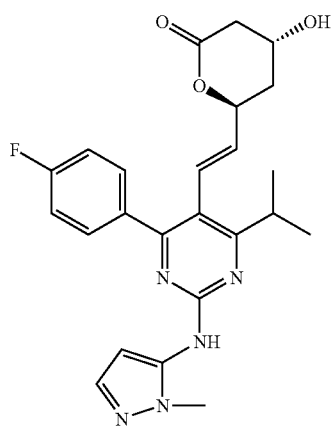 | 452 |
| 29 | 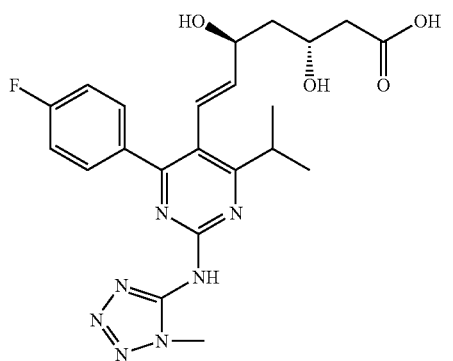 | 472 |

-continued

| Example No. | Structure | MS [M + H]+ |
|---|---|---|
| 30 | 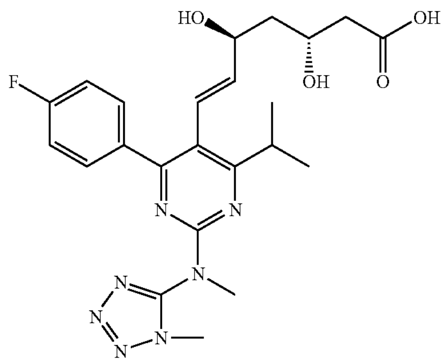 | 486 |
| 31 | 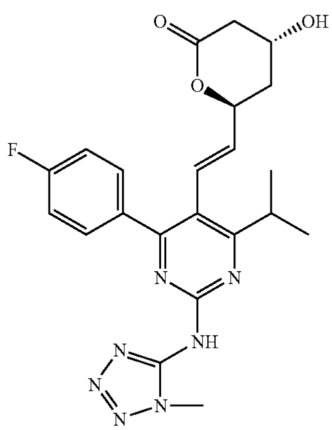 | 454 |
| 32 | 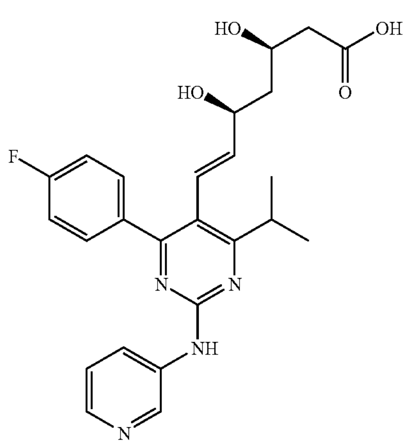 | 467 |

| Example No. | Structure | MS [M + H]+ |
|---|---|---|
| 33 | 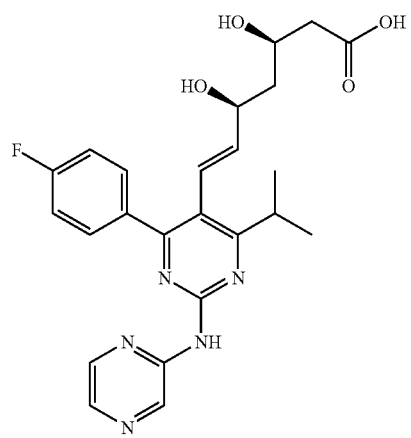 | 468 |
| 34 | 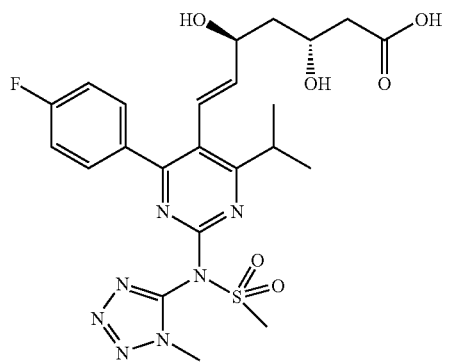 | 550 |
| 35 | 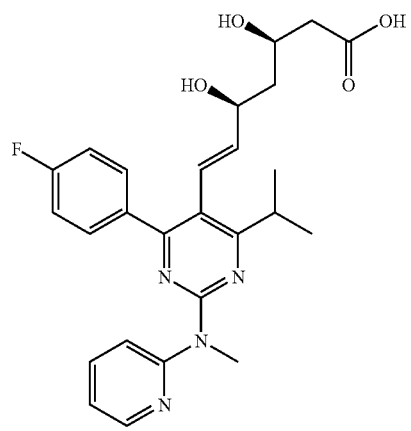 | 481 |

-continued

| Example No. | Structure | MS [M + H]+ |
|---|---|---|
| 36 | (structure) | 467 |
| 37 | (structure) | 467 |
| 38 | (structure) | 546 |

-continued
| Example No. | Structure | MS [M + H]+ |
| --- | --- | --- |
| 39 | 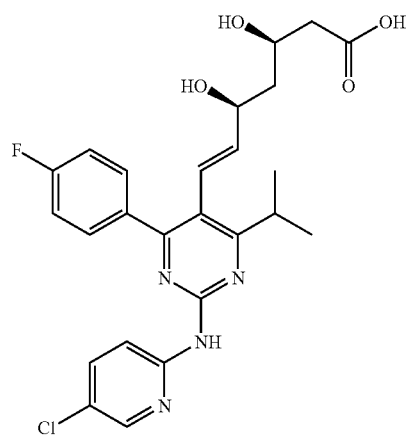 | 501 |
| 40 | 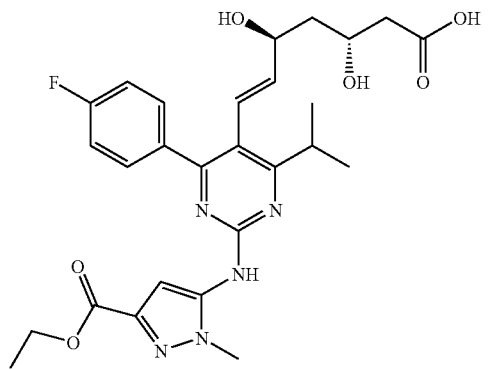 | 542 |
| 41 | 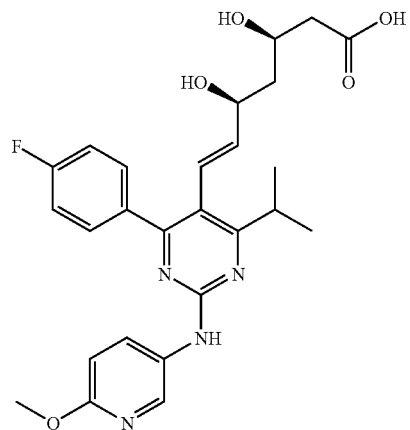 | 497 |

-continued
| Example No. | Structure | MS [M + H]+ |
|---|---|---|
| 42 | 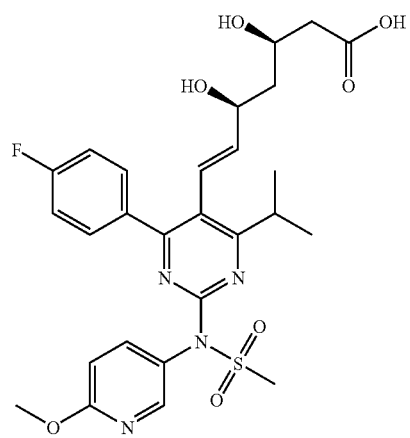 | 575 |
| 43 | 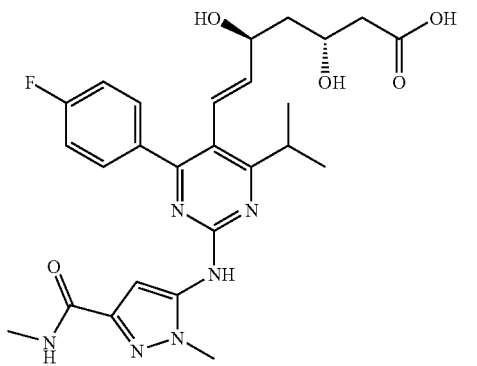 | 527 |
| 44 | 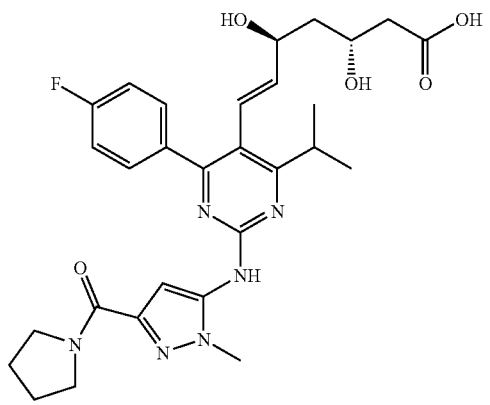 | 567 |

| Example No. | Structure | MS [M + H]+ |
|---|---|---|
| 45 | 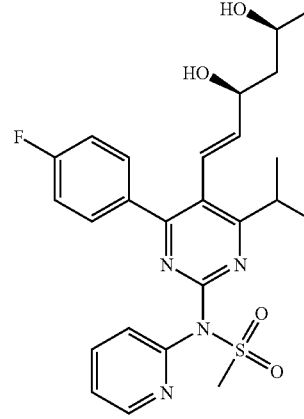 | 545 |
| 46 | 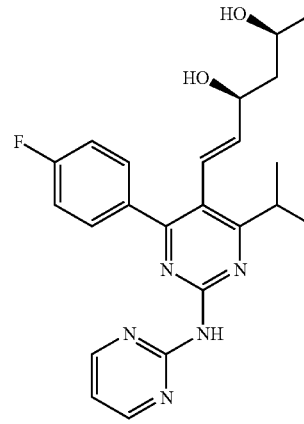 | 468 |
| 47 | 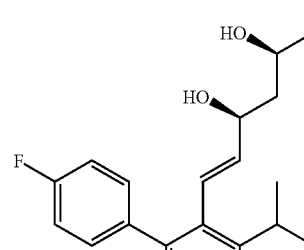 | 509 |

| Example No. | Structure | MS [M + H]+ |
|---|---|---|
| 48 | 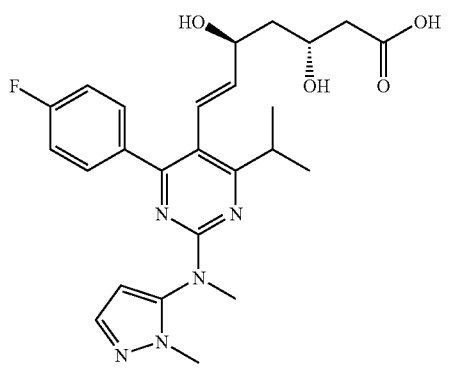 | 484 |
| 49 | 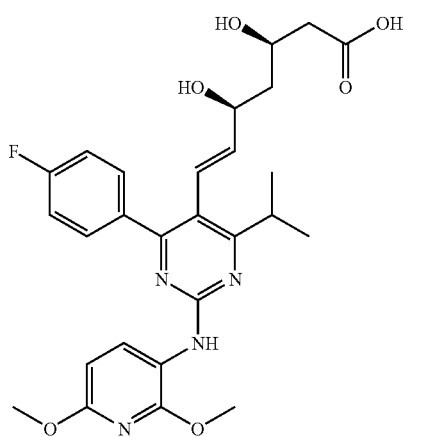 | 527 |
| 50 | 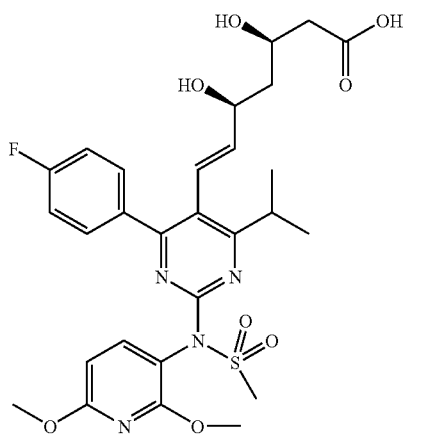 | 605 |

-continued
| Example No. | Structure | MS [M + H]+ |
| --- | --- | --- |
| 51 | 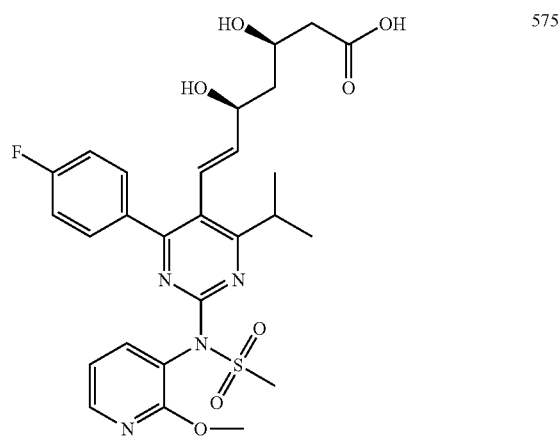 | 575 |
| 52 | 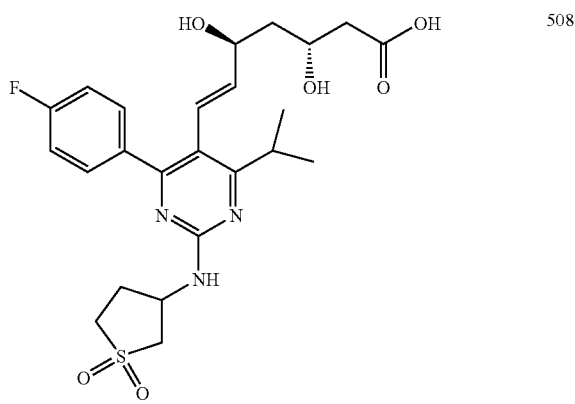 | 508 |
| 53 | 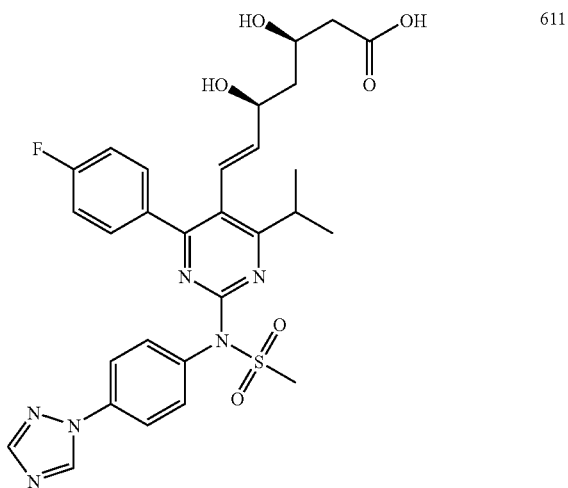 | 611 |

-continued
| Example No. | Structure | MS [M + H]+ |
| --- | --- | --- |
| 54 | 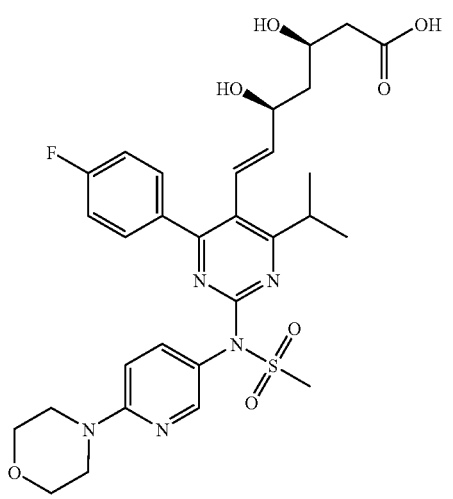 | 630 |
| 55 | 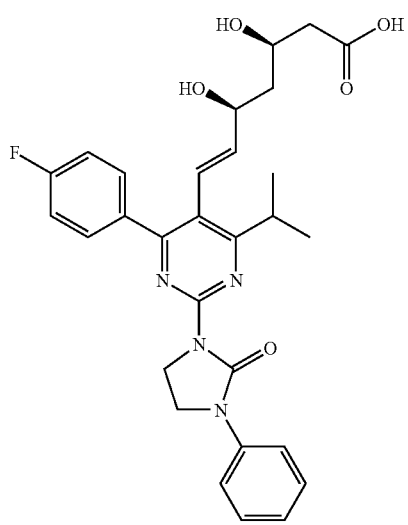 | 535 |
| 56 | 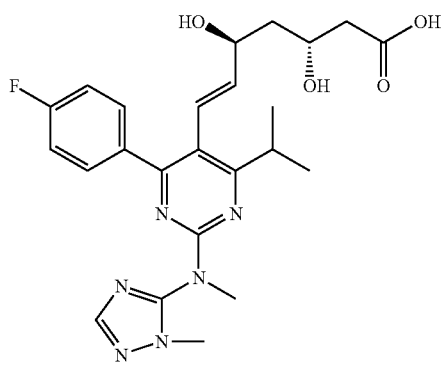 | 485 |

-continued

| Example No. | Structure | MS [M + H]+ |
|---|---|---|
| 57 | 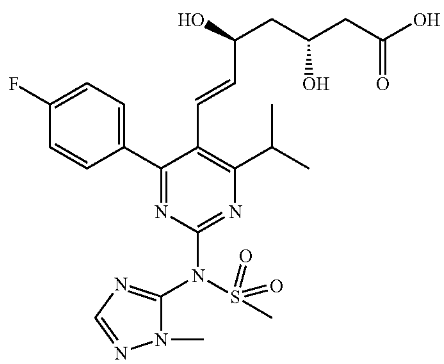 | 549 |
| 58 | 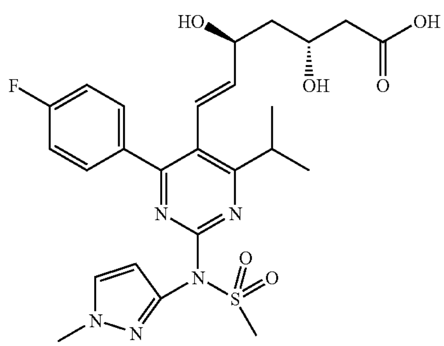 | 548 |
| 59 | 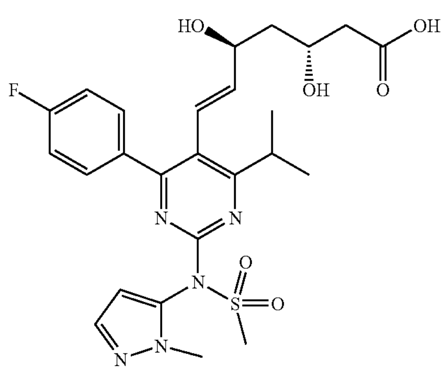 | 548 |
| 60 | 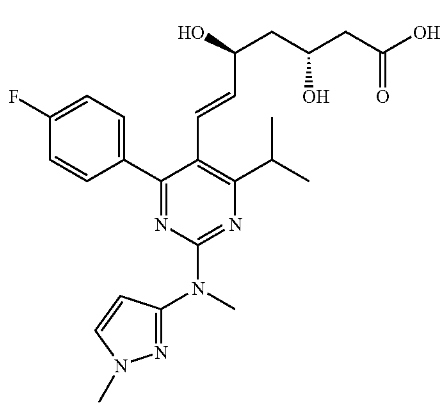 | 484 |

-continued
| Example No. | Structure | MS [M + H]+ |
|---|---|---|
| 61 | 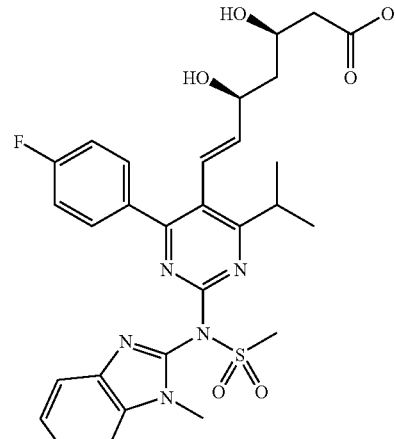 | 598 |
| 62 | 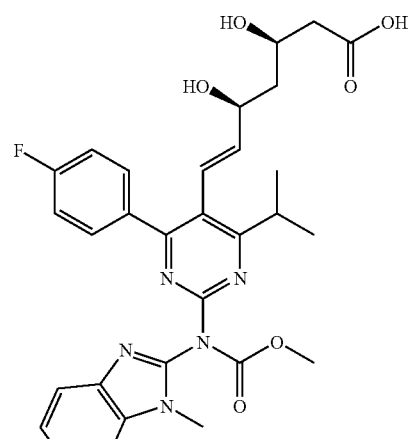 | 578 |
| 63 | 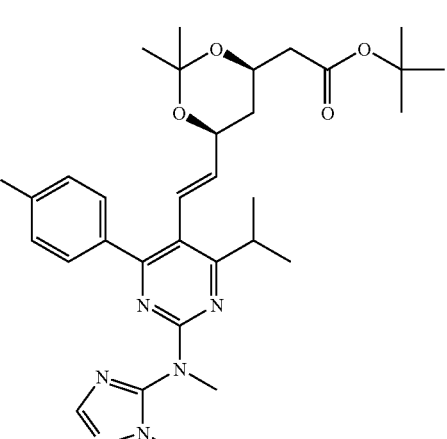 | 581 |

-continued
| Example No. | Structure | MS [M + H]+ |
|---|---|---|
| 64 | 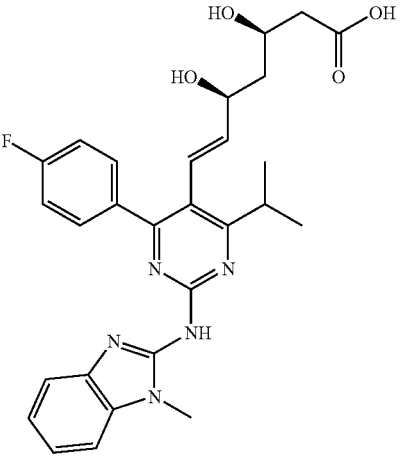 | 520 |
| 65 | 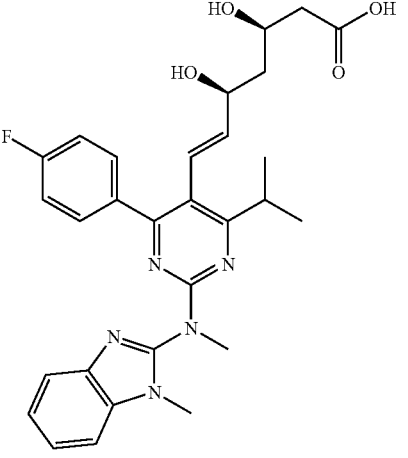 | 534 |
| 66 | 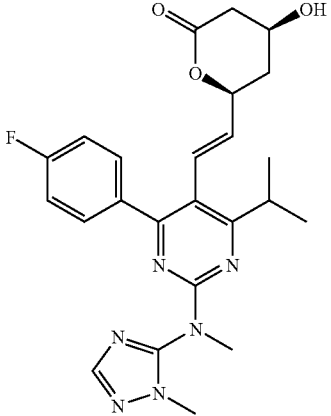 | 467 |

-continued

| Example No. | Structure | MS [M + H]+ |
|---|---|---|
| 67 | 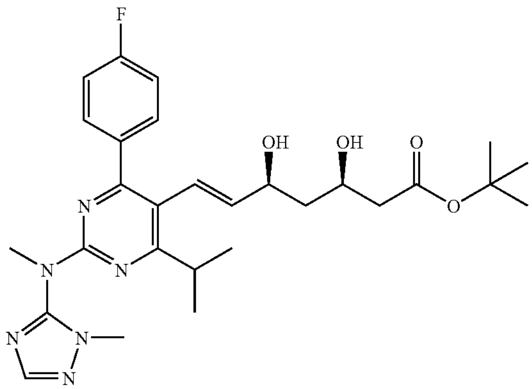 | 541 |
| 68 | 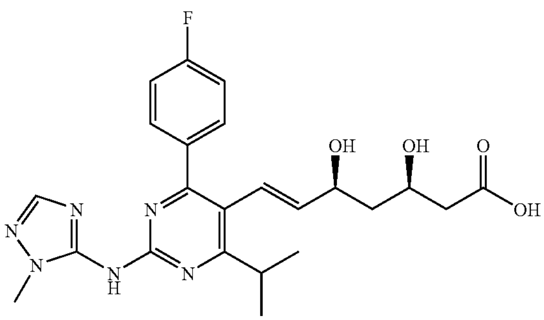 | 471 |

The following compounds were prepared employing the procedure set out in Examples 3, 4 and 5:

| Example No. | Structure | MS [M + H]+ |
|---|---|---|
| 69 | 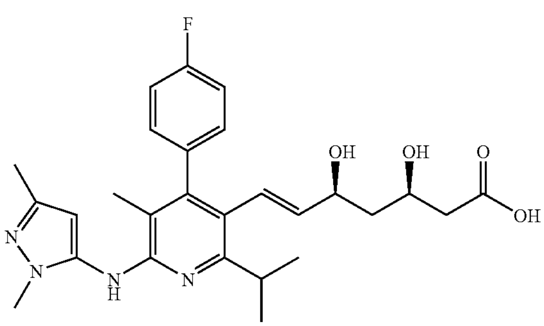 | 497 |
| 70 | 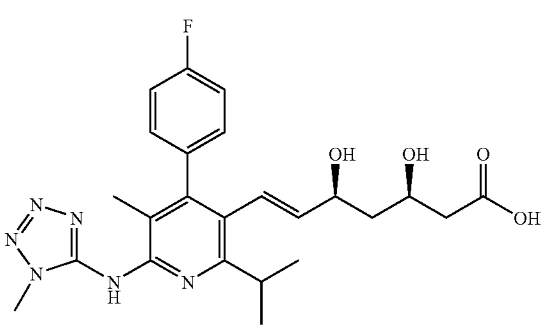 | 485 |

-continued

| Example No. | Structure | MS [M + H]⁺ |
|---|---|---|
| 71 | 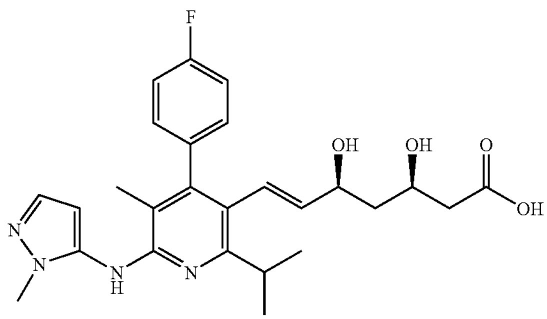 | 483 |
| 72 | 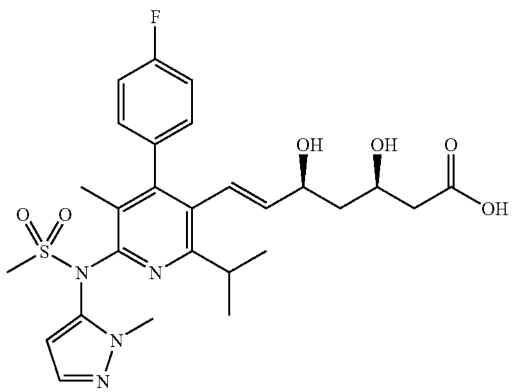 | 561 |
| 73 | 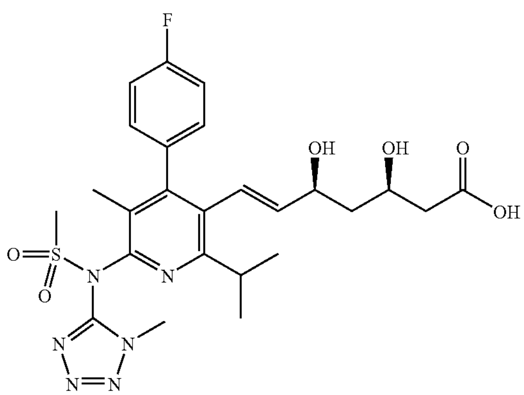 | 563 |
| 74 | 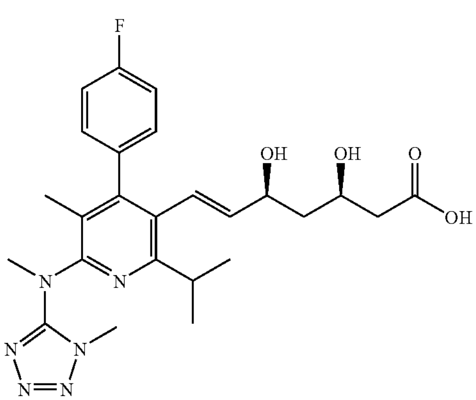 | 499 |

What is claimed is:

1. A compound of the formula

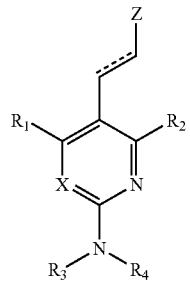

wherein X is N;
R$_1$ and R$_2$ are the same or different and are independently selected from H, alkyl, alkoxyalkyl, arylalkyl, cycloalkyl, alkenyl, cycloalkenyl, aryl, heteroaryl or cycloheteroalkyl;
R$_3$ is aryl, heteroaryl, cycloalkyl or cycloheteroalkyl;
R$_4$ is H, alkyl, cycloalkyl, haloalkyl, alkoxyalkyl, alkylthioalkyl, alkylsulfonyl, arylsulfonyl, alkoxycarbonyl, aryloxycarbonyl, heteroaryloxycarbonyl, alkylaminocarbonyl, arylaminocarbonyl, alkylthiocarbonyl, heteroarylaminocarbonyl, alkylaminosulfonyl, alkylcarbonyl, arylcarbonyl, heteroarylcarbonyl or heteroarylsulfonyl;

Z is 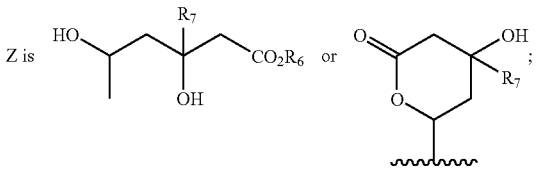

R$_6$ is H, or lower alkyl, a metal salt, methylamine salt, ammonium salt or dicyclohexylamine salt;
R$_7$ is H or lower alkyl;

and ⚏ represents a single bond or a double bond (which may be cis or trans);
or a pharmaceutically acceptable salt thereof where R$_6$ is H and all stereoisomers thereof.

2. The compound as defined in claim 1 wherein the Z group is in form of a free acid, or an alkali metal salt or alkaline earth metal salt thereof.

3. The compound as defined in claim 1 wherein
R$_1$ and R$_2$ are independently selected from alkyl, cycloalkyl and aryl;
R$_3$ is aryl, heteroaryl or cycloheteroalkyl; and
R$_4$ is H, alkyl, lower alkylcarbonyl, lower alkylsulfonyl or lower alkoxycarbonyl.

4. The compounds as defined in claim 1 wherein R$_1$ is aryl; and
R$_2$ is alkyl or cycloalkyl;
R$_3$ is aryl, heteroaryl, cycloheteroalkyl;
R$_4$ is H, lower alkyl, lower alkylcarbonyl, lower alkylsulfonyl or lower alkoxycarbonyl;

and ⚏ is a double bond.

5. The compound as defined in claim 1 wherein
R$_1$ is 4-fluorophenyl, 4-fluoro-3-methylphenyl or 3,5-dimethylphenyl;

R$_2$ is isopropyl, t-butyl or cyclopropyl;
R$_3$ is aryl which is phenyl, cycloheteroalkyl which is tetrahydrothiophene dioxide, a heteroaryl which is a pyrrazole, a thiadiazole, a pyrazine, pyrimidine, a benzimidazole, a triazole, a tetrazole, a pyridyl, a thiazole, an oxazole or an isoxazole, each of which may be optionally substituted with 1, 2 or 3 substituents which may be the same or different and which can be cycloheteroalkyl, heteroaryl, alkyl, halogen, carboxyl, alkoxycarbonyl, alkylaminocarbonyl, or alkoxy;
R$_4$ is H, methyl, methylcarbonyl, methoxycarbonyl or methanesulfonyl; ⚏ is a trans double bond; and Z is 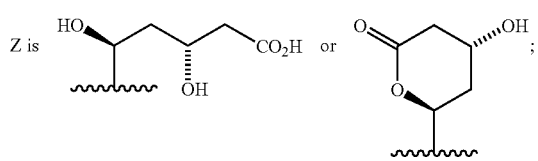

or an alkali or alkaline earth metal salt thereof.

6. The compound as defined in claim 1 having the formula I

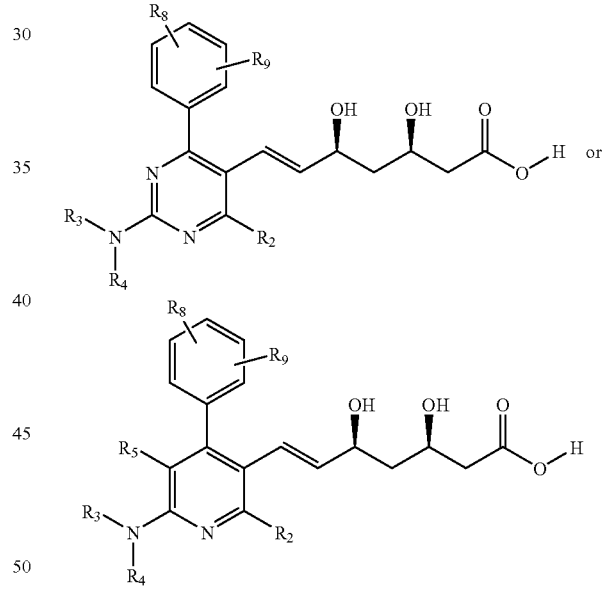

or an alkali or alkaline earth metal salt thereof,
wherein R$_8$ and R$_9$ are the same or different and independently selected from H, halogen or alkyl; and
R$_2$ is alkyl or cycloalkyl;
R$_3$ is aryl, heteroaryl or cycloheteroalkyl;
R$_4$ is H, C$_1$-C$_4$ alkyl, C$_1$-C$_4$ alkylcarbonyl, C$_1$-C$_4$ alkoxycarbonyl or C$_1$-C$_4$ alkylsulfonyl.

7. The compound as defined in claim 6 wherein
R$_8$ and R$_9$ are the same or different and are independently selected from 4-fluoro, 4-fluoro-3-methyl, or 3,5-dimethyl;
R$_2$ is isopropyl, t-butyl or cyclopropyl;
R$_3$ is one of the following groups:

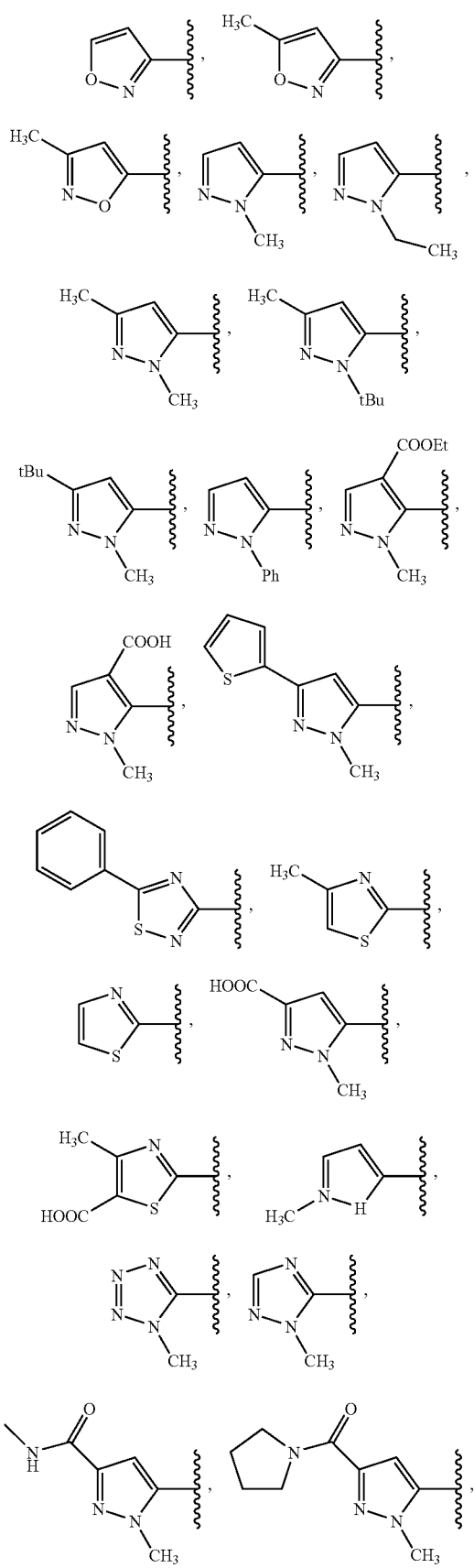
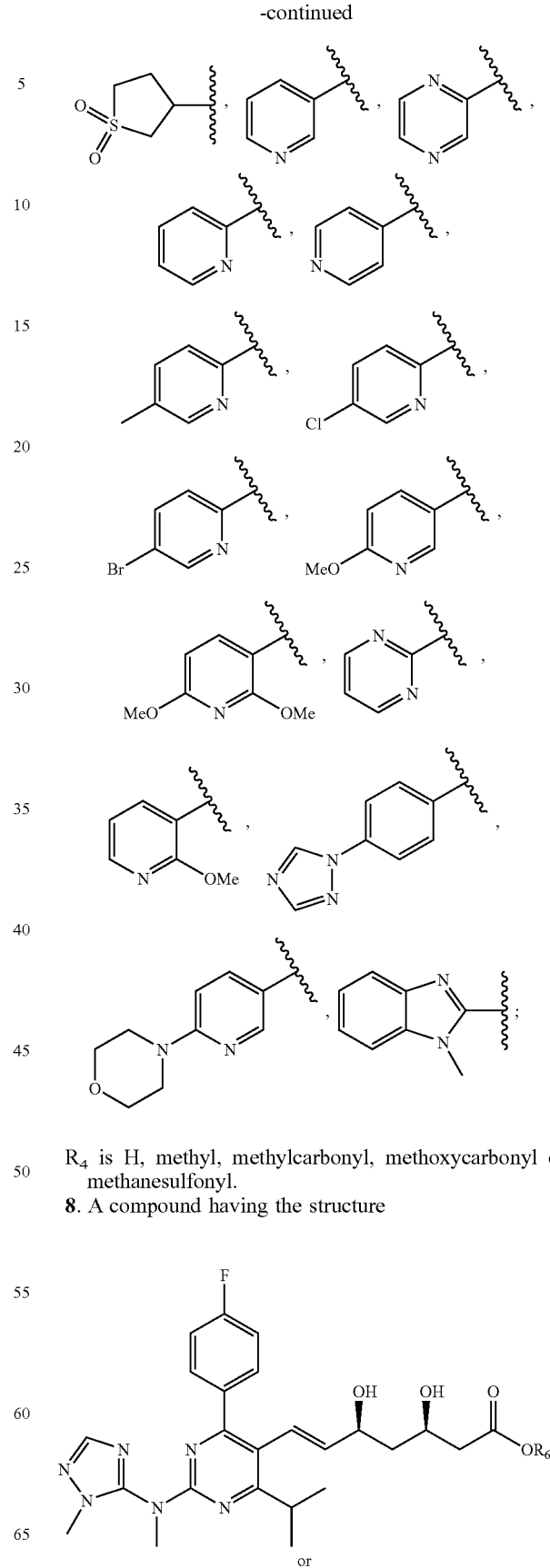
$R_4$ is H, methyl, methylcarbonyl, methoxycarbonyl or methanesulfonyl.
8. A compound having the structure
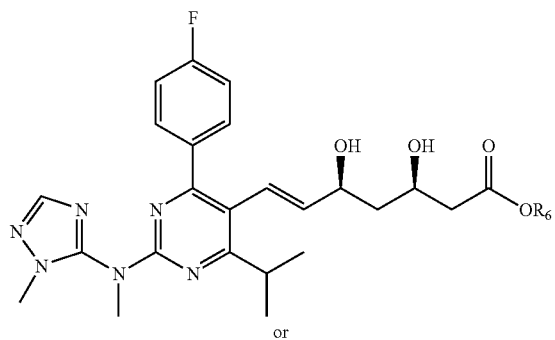
or -continued

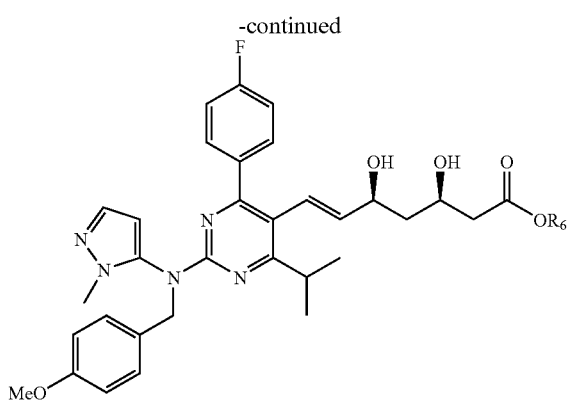

where $R_6$ is H, an alkyl or an alkali metal salt.

9. The compound as defined in claim 8 wherein $R_6$ is methylamine salt, ammonium salt, dicyclohexylamine salt, t-butyl, Na salt or Ca salt.

10. A pharmaceutical composition comprising a compound as defined in claim 1 and a pharmaceutically acceptable carrier therefor.

11. A pharmaceutical combination comprising the HMG CoA reductase inhibitor compound as defined in claim 1 and one or more hypolipidemic agents or lipid-lowering agents, or lipid agents, or lipid modulating agents, and/or one or more other types of therapeutic agents including antidiabetic agents, anti-obesity agents, antihypertensive agents, platelet aggregation inhibitors, anti-dementia agents, anti-Alzheimer's agents, anti-osteoporosis agents, and/or hormone replacement therapeutic agents, and/or other cardiovascular agents, anti-anginal agents, anti-arrhythmic agents, anti-atherosclerosis agents, anti-inflammatory agents, anti-arthritis agents, anti-platelet agents, anti-heart failure agents, anti-cancer agents, anti-infective agents, hormone replacement agents, growth hormone secretagogues, selective androgen receptor modulators, and/or immunomodulatory agents.

12. The combination as defined in claim 11 wherein the hypolipidemic agent or lipid-lowering agent or other lipid agent or lipid modulating agent or anti-atherosclerotic agent, which is employed comprises 1,2,3 or more MTP inhibitors, squalene synthetase inhibitors, fibric acid derivatives, PPAR α agonists, PPAR dual α/γ agonists, PPAR δ agonists, ACAT inhibitors, lipoxygenase inhibitors, cholesterol absorption inhibitors, ileal $Na^+$/bile acid cotransporter inhibitors, upregulators of LDL receptor activity, cholesteryl ester transfer protein inhibitors, bile acid sequestrants, or nicotinic acid and derivatives thereof, ATP citrate lyase inhibitors, phytoestrogen compounds, an HDL upregulators, LDL catabolism promoters, antioxidants, PLA-2 inhibitors, anti-homocysteine agents, HMG-CoA synthase inhibitors, lanosterol demethylase inhibitors, or sterol regulating element binding protein-I agents.

13. The pharmaceutical combination as defined in claim 11 comprising said HMG CoA reductase inhibiting compound and an antidiabetic agent which comprises 1,2,3 or more antidiabetic agents or antihyperglycemic agents which is an insulin secretagogue or insulin sensitizer, which is selected from biguanides, sulfonyl ureas, PTP-1B inhibitors, aldose reductase inhibitors, glucosidase inhibitors, PPAR γ agonists, PPAR α agonists, PPAR δ antagonists or agonists, aP2 inhibitors, PPAR α/γ dual agonists, dipeptidyl peptidase IV (DP4) inhibitors, SGLT2 inhibitors, glycogen phosphorylase inhibitors, and/or meglitinides, insulin, slow release insulin-Basulin™, and/or glucagon-like peptide-1 (GLP-1) or a mimetics thereof.

14. The combination as defined in claim 13 wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, Gl-262570, isaglitazone, JTT-501, NN-2344, L895645, YM-440, R-119702, AJ9677, repaglinide, nateglinide, KAD1129, AR-HO39242, GW-409544, KRP297, AC2993, LY315902, P32/98, NVP-DPP-728A, NVP-LAF-237, muraglitazar, BMS 477,188, and/or BMS 538,305.

15. The combination as defined in claim 11 wherein the other type of therapeutic agent which may be optionally employed is 1, 2, 3 or more of an anti-obesity agent which is a beta 3 adrenergic agonist, a lipase inhibitor, a serotonin (and dopamine) reuptake inhibitor, an aP2 inhibitor, a thyroid receptor beta drug, an anorectic agent, a PTP-1B inhibitor, a CCKA agonist, a neuropeptide Y antagonist, a melanocortin-4-receptor agonist, a PPAR modulator which is a PPAR γ antagonist, PPAR α agonist, and/or PPAR δ antagonist, a leptin inhibitor such as a leptin receptor activator, a fatty acid oxidation upregulator or inducer, a 5HT2c-agonist or an ACC inhibitor.

16. The combination as defined in claim 11 wherein the anti-obesity agent is orlistat, ATL-962, AJ9677, L750355, CP331648, sibutramine, topiramate, axokine, dexamphetamine, phentermine, phenylpropanolamine, and/or mazindol, P57 or CP-644673 (Pfizer); the lipid modulating agent is an MTP inhibitor, a squalene synthetase inhibitor, a fibric acid derivative, an upregulator of LDL receptor activity, a lipoxygenase inhibitor, or an ACAT inhibitor and the other lipid agent is a cholesteryl ester transfer protein inhibitor; and the antihypertensive agent employed is an ACE inhibitor, angiotensin II receptor antagonist, NEP inhibitor, a NEP/ACE inhibitor, a calcium channel blocker, a T-channel calcium antagonist, a β-adrenergic blocker, a diuretic, a α-adrenergic blocker, a dual action receptor antagonist (DARA), or a heart failure drug, wherein the antihypertensive agent is an ACE inhibitor which is captopril, fosinopril, enalapril, lisinopril, quinapril, benazepril, fentiapril, ramipril or moexipril;

an NEP/ACE inhibitor which is omapatrilat, gemopatrilat, or CGS 30440;

an angiotensin II receptor antagonist which is irbesartan, losartan or valsartan; amlodipine besylate, prazosin HCl, verapamil, nifedipine, nadolol, propranolol, or clonidine HCl, carvediol, atenolol, hydrochlorothiazide, torasemide, furosemide, spironolactone or indapamide; and the lipid modulating agent is fenofibrate, gemfibrozil, clofibrate, avasimibe, TS-962, MD-700, cholestagel, torcetrapib, JTT-705, niacin, LY295427, muraglitazar, and/or ezetimibe.

17. The combination as defined in claim 11 wherein the HMG CoA reductase inhibitor is in combination with a platelet aggregation inhibitor.

18. The combination as defined in claim 17 wherein the platelet aggregation inhibitor is aspirin, clopidogrel, ticlopidine, dipyridamole, ifetroban, abciximab, tirofiban, eptifibatide, anagrelide, CS-737, melagatran, ximelagatran, razaxaban, or a combination of clopidogrel and aspirin.

19. The combination as defined in claim 11 wherein the other therapeutic agent is an anti-Alzheimer's agent or anti-dementia agent, which is tacrine HCl (Cognex®), donepezil (Aricept®), a Y-secretase inhibitor, a β-secretase inhibitor and/or antihypertensive agent;

an antiosteoporosis agent, which is parathyroid hormone, a bisphosphonate, alendronate, a Ca receptor agonist or a progestin receptor agonist;

a hormone replacement therapeutic agent, which is a selective estrogen receptor modulator (SERM);

a tyrosine kinase inhibitor;

a selective androgen receptor modulator;

an antiarrhythmic agent, which is a β-blocker, or a calcium channel blocker, or an α-adrenergic blocker;

coenzyme Q sub. 10;

an agent that upregulates type III endothelial cell nitric acid syntase;

a chondroprotective compound which is polysulfated glycosaminoglycan (PSGAG), glucosamine, chondroitin sulfate (CS), hyaluronic acid (HA), pentosan polysulfate (PPS), doxycycline or minocycline;

a cyclooxygenase (COX)-2 inhibitor, which is Celebrex® (Searle) or Vioxx® (Merck) or a glycoprotein IIa/IIIb receptor antagonist;

a 5-HT reuptake inhibitor;

a growth hormone secretagogue;

an anti-atherosclerosis agent;

an anti-infective agent, or an immunosuppressant for use in transplantation, or an antineoplastic agent.

20. A method for lowering blood serum cholesterol levels treating Type 2 diabetes, insulin resistance, hyperglycemia, and/or hyperinsulinemia, which comprises administering to a mammalian species in need of treatment a therapeutically effective amount of a compound as defined in claim 1.

* * * * *